(12) United States Patent
Higgs

(10) Patent No.: US 9,115,063 B2
(45) Date of Patent: Aug. 25, 2015

(54) FLUOROPHORE AND FLUORESCENT SENSOR COMPOUND CONTAINING SAME

(75) Inventor: Timothy Charles Higgs, Saffron Waldon (GB)

(73) Assignee: Lightship Medical Limited, London (GB)

( * ) Notice: Subject to any disclaimer, the term of this patent is extended or adjusted under 35 U.S.C. 154(b) by 370 days.

(21) Appl. No.: 13/263,307

(22) PCT Filed: Apr. 8, 2010

(86) PCT No.: PCT/GB2010/000711
§ 371 (c)(1),
(2), (4) Date: Oct. 6, 2011

(87) PCT Pub. No.: WO2010/116142
PCT Pub. Date: Oct. 14, 2010

(65) Prior Publication Data
US 2012/0156793 A1    Jun. 21, 2012

(30) Foreign Application Priority Data
Apr. 9, 2009    (GB) .................. 0906318.1

(51) Int. Cl.
C07C 311/39    (2006.01)
G01N 21/64    (2006.01)
C07D 221/18    (2006.01)
G01N 33/58    (2006.01)

(52) U.S. Cl.
CPC .......... *C07C 311/39* (2013.01); *C07D 221/18* (2013.01); *G01N 33/582* (2013.01); *Y10T 436/144444* (2015.01)

(58) Field of Classification Search
None
See application file for complete search history.

(56) References Cited

U.S. PATENT DOCUMENTS

| 6,387,672 B1 | 5/2002 | Arimori et al. |
| 2006/0083688 A1 | 4/2006 | Singaram et al. |

FOREIGN PATENT DOCUMENTS

| CN | 101446555 | 6/2009 |
| WO | 00/03034 | 1/2000 |
| WO | 2006/094116 | 9/2006 |
| WO | 2008/142177 | 11/2008 |

OTHER PUBLICATIONS

Albericio et al., "Convenient Syntheses of Fluorenylmethyl-Based Side Chain Derivatives of Glutamic and Aspartic acids, Lysine, and Cysteine", Synthesis, 1990, 119.
Altomare et al., "SIR97: a new tool for crystal strnctnre determination and refinement", J. App. Cryst. (1999). 32, 115-119.

Arimori, et al.: "A modular fluorescence intramolecular energy transfer saccharide sensor" Organic letters, vol. 4, No. 24, Nov. 8, 2002, pp. 4249-4251, XP002590940.
Arimori, et al.: "Modular fluroscence sensors for saccharides" Journal of the Chemical Society, Perkin Transactions 1, No. 6, Feb. 18, 2002, pp. 803-808, XP002590886.
Croisy-Delcey et al., Bull.Soc.Chim.Fr., 1972, No. 3, pp. 1084-1092 with English translation of abstract.
Dale et al., "Substituted Styrenes. VI. Syntheses of the Isollleric Forlllylstyrenes and 0- and m • Vinylbenzoic Acid", J.Org.Chem., 1961, 26, pp. 2225-2227.
Database Caplus, Chemical abstracts service, Columbus, Ohio, US; 1999, XP002590766.
Fabian: "Zur Farbigkeit gekoppelter Oxonol-und Cyaninfarbstoffe" Journal fur Praktische Chemie, vol. 320, No. 3, 1978, pp. 361-376 (English Abstract only), XP002590767.
Haroune, CHEMISPEC—University of Sunderland, "NMR Analysis Report—Ketalised Acetylanthracene Intermediate", 2008.
Hashimoto, et al.: "Preparation of pure isomers of dinitropyrenes" Chemical and Pharmaceutical Bulletin, vol. 32, No. 5 1984, pp. 1992-1994, XP002590768.
Hilal et al., "A Rigorous Test for SPARC's Chemical Reactivity Models: Estimation of More Than 4300 Ionization pKas", Quant. Struct.-Act. Relat. 14:348-355 (1995).
Holland et al., "Preparation and Anticonvulsant Activity of N-Substituted Benzenedisulfonamides", J.Med, Chem., 1963, 6,307.

(Continued)

Primary Examiner — Alicia L Otton
(74) Attorney, Agent, or Firm — Fish & Richardson P.C.

(57) ABSTRACT

The invention provides fluorophores of formulae (I) and (II) and also fluorescent sensor compounds comprising fluorophore moieties based on such fluorophores in combination with a receptor moiety. There is further provided a method of sensing the presence of a target analyte using the fluorescent sensor compound, as well as the use of the fluorescent sensor compounds to sense a target analyte.

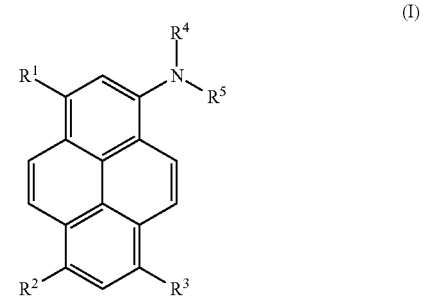

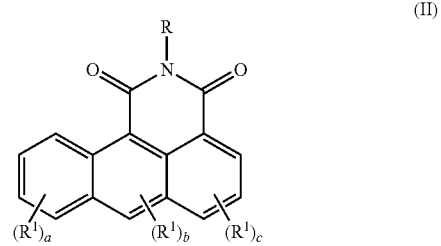

16 Claims, 1 Drawing Sheet

(56) References Cited

OTHER PUBLICATIONS

Ishiyama et al., "Palladium(O).Catalyzed Cross•Coupling Reaction of Alkoxydiboron with Haloarenes: A Direct Procedure for Arylboronic Esters", J. Org. Chem., 1995, 60 (23), 7508-7510.

Kawanishi et al., "A Study of Boronic Acid Based Fluorescent Glucose Sensors", Journal of Fluorescence, 2004, vol. 15, No. 5, pp. 499-512.

Kledzik et al., "Cu(II) recognition materials: Fluorophores grafted on mesoporous silica supports", Applied Surface Science, 254, 2007, 441-451.

Koskela, et al.: "A ditopic fluorescent sensor for potassium fluoride" Journal of the Chemical Society, Chemical Communications, No. 7, Feb. 21, 2005, pp. 945-947, XP002591076.

Kumar et al., "Zn(OTt)2-Catalyzed Cyclization of Propargyl Alcohols with Anilines, Phenols, and Amides for Synthesis of Indoles, Benzofurans, and Oxazoles through Different Annulation Mechanisms", J. Org. Chem., 2006, 71, 4951-4955.

Leebrick et al., "Synthesis and Reactions of p-Vinylphenylmagnesium Chloride", J.Org.Chem., 1958, vol. 23, pp. 935-936.

Luvino, et al.: "Selective fluorescence-based detection of dihydrouridine with boronic acids" Tetrahedron letters, vol. 47, No. 52, Dec. 25, 2006, pp. 9253-9256, XP025005226.

Miyaura et al., "Palladium-Catalyzed Cross-Coupling Reactions of Organoboron Compounds", Chem. Rev., 1995, 95, 2457.

Murata et al., "A general and efficient method for the palladium-catalyzed cross-coupling of thiols and secondary phosphines", Tetrahedron, 2004, 60, 7397-7403.

Netherton et al., "Room-Temperature Alkyl-Alkyl Suzuki Cross-Coupling of Alkyl Bromides that Possess β Hydrogens", J..Am. Chem. Soc. 2001, 123, 10099-10100.

Purohit, et al.: "Synthesis and characterisation of oligodeoxynucleotides containing the major DNA adducts formed by 1,6- and 1,8-dintropyrene" Organic letters, vol. 2, No. 13, May 27, 2000, pp. 1871-1874, XP002590770.

Rifani et al., "Solid State Dye Lasers from Stereospecific Host-Guest Interactions", J.Am.Chem.Soc., 1995, vol. 117, pp. 7572-7573.

Ruiz-Gayo et al., "(S)-9-Fluorenylmethyl-L-cysteine, a Useful HF-stable Derivative for Peptide Synthesis", J. Chem. Soc., Chem. Commun., 1986, 1501.

Sharret et al., "Exploring the use of APTS as a fluorescent reporter dye for continuous glucose sensing", Organic and Biomolecular Chemistry 7, 2009, 1461-1470.

Sheldrick et al., "A short history of SHELX", Acta Cryst. (2008), A64, 112-122.

Tan et al., "An optical sensor based on covalent immobilization of 1-aminopyrene using Au nanoparticles as bridges and carriers", Sensors and Actuators B, 124, 2007, 68-73.

Urawa et al., "A Convenient Method for Preparing Aromatic α,β-Unsaturated Ketones from α,β-Unsaturated Acyl Chlorides and Arylboronic Acids via Suzuki-Miyaura Type Coupling Reaction", Synthesis, 2003, 2882-2885.

Van Bekkum, et al.: "Sensitive and selective detection of urinary 1-nitropyrene metabolites following administration of a single intragastric dose of Diesel exhaust particles (SRM 2975) to Rats" Chemical research in toxicology, vol. 11, No. 11, Oct. 29, 1998, pp. 1382-1390, XP002590769.

Wong et al., "Isothiocyanates from Tosyl Chloride Mediated Decomposition of in Situ Generated Oithiocarhamic Acid Salts", J.Org. Chem, 2007, 72, 3969-3971.

Yale et al., "Synthetic Hypoglycemic Agents. I", J.Am.Chem.Soc., 1953, vol. 75, pp. 675-678.

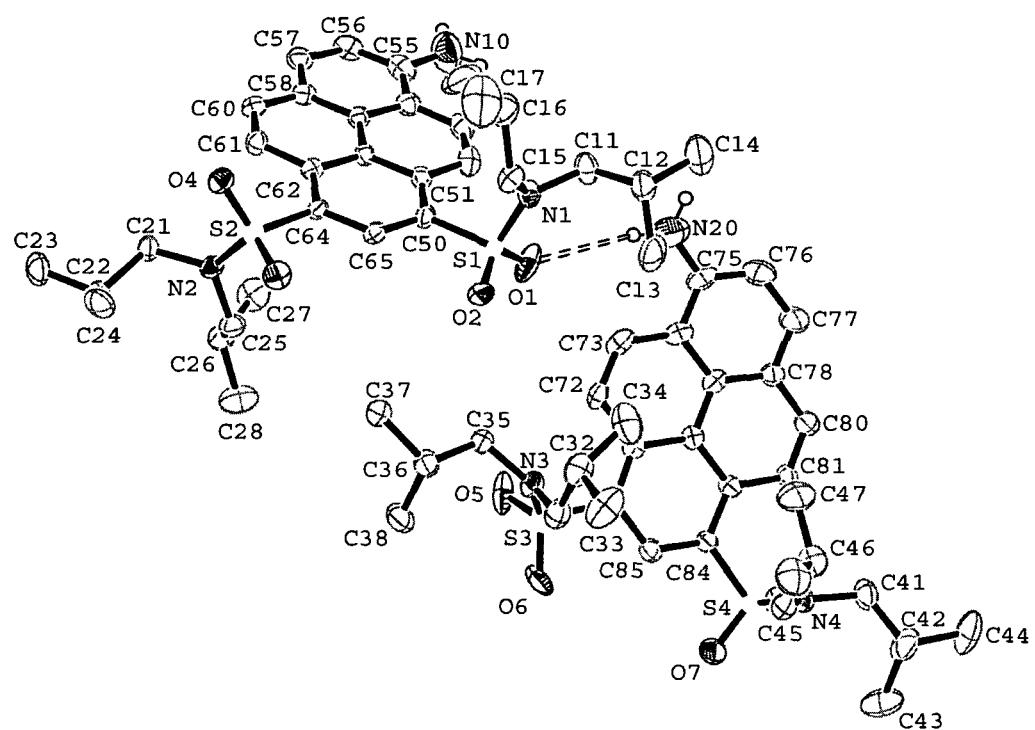

FLUOROPHORE AND FLUORESCENT SENSOR COMPOUND CONTAINING SAME

This application is the U.S. national stage under 35 USC §371 of International Application Number PCT/GB2010/000711, filed on 8 Apr. 2010, which claims priority to GB Application No. 0906318.1, filed on 9 Apr. 2009, the entire contents of which is hereby incorporated by reference.

The present invention relates to a fluorophore and to a fluorescent sensor compound which contains the fluorophore. The invention also provides a method of sensing the presence of an analyte using the fluorescent sensor compound.

BACKGROUND TO THE INVENTION

Invasive and implantable sensor devices have been developed in recent years which typically involve an indicator whose optical properties are altered in the presence of the analyte of interest. For example, fluorophores linked to a receptor capable of binding to the target analyte have been used as indicators in such sensors. A compound which comprises a combination of such a fluorophore and a receptor is known as a fluorescent sensor compound. Such fluorescent sensor compounds are known for both qualitative and quantitative sensing of analytes. The fluorescent sensor compounds may also comprise an anchor moiety which is capable of attaching the sensor compound to a substrate. For example, an anchor moiety may be capable of binding to, or being entrapped within, a hydrogel, with the hydrogel being incorporated within or onto an optical fibre which forms a part of sensing apparatus.

There is an ongoing need for novel fluorescent sensor compounds, for example based on novel fluorophore molecules, to be developed.

SUMMARY OF THE INVENTION

We now provide novel fluorophores which can be used in fluorescent sensor compounds. The fluorophores are particularly useful in the preparation of fluorescent sensor compounds suitable for use in sensing the presence of glucose.

The present invention therefore provides a fluorescent sensor compound comprising a fluorophore moiety and a receptor moiety, wherein the receptor moiety is capable of selectively interacting with an analyte and wherein the fluorescence of the fluorophore moiety is perturbed upon interaction of the receptor moiety with said analyte, characterised in that the fluorophore moiety is of formula (Ia) or (IIa):

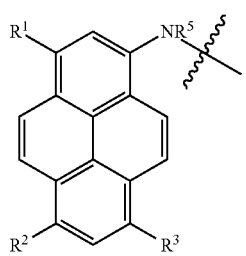

(Ia)

wherein:
$R^2$ and $R^3$ are the same or different and each represent a hydrogen atom or a group $-SO_2R^6$ wherein $R^6$ represents a chlorine atom or a group of formula $-NR^7R^8$, $-NA^1A^2$, $-NR^7A^1$, $C_{1-6}$ alkyl, $C_{1-6}$ hydroxyalkyl, $C_{2-6}$ alkenyl, $C_{6-10}$ aryl, $C_{6-10}$ aryl($C_{1-6}$)alkyl, halo($C_{1-6}$)alkyl or $-OR'$ where $R'$ is hydrogen or $C_{1-6}$ alkyl;

$R^1$ represents:
a hydrogen or halogen atom;
a group $-SO_2R^6$ where $R^6$ is as defined for $R^2$ and $R^3$;
a group $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, thiocyanate, $C_{1-4}$ hydroxyalkyl, $-COH$, $-COCl$, $-CH_2OR$, $-CH_2NHR$, $-OR$, $-NHR$, $-SR'$, $-NR'R''$ or $-N^+R'R''R'''$ where R is (meth)acryl, $-CO-C(CH_2)-CH_3$ or $-CH_2-Ph-CH_2=CH_2$ and R', R'' and R''' are the same or different and represent hydrogen or unsubstituted $C_{1-2}$ alkyl;
a phosphine, phosphinate, phosphonate, phosphine oxide or phosphonite group;
a group $-COO^-$ or $-COOR$ where R represents hydrogen, $C_{1-6}$ alkyl, $C_{6-10}$ aryl, 5- to 10-membered heteroaryl or 5- to 10-membered heterocyclyl;
a group of formula (A):

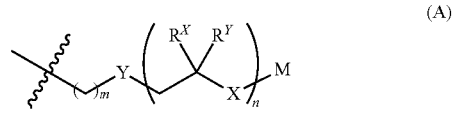

(A)

where m is 0 or 1, X and Y are the same or different and represent $-O-$, $-S-$ or $-NR-$ where R is hydrogen or $C_{1-4}$ alkyl, n is an integer of from 1 to 20, $R^X$ and $R^Y$ are the same or different and represent hydrogen, $C_{1-6}$ alkyl, $C_{6-10}$ aryl, 5- to 10-membered heteroaryl or 5- to 10-membered heterocyclyl, and M represents hydrogen, (meth)acryl or 4-vinylbenzyl; or
a polymerisable group;

$R^7$ and $R^8$ are the same or different and represent a hydrogen atom or a group selected from $C_{1-10}$ alkyl and $C_{2-10}$ alkenyl;
$A^1$ and $A^2$ are the same or different and represent a phenyl or 5- to 6-membered heteroaryl group;
$R^5$ represents hydrogen, acyl, $C_{1-6}$ alkyl, benzyl, $C_{6-10}$ aryl, 5- to 10-membered heteroaryl or 5- to 10-membered heterocyclyl;
wherein the alkyl, alkenyl, aryl and heteroaryl groups or moieties of $R^6$, $R^7$, $R^8$, $A^1$ and $A^2$ may optionally bear one or more polymerisable groups and/or one or more ionic water-solubilising groups, or the aryl and heteroaryl groups may themselves represent a cyclic ionic water-solubilising substituent; and
wherein the pyrene ring may further optionally bear one or more ionic water-solubilising groups and/or one or more polymerisable groups; or

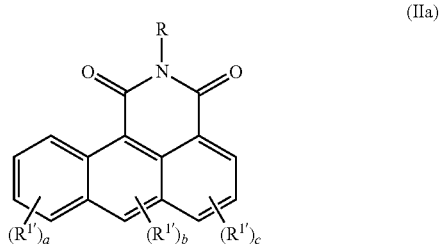

(IIa)

wherein:
two of a, b and c are zero and the other one of a, b and c is one;

R is selected from $C_{6-14}$ aryl, 5- to 10-membered heteroaryl, $C_{3-7}$ carbocyclyl, 5- to 10-membered heterocyclyl, $C_{1-10}$ alkyl, $C_{1-10}$ alkoxy, —$C_{1-10}$ alkyl-$SR^7$ (where $R^7$ represents hydrogen or $C_{1-10}$ alkyl), $C_{2-10}$ alkenyl, $C_{2-10}$ alkenyloxy, $C_{1-10}$ haloalkyl, $C_{2-10}$ haloalkenyl, $C_{1-10}$ haloalkoxy, $C_{2-10}$ haloalkenyloxy, hydroxyl, $C_{1-10}$ hydroxyalkyl and —$NR^8R^9$ where $R^8$ and $R^9$ are the same or different and represent hydrogen or $C_{1-4}$ alkyl, wherein the alkyl, carbocyclyl, heterocyclyl, aryl and heteroaryl groups or moieties of R may optionally bear one or more polymerisable groups and/or one or more ionic water-solubilising groups or the aryl and heteroaryl groups and moieties of R may themselves represent a cyclic ionic water-solubilising substituent; and $R^{1'}$ represents the point of attachment of the fluorophore moiety to the rest of the fluorescent sensor compound;

wherein the phenyl groups in the anthracenyl moiety of formula (IIa) are optionally further substituted by one or more optional substituents, and wherein the phenyl groups in the anthracenyl moiety of formula (IIa) may optionally bear one or more ionic water-solubilising groups and/or one or more polymerisable groups.

The present invention also provides a fluorophore of formula (I) or a salt thereof:

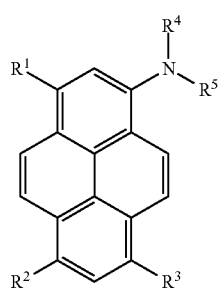

(I)

wherein:

$R^2$ and $R^3$ are the same or different and each represent a hydrogen atom or a group —$SO_2R^6$ wherein $R^6$ represents a chlorine atom or a group of formula —$NR^7R^8$, —$NA^1A^2$, —$NR^7A^1$, $C_{1-6}$ alkyl, $C_{1-6}$ hydroxyalkyl, $C_{2-6}$ alkenyl, $C_{6-10}$ aryl, $C_{6-10}$ aryl($C_{1-6}$)alkyl, halo($C_{1-6}$)alkyl or —$OR'$ where $R'$ is hydrogen or $C_{1-6}$ alkyl;

$R^1$ represents:

a hydrogen or halogen atom;

a group —$SO_2R^6$ where $R^6$ is as defined for $R^2$ and $R^3$;

a group $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, thiocyanate, $C_{1-4}$ hydroxyalkyl, —COH, —COCl, —$CH_2OR$, —$CH_2NHR$, —OR, —NHR, —SR', —NR'R'' or —$N^+R'R''R'''$ where R is (meth)acryl, —CO—C($CH_2$)—$CH_3$ or —$CH_2$-Ph-$CH_2$=$CH_2$ and R', R'' and R''' are the same or different and represent hydrogen or unsubstituted $C_{1-2}$ alkyl;

a phosphine, phosphinate, phosphonate, phosphine oxide or phosphonite group;

a group —$COO^-$ or —COOR where R represents hydrogen, $C_{1-6}$ alkyl, $C_{6-10}$ aryl, 5- to 10-membered heteroaryl or 5- to 10-membered heterocyclyl;

a group of formula (A):

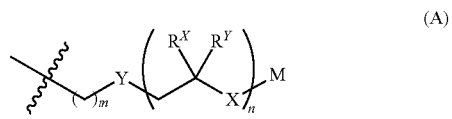

(A)

where m is 0 or 1, X and Y are the same or different and represent —O—, —S— or —NR— where R is hydrogen or $C_{1-4}$ alkyl, n is an integer of from 1 to 20, $R^X$ and $R^Y$ are the same or different and represent hydrogen, $C_{1-6}$ alkyl, $C_{6-10}$ aryl, 5- to 10-membered heteroaryl or 5- to 10-membered heterocyclyl, and M represents hydrogen, (meth)acryl or 4-vinylbenzene; or a polymerisable group;

$R^7$ and $R^8$ are the same or different and represent a hydrogen atom or a group selected from $C_{1-10}$ alkyl and $C_{2-10}$ alkenyl;

$A^1$ and $A^2$ are the same or different and represent a phenyl or 5- to 6-membered heteroaryl group;

$R^4$ and $R^5$ are the same or different and represent hydrogen, acyl, $C_{1-6}$ alkyl, benzyl, $C_{6-10}$ aryl, 5- to 10-membered heteroaryl or 5- to 10-membered heterocyclyl;

wherein at least one of $R^1$, $R^2$ and $R^3$ is other than hydrogen; and wherein the alkyl, alkenyl, aryl and heteroaryl groups or moieties of $R^6$, $R^7$, $R^8$, $A^1$ and $A^2$ may optionally bear one or more polymerisable groups and/or one or more ionic water-solubilising groups, or the aryl and heteroaryl groups may themselves represent a cyclic ionic water-solubilising substituent; and wherein the pyrene ring may further optionally bear one or more ionic water-solubilising groups and/or one or more polymerisable groups;

and with the proviso that $R^1$, $R^2$ and $R^3$ are not simultaneously hydrogen, or are not simultaneously —$SO_2R^6$ where $R^6$ is a chlorine atom or a hydroxy group.

The invention further provides a fluorophore of formula (II) or a salt thereof:

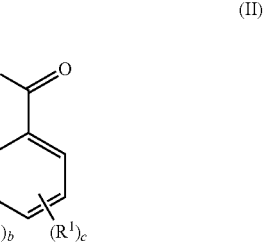

(II)

wherein:

two of a, b and c are zero and the other one of a, b and c is one;

R is selected from $C_{6-14}$ aryl, 5- to 10-membered heteroaryl, $C_{3-7}$ carbocyclyl, 5- to 10-membered heterocyclyl, $C_{1-10}$ alkyl, $C_{1-10}$ alkoxy, —$C_{1-10}$ alkyl-$SR^7$ (where $R^7$ represents hydrogen or $C_{1-10}$ alkyl), $C_{2-10}$ alkenyl, $C_{2-10}$ alkenyloxy, $C_{1-10}$ haloalkyl, $C_{2-10}$ haloalkenyl, $C_{1-10}$ haloalkoxy, $C_{2-10}$ haloalkenyloxy, hydroxyl, $C_{1-10}$ hydroxyalkyl and —$NR^8R^9$ where $R^8$ and $R^9$ are the same or different and represent hydrogen or $C_{1-4}$ alkyl, wherein the alkyl, carbocyclyl, heterocyclyl, aryl and heteroaryl groups or moieties of R may optionally bear one or more polymerisable groups and/or one or more ionic water-solubilising groups or the aryl and heteroaryl groups and moieties of R may themselves represent a cyclic ionic water-solubilising substituent; and $R^{1'}$ represents the point of attachment of the fluorophore moiety to the rest of the fluorescent sensor compound;

and wherein the phenyl groups in the anthracenyl moiety of formula (II) are optionally further substituted by one or more optional substituents, and wherein the phenyl groups in the anthracenyl moiety of formula (II) may optionally bear one or more ionic water-solubilising groups and/or one or more polymerisable groups.

The fluorescent sensor compound may be immobilized on or within a support substrate. In order to achieve this, the fluorescent sensor compound preferably comprises a polymerisable group capable of reacting with a support substrate (or precursor thereto) to immobilise the fluorescent sensor compound on or in the support substrate.

The invention further provides a sensor comprising a fluorescent sensor compound as defined above.

The present invention also provides a method of detecting the presence of a target analyte in a test substance, which method comprises:
(i) providing a fluorescent sensor compound as defined above and measuring its fluorescence in the absences of the test substance;
(ii) exposing said fluorescent sensor compound to the test substance and measuring the fluorescence of the compound again;
(iii) comparing the fluorescence measurements obtained in steps (i) and (ii); and
(iv) determining that the target analyte is present if the fluorescence measurement obtained in step (ii) is different from that obtained in step (i).

The invention further provides a method of detecting the presence of a target analyte in a test substance, which method comprises:
(i) exposing a fluorescent sensor compound as defined above to a test substance and measuring the fluorescence of the compound;
(ii) comparing the fluorescence measurement obtained in step (i) against a previously-determined fluorescence measurement of the fluorescent sensor compound in the absence of the target analyte; and
(iii) determining that the target analyte is present if the fluorescence measurement obtained in step (ii) is different from the previously-determined fluorescence measurement.

The invention also provides the use of a fluorescent sensor compound as defined above to detect the presence of a target analyte in a test substance. Preferably the target analyte is glucose.

BRIEF DESCRIPTION OF THE FIGURES

FIG. 1 depicts the crystal structure of 6-aminopyrene-1,3-disulfonic acid bis-diisobutylamide

DETAILED DESCRIPTION OF THE INVENTION

As used herein, a $C_{1-10}$ alkyl group or moiety is a linear or branched alkyl group or moiety containing from 1 to 10 carbon atoms, for example a $C_{1-6}$ alkyl or $C_{1-4}$ alkyl group or moiety containing from 1 to 6 or from 1 to 4 carbon atoms. Examples of $C_{1-4}$ alkyl groups include methyl, ethyl, n-propyl, i-propyl, n-butyl, i-butyl and t-butyl. For the avoidance of doubt, where two alkyl moieties are present in a group, the alkyl moieties may be the same or different.

As used herein, a $C_{2-10}$ alkenyl group or moiety is a linear or branched alkenyl group or moiety one having at least one double bond of either E or Z stereochemistry where applicable and containing from 2 to 10 carbon atoms, for example a $C_{2-6}$ alkenyl or $C_{2-4}$ alkenyl group or moiety containing from 2 to 6 or from 2 to 4 carbon atoms, such as —CH=CH$_2$ or —CH$_2$—CH=CH$_2$, —CH$_2$—CH$_2$—CH=CH$_2$, —CH$_2$—CH=CH—CH$_3$, —CH=C(CH$_3$)—CH$_3$ and —CH$_2$—C(CH$_3$)=CH$_2$. For the avoidance of doubt, where two alkenyl moieties are present in a group, they may be the same or different.

As used herein, a $C_{1-10}$ alkylene group or moiety is a linear or branched alkylene group or moiety, for example a $C_{1-6}$ alkylene or $C_{1-4}$ alkylene group or moiety. Examples include methylene, n-ethylene, n-propylene and —C(CH$_3$)$_2$— groups and moieties, with methylene being most preferred.

As used herein, a $C_{2-6}$ alkenylene group or moiety is a linear or branched alkenylene group or moiety, for example a $C_{2-4}$ alkenylene group or moiety. Examples include —CH=CH—, —CH=CH—CH$_2$—, —CH$_2$—CH=CH— and —CH=CH—CH=CH—.

As used herein, a halogen atom is typically chlorine, fluorine, bromine or iodine, more preferably chlorine, fluorine or bromine, more preferably chlorine or fluorine, most preferably chlorine.

As used herein, a $C_{1-10}$ alkoxy group or $C_{2-10}$ alkenyloxy group is typically a said $C_{1-10}$ alkyl (e.g. a $C_{1-6}$ alkyl or $C_{1-4}$ alkyl) group or a said $C_{2-10}$ alkenyl (e.g. a $C_{2-6}$ or $C_{2-4}$ alkenyl) group respectively which is attached to an oxygen atom.

A haloalkyl, haloalkenyl, haloalkoxy or haloalkenyloxy group is typically a said alkyl, alkenyl, alkoxy or alkenyloxy group respectively which is substituted by one or more said halogen atoms. Typically, it is substituted by 1, 2 or 3 said halogen atoms. Preferred haloalkyl and haloalkoxy groups include perhaloalkyl and perhaloalkoxy groups such as —CX$_3$ and —OCX$_3$ wherein X is a said halogen atom, for example chlorine or fluorine.

As used herein, a hydroxyalkyl group is an alkyl group substituted by one or more hydroxy groups. Typically, it is substituted by one, two or three hydroxy groups. Preferably, it is substituted by a single hydroxy group.

As used herein, a $C_{6-14}$ aryl group is preferably a phenyl, naphthyl or anthracenyl group, more preferably a $C_{6-10}$ aryl group such as a phenyl or naphthyl group, most preferably a phenyl group.

As used herein, a 5- to 10-membered heteroaryl group or moiety is a monocyclic or bicyclic 5- to 10-membered aromatic ring structure, such as a monocyclic 5- or 6-membered ring or a bicyclic 8- to 10-membered group, containing at least one heteroatom, for example 1, 2, 3 or 4 heteroatoms, selected from O, S and N. When the ring contains 4 heteroatoms these are preferably all nitrogen atoms. Preferably a 5- to 10-membered heteroaryl group or moiety is a monocyclic 5- to 6-membered ring. Examples of 5- to 6-membered monocyclic rings include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl, pyrazinyl, triazinyl and tetrazolyl groups. Preferred groups include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl and pyrazinyl groups. More preferred groups include pyrrolyl, imidazolyl, thiazolyl, pyrazolyl, pyridinyl, pyridazinyl, pyrimidinyl and pyrazinyl groups. Examples of 8- to 10-membered bicyclic groups include indolyl, benzimidazolyl, quinolinyl, isoquinolinyl, cinnolinyl, quinazolinyl, quinoxalinyl and naphthyridinyl.

As used herein, a 5- to 10-membered heterocyclyl group or moiety is a non-aromatic, saturated or unsaturated $C_{5-10}$ carbocyclic ring in which one or more, for example 1, 2, 3 or 4, of the carbon atoms are replaced with a moiety selected from N, O, S, S(O) and S(O)$_2$, and wherein one or more of the remaining carbon atoms is optionally replaced by a group —C(O)— or —C(S)—. When one or more of the remaining carbon atoms is replaced by a group —C(O)— or —C(S)—, preferably only one or two (more preferably two) such carbon atoms are replaced. Typically, the 5- to 10-membered heterocyclyl ring is a 5- to 6-membered ring. Suitable heterocyclyl groups and moieties include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxo-thiomorpholinyl, S,S-dioxo-thiomorpholinyl, morpholinyl, 1,3-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadiazol-2(3H)-thionyl, oxopyrrolidinyl, oxothiazolidinyl, oxopyrazolidinyl, succinimido and maleimido groups and moieties.

As used herein, a $C_{3-10}$ carbocyclic group or moiety is a non-aromatic saturated or unsaturated hydrocarbon ring having from 3 to 10 carbon atoms, for example from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 3 to 6 carbon atoms. Examples include cyclopropyl, cyclobutyl, cyclopentyl and cyclohexyl and their mono-unsaturated variants, more particularly cyclopentyl and cyclohexyl.

Unless otherwise stated, the alkyl and alkenyl groups and moieties are unsubstituted or substituted with 1, 2 or 3 unsubstituted substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, $C_{1-4}$ hydroxyalkyl, —P$^+$R$^{41}_4$, —SO$_2$H, —PO(OH)$_2$, —OSiR'R"R''', —SR', —NR'R" and —N$^+$R'R"R''' groups where R', R" and R''' are the same or different and represent hydrogen or unsubstituted $C_{1-4}$ alkyl and each R$^{41}$ is the same or different and represents $C_{1-4}$ alkyl. Other suitable substituents on alkyl and alkenyl groups and moieties are groups of formula —X—Y where X represents —O—, —S— or —NR— where R is hydrogen or unsubstituted $C_{1-4}$ alkyl, and Y represents hydrogen, (meth)acryl or 4-vinylbenzyl. When a group —X—Y is present as a substituent, preferably only one such group is present.

Preferred substituents on the alkyl and alkenyl groups and moieties are unsubstituted substituents selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{1-4}$ haloalkoxy, hydroxyl, $C_{1-4}$ hydroxyalkyl, —OSiR'R"R''' and —NR'R" where R' and R" are the same or different and represent hydrogen or unsubstituted $C_{1-4}$ alkyl. Further preferred substituents are unsubstituted substituents selected from halogen atoms and $C_{1-2}$ alkyl, $C_{1-2}$ alkoxy, $C_{1-2}$ haloalkyl, hydroxyl, $C_{1-4}$ hydroxyalkyl, —OSiR'R"R''' where R', R" and R''' are the same or different and represent hydrogen or unsubstituted $C_{1-4}$ alkyl, and —NR'R" where R' and R" are the same or different and represent hydrogen or unsubstituted $C_{1-2}$ alkyl. Further preferred substituents are unsubstituted substituents selected from halogen atoms and $C_{1-2}$ alkyl, $C_{1-2}$ alkoxy, hydroxyl, $C_{1-4}$ hydroxyalkyl and —NR'R" groups where R' and R" are the same or different and represent hydrogen or unsubstituted $C_{1-2}$ alkyl.

Unless otherwise stated, the aryl, carbocyclyl, heteroaryl and heterocyclyl groups and moieties are unsubstituted or substituted by 1, 2, 3 or 4 (more preferably 1, 2 or 3, more preferably 1 or 2 and most preferably 1) unsubstituted substituents selected from halogen atoms, and cyano, nitro, $C_{1-4}$ alkyl, $C_{1-4}$ alkoxy, $C_{2-4}$ alkenyl, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, $C_{1-4}$ hydroxyalkyl, —P$^+$R$^{41}_4$, —SO$_2$H, —PO(OH)$_2$, —SR', —NR'R" and —N$^+$R'R"R''' groups wherein each R', R" and R''' is the same or different and represents hydrogen or unsubstituted $C_{1-2}$ alkyl and wherein each R$^{41}$ is the same or different and represents $C_{1-2}$ alkyl, or from substituents of formula —COOH, —COOR$^A$, —COH, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NR$^B$COOH, —NHCOOH, —NHSO$_2$R$^A$, —NR$^B$SO$_2$R$^A$, —NHSO$_2$OR$^A$, —NR$^B$SO$_2$OH, —NHSO$_2$H, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent unsubstituted $C_{1-6}$ alkyl, $C_{3-7}$ carbocyclyl, phenyl or a 5- to 6-membered heteroaryl, or R$^A$ and R$^B$ when attached to the same nitrogen atom form a 5- or 6-membered heterocyclyl group. Where cyano and/or nitro groups are present, preferably the aryl or heteroaryl group or moiety bears no more than two, more preferably no more than one, such substituent. Possible other substituents on the aryl, carbocyclyl, heteroaryl and heterocyclyl groups include groups of formulae —X—Y and —X-(Alk-Z)$_n$—Y where X and Z are the same or different and represent —O—, —S— or —NR— where R is hydrogen or unsubstituted $C_{1-4}$ alkyl, Y represents hydrogen, (meth)acryl or 4-vinylbenzene, n represents an integer of from 1 to 20, and Alk represents a $C_{1-10}$ alkylene group which is unsubstituted or substituted with one or two substituents chosen from $C_{1-6}$ alkyl, $C_{6-10}$ aryl, 5- to 10-membered heteroaryl or 5- to 10-membered heterocyclyl. More preferably Alk represents a group —CH$_2$—CR$^X$R$^Y$— where R$^X$ and R$^Y$ are the same or different and represent hydrogen, $C_{1-6}$ alkyl, $C_{6-10}$ aryl, 5- to 10-membered heteroaryl or 5- to 10-membered heterocyclyl, more preferably R$^X$ and R$^Y$ represent hydrogen, $C_{1-6}$ alkyl or phenyl. More preferably R$^X$ and R$^Y$ both represent hydrogen. It is preferred that n represents an integer of from 1 to 10, more preferably an integer of from 1 to 5, most preferably n represents 1.

Preferred substituents on aryl, carbocyclyl, heteroaryl and heterocyclyl groups are unsubstituted substituents selected from halogen atoms, and cyano, nitro, $C_{1-4}$ alkyl, $C_{1-4}$ alkoxy, $C_{2-4}$ alkenyl, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, $C_{1-4}$ hydroxyalkyl, —SW and —NR'R" groups wherein each R' and R" is the same or different and represents hydrogen or unsubstituted $C_{1-2}$ alkyl. More preferred substituents are unsubstituted substituents selected from halogen atoms, and $C_{1-2}$ alkyl, $C_{1-2}$ alkoxy, $C_{1-2}$ haloalkyl, hydroxyl, $C_{1-4}$ hydroxyalkyl, —SR' and —NR'R" groups wherein each R' and R" is the same or different and represents hydrogen or unsubstituted $C_{1-2}$ alkyl. Further preferred substituents are unsubstituted substituents selected from halogen atoms, and $C_{1-2}$ alkyl, $C_{1-2}$ alkoxy, hydroxyl, $C_{1-4}$ hydroxyalkyl and —NR'R" groups wherein each R' and R" is the same or different and represents hydrogen or unsubstituted $C_{1-2}$ alkyl.

As used herein, the term phosphonium salt includes groups of formula —$P^+R^AR^BR^C$ wherein $R^A$, $R^B$ and $R^C$ are the same or different and represent a $C_{1-6}$ alkyl, $C_{6-10}$ aryl, 5- to 10-membered heteroaryl or a 5- to 10-membered heterocyclyl group.

As used herein, the term phosphine includes groups of formula —$PR^AR^B$ wherein $R^A$, $R^B$ are the same or different and represent a $C_{1-6}$ alkyl, $C_{6-10}$ aryl, 5- to 10-membered heteroaryl or a 5- to 10-membered heterocyclyl group.

As used herein, the term phosphine oxide includes groups of formula —$P(=O)R^AR^B$ wherein $R^A$ and $R^B$ are the same or different and represent a $C_{1-6}$ alkyl, $C_{6-10}$ aryl, 5- to 10-membered heteroaryl or a 5- to 10-membered heterocyclyl group.

As used herein, the term phosphinate includes groups of formula —$P(=O)R^AOR^B$ wherein $R^A$ and $R^B$ are the same or different and represent a hydrogen atom, or a $C_{1-6}$ alkyl, $C_{6-10}$ aryl, 5- to 10-membered heteroaryl or 5- to 10-membered heterocyclyl group.

As used herein, the term phosphinamide includes groups of formula —$P(=O)R^ANR^BR^C$ wherein $R^A$, $R^B$ and $R^C$ are the same or different and represent a hydrogen atom, or a $C_{1-6}$ alkyl, $C_{6-10}$ aryl, 5- to 10-membered heteroaryl or 5- to 10-membered heterocyclyl group.

As used herein, the term phosphonate includes groups of formula —$P(=O)OR^AOR^B$ wherein $R^A$ and $R^B$ are the same or different and represent a hydrogen atom or a $C_{1-6}$ alkyl, $C_{6-10}$ aryl, 5- to 10-membered heteroaryl or 5- to 10-membered heterocyclyl group.

As used herein, the term phosphonamide includes groups of formula —$P(=O)OR^ANR^BR^C$ wherein $R^A$, $R^B$ and $R^C$ are the same or different and represent a hydrogen atom or a $C_{1-6}$ alkyl, $C_{6-10}$ aryl, 5- to 10-membered heteroaryl or 5- to 10-membered heterocyclyl group.

As used herein, the term phosphonamide includes groups of formula —$P(=O)NR^AR^BNR^CR^D$ wherein $R^A$, $R^B$, $R^C$ and $R^D$ are the same or different and represent a hydrogen atom or a $C_{1-6}$ alkyl, $C_{6-10}$ aryl, 5- to 10-membered heteroaryl or 5- to 10-membered heterocyclyl group.

For the avoidance of doubt, the alkyl, aryl, heteroaryl and heterocyclyl groups in the phosphonium salt, phosphine, phosphine oxide, phosphinate, phosphinamide, phosphonate and phosphonamide groups are unsubstituted or substituted as generally defined earlier. For example, functionalised alkyl groups such as alkylalcohol groups and alkylamine groups are envisaged, as well as functionalised aryl groups such as phenol. More preferably the alkyl, aryl, heteroaryl and heterocyclyl groups are unsubstituted.

As used herein the term "salt" includes base addition, acid addition and quaternary salts. Fluorophores and fluorescent sensor compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

As used herein, an ionic water-solubilising group is a group which is capable of increasing the solubility of the fluorophore or fluorescent sensor molecule in an aqueous medium. The ionic water-solubilising group can thus be described as an ionic functionality on the fluorophore or sensor molecule. Suitable ionic water-solubilising groups include non-cyclic and cyclic groups. The ionic functionalities contain charged species which dissociate in an aqueous medium. The charged species are as defined below, and include suitable counterions which are necessary to balance the charge. Suitable such counterions will be known to a person skilled in the art.

Suitable non-cyclic ionic water-solubilising groups include, but are not limited to, sulfonic acid salts, phosphonic acid salts, phosphonium salts, ammonium salts and carboxylate salts. Sulfonic acid salts, ammonium salts and carboxylate salts are preferred. Exemplary sulfonic acid salts contain a group of formula —$SO_3^-$ and a suitable counterion. Exemplary phosphonic acid salts contain a group of formula —$P(=O)(OH)O^-$ or —$P(=O)O_2^{2-}$ and a suitable counterion. Exemplary phosphonium salts contain a group of formula —$P^+R^AR^BR^C$ and a suitable counterion where $R^A$, $R^B$ and $R^C$ are the same or different and represent alkyl, $C_{6-10}$ aryl or a 5- to 10-membered heteroaryl or heterocyclyl group. Exemplary ammonium salts contain a group of formula —$N^+R^DR^ER^F$ and a suitable counterion where $R^D$, $R^E$ and $R^F$ are the same or different and are as defined above for $R^A$, $R^B$ and $R^C$ or can further represent hydrogen. Exemplary carboxylate salts contain a group of formula —$COO^-$ and a suitable counterion.

Suitable cyclic ionic water-solubilising groups include, but are not limited to, $C_{6-10}$ aryl, $C_{3-7}$ carbocyclic, 5- to 10-membered heteroaryl and 5- to 10-membered heterocyclyl groups which are substituted with one or more, more preferably one, of the non-cyclic ionic water-solubilising groups discussed above. For example, suitable cyclic ionic water-solubilising groups include $C_{6-10}$ aryl groups, more preferably phenyl groups, substituted with one or more, more preferably one, of the non-cyclic ionic water-solubilising groups discussed above. Particularly preferred cyclic ionic water-solubilising groups include phenyl groups substituted with a sulfonic acid salt, a phosphonic acid salt, a phosphonium salt, an ammonium salt or a carboxylate salt, more preferably substituted with a sulfonic acid salt, a phosphonium salt, an ammonium salt or a carboxylate salt.

Suitable cyclic ionic water-solubilising groups also include, but are not limited to, ionic water-solubilising groups where the charge is borne by the cyclic group itself, for example by a tetravalent-nitrogen-containing heteroaryl group. These cyclic ionic water-solubilising groups thus comprise heteroaryl-based groups which are themselves charged (in contrast to the cyclic groups described above which are neutral but which bear an ionic water-solubilising group). Exemplary cyclic ionic water-solubilising groups of this type include pyridinium salts and imidazolium salts. Suitable pyridinium salts include groups of formula:

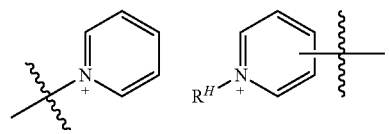

where $R^H$ represents $C_{1-6}$ alkyl, $C_{6-10}$ aryl or a 5- to 10-membered heteroaryl group.

Suitable imidazolium salts include groups of formula:

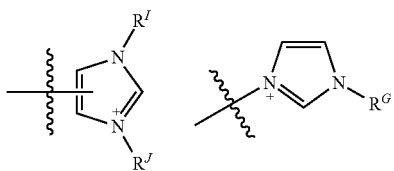

where $R^I$ and $R^J$ are the same or different and are as defined above for $R^A$, $R^B$ and $R^C$, and wherein $R^G$ is as defined above for $R^A$, $R^B$ and $R^C$.

Preferred ionic water-solubilising groups include sulfonic acid, phosphonic acid, phosphonium, ammonium and carboxylate salts, phenyl groups substituted with a sulfonic acid, phosphonic acid, phosphonium, ammonium or carboxylate salt, and pyridinium and imidazolium salts.

As used herein the term 'polymerisable group' is a group which is capable of undergoing a polymerisation reaction, typically a free radical polymerisation reaction. Exemplary polymerisable groups include a —C=C— or —C≡C— group. Preferred polymerisable groups include (meth)acrylate, vinylbenzyl (e.g. 3- or 4-vinylbenzyl), vinylene, (meth) acrylamide, N-vinylamide and allyl groups. (Meth)acrylate, vinylbenzyl and (meth)acrylamide, in particular (meth)acrylate and vinylbenzyl, are preferred. Where a (meth)acrylamide or N-vinylamide group is present, the trivalent nitrogen of the amide group is typically also bonded to a hydrogen atom or $C_{1-4}$ alkyl group. The term (meth)acrylate refers to the acryl and methacryl esters of a primary, secondary or tertiary alcohol functionality and the term and (meth)acrylamide refers to acryl and methacryl amides formed from a primary or secondary amine group.

The term polymerisable group also encompasses groups wherein the polymerisable functionality is linked to the fluorophore moiety via a spacer group. Such polymerisable groups include those of formula -spacer-$R^P$, wherein -spacer- is a $C_{6-10}$ aryl or $C_{1-10}$ alkylene group or a combination of such aryl and alkylene groups, such as an -alkylene-aryl-alkylene- moiety, wherein the alkylene component is optionally interrupted or terminated by one or more, e.g. one, heteroatoms selected from O, N and S. In one embodiment, -spacer- is a polyalkylene oxide or polyalkylene sulfide group. Suitable polyalkylene oxide and polyalkylene sulfide groups are of formula —$(C_{2-4}$ alkyl-het$)_n$- wherein het is O or S and n is, for example, from 1 to 10, e.g. from 1 to 6. Preferably the -spacer- group is an alkylene or -alkylene-aryl-alkylene- group, where each alkylene is the same or different and is typically a $C_{1-10}$ alkylene, preferably $C_{1-6}$ alkylene, and the aryl moiety is typically a $C_{6-10}$ aryl moiety. More preferably, -spacer- is an alkylene or -alkylene-phenyl-alkylene- group, where each alkylene is the same or different and is methylene or ethylene. Most preferred -spacer- groups are methylene and 4-ethylenebenzyl. $R^P$ is preferably a (meth) acrylate, vinylbenzyl (e.g. 3- or 4-vinylbenzyl), (meth)acrylamide, N-vinylamide, vinylene or allyl group, more preferably a (meth)acrylate, vinylbenzyl or (meth)acrylamide group, most preferably a (meth)acrylate or vinylbenzyl group.

Preferred polymerisable groups are those of formula —$R^P$ or -spacer-$R^P$, wherein -spacer- is a $C_{1-6}$ alkylene group or a group —$(C_{1-6}$ alkylene)-$(C_{6-10}$ aryl)-$(C_{1-6}$ alkylene)- and $R^P$ is a (meth)acrylate or vinylbenzyl group.

Fluorophores and fluorescent sensor compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

Formulae (I) and (Ia)

For the fluorophores of formula (I) and fluorophore moieties of formula (Ia), preferred $R^2$ and $R^3$ groups are groups of formula —$SO_2R^6$ wherein $R^6$ represents a chlorine atom or a group of formula —$NR^7R^8$, —$NA^1A^2$, —$NR^7A^1$, $C_{1-6}$ alkyl, $C_{1-6}$ hydroxyalkyl, $C_{2-6}$ alkenyl, $C_{6-10}$ aryl($C_{1-6}$)alkyl, halo($C_{1-6}$)alkyl or —OR' where R' is hydrogen or $C_{1-6}$ alkyl. For example, preferred $R^2$ and $R^3$ groups are groups of formula —$SO_2R^6$ wherein $R^6$ represents a chlorine atom or a group of formula —$NR^7R^8$, —$NA^1A^2$, —$NR^7A^1$, $C_{1-6}$ alkyl, $C_{1-6}$ hydroxyalkyl, $C_{2-6}$ alkenyl, $C_{6-10}$ aryl($C_{1-6}$)alkyl, halo($C_{1-6}$) alkyl or —OR' where R' is $C_{1-6}$ alkyl. More preferred groups are groups of formula —$SO_2R^6$ wherein $R^6$ represents a chlorine atom or a group of formula —$NR^7R^8$, —$NA^1A^2$, —$NR^7A^1$, $C_{1-6}$ alkyl or $C_{1-6}$ hydroxyalkyl. More preferable still are groups of formula —$SO_2R^6$ wherein $R^6$ represents a chlorine atom or a group of formula —$NR^7R^8$, —$NA^1A^2$ or —$NR^7A^1$, more preferably groups of formula —$SO_2R^6$ wherein $R^6$ represents a group of formula —$NR^7R^8$. In a preferred embodiment of the invention, therefore, at least one of $R^2$ and $R^3$, preferably both $R^2$ and $R^3$, represents a group of formula —$SO_2R^6$.

For the fluorophores of formula (I) and fluorophore moieties of formula (Ia), preferably $R^7$ and $R^8$ are the same or different and represent a hydrogen atom or a $C_{1-4}$ alkyl group. The alkyl groups and moieties in $R^7$ and $R^8$ are preferably unsubstituted or substituted by 1 or 2 groups selected from halogen atoms and $C_{1-2}$ alkoxy, hydroxyl, —OSiR'R''R''', —SR' and —NR'R'' groups where R', R'' and R''' are the same or different and represent hydrogen or unsubstituted $C_{1-4}$ alkyl. More preferably R', R'' and R''' are the same or different and represent hydrogen or unsubstituted $C_{1-2}$ alkyl.

More preferably the alkyl groups and moieties in $R^7$ and $R^8$ are unsubstituted or substituted by hydroxyl, —OSiR'R''R''' or —NR'R'' where R', R'' and R''' are the same or different and represent hydrogen or unsubstituted $C_{1-2}$ alkyl. For example, suitable $R^7$ and $R^8$ groups include unsubstituted $C_{1-4}$ alkyl groups such as methyl and isobutyl groups (more preferably isobutyl groups), and substituted $C_{1-4}$ alkyl groups such as —$CH_2CH_2OSi(CH_3)_2C(CH_3)_3$ and 2-hydroxyethyl (—$CH_2CH_2OH$). Most preferably $R^7$ and $R^8$ are the same. Preferably both $R^7$ and $R^8$ are isobutyl groups.

In addition to the substituents discussed above, the alkyl groups and moieties in $R^7$ and $R^8$ may also bear one or more, for example one or two, ionic water-solubilising groups, with possible ionic water-solubilising groups being defined earlier. In an embodiment of the invention, $R^7$ and $R^8$ are not substituted with any ionic water-solubilising groups.

The alkyl groups and moieties in $R^7$ and $R^8$ may alternatively or additionally bear one or more, for example one or two, polymerisable groups, with suitable polymerisable groups being defined earlier. Preferred polymerisable groups include (meth)acrylate, (meth)acrylamide, vinylbenzyl and N-vinylamide.

For the fluorophores of formula (I) and fluorophore moieties of formula (Ia), the $A^1$ and $A^2$ groups are unsubstituted or substituted with suitable groups being described earlier. Preferred substituents include halogen atoms, and $C_{1-2}$ alkyl, $C_{1-2}$ alkoxy, hydroxyl, $C_{1-4}$ hydroxyalkyl and —NR'R'' groups wherein each R' and R'' is the same or different and represents hydrogen or unsubstituted $C_{1-2}$ alkyl. Preferably $A^1$ and $A^2$ represent phenyl groups. More preferably $A^1$ and $A^2$ are unsubstituted.

In addition to the substituents discussed above, the phenyl and heteroaryl groups of $A^1$ and $A^2$ may bear one or more ionic water-solubilising groups or may themselves be a cyclic ionic water-solubilising group. Suitable ionic water-solubilising groups are as defined above for $R^7$ and $R^8$. In one embodiment, $A^1$ and $A^2$ are not substituted, nor represent, an ionic water-solubilising group.

The phenyl and heteroaryl groups of $A^1$ and $A^2$ may alternatively or additionally bear one or more, for example one or two, polymerisable groups, with suitable polymerisable groups being defined earlier.

For fluorophores of formula (I) and fluorophore moieties of formula (Ia), $R^1$ preferably represents a hydrogen or halogen atom or a group —SO$_2$R$^6$ where $R^6$ is as defined for $R^2$ and $R^3$, or $R^1$ represents a group $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, $C_{1-4}$ hydroxyalkyl, —SR' or —NR'R" where R', R" and R''' are the same or different and represent hydrogen or unsubstituted $C_{1-2}$ alkyl, or $R^1$ represents a polymerisable group.

In one embodiment $R^1$ is not a halogen atom.

In one embodiment $R^1$ represents a group $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, $C_{1-4}$ hydroxyalkyl or —NR'R" groups where R', R" and R''' are the same or different and represent hydrogen or unsubstituted $C_{1-2}$ alkyl. In this embodiment, preferably $R^1$ represents a group $C_{1-4}$ alkyl, $C_{1-4}$ alkoxy, $C_{1-4}$ haloalkyl, hydroxyl, cyano, nitro, $C_{1-4}$ hydroxyalkyl, —SR' or —NR'R" where R', R" and R''' are the same or different and represent hydrogen or unsubstituted $C_{1-2}$ alkyl.

In a more preferred embodiment, $R^1$ represents a hydrogen or halogen atom, a group —SO$_2$R$^6$ or a polymerisable group. Preferred polymerisable groups are defined earlier.

For the fluorophores of formula (I) most preferably $R^1$ represents hydrogen. When incorporated into the fluorescent sensor compounds of the invention, preferably $R^1$ represents hydrogen or —SO$_2$R$^6$ where $R^6$ is as defined above for $R^2$ and $R^3$. More preferably, when incorporated into the fluorescent sensor compounds of the invention, $R^1$ represents hydrogen.

Preferably one of $R^1$, $R^2$ and $R^3$ is hydrogen or a group other than —SO$_2$R$^6$. Further, it is preferred that at least one of $R^1$, $R^2$ and $R^3$ represents —SO$_2$R$^6$. More preferably only one of $R^1$, $R^2$ and $R^3$ is hydrogen or a group other than —SO$_2$R$^6$ (i.e. at least two of $R^1$, $R^2$ and $R^3$ represent —SO$_2$R$^6$). More preferably $R^1$ is hydrogen or a group other than —SO$_2$R$^6$ and $R^2$ and $R^3$ are other than hydrogen, more preferably still $R^1$ is hydrogen or a group other than —SO$_2$R$^6$ and $R^2$ and $R^3$ are both groups of formula —SO$_2$R$^6$. Preferably $R^2$ and $R^3$ are the same and represent —SO$_2$R$^6$.

For the fluorophores of formula (I), preferably $R^4$ and $R^5$ are the same or different and represent hydrogen or $C_{1-4}$ alkyl. More preferably $R^4$ and $R^5$ are the same or different and represent hydrogen, methyl or ethyl. More preferably $R^4$ is hydrogen and $R^5$ is hydrogen or methyl.

For fluorophore moieties of formula (Ia), where no $R^4$ group is present, preferably $R^5$ represents hydrogen or $C_{1-4}$ alkyl. More preferably $R^5$ represents hydrogen, methyl or ethyl, more preferably $R^5$ represents hydrogen or methyl.

The pyrene ring of formulae (I) and (Ia) may optionally bear one or more ionic water solubilising groups and/or one or more polymerisable groups in addition to the substituents described above. These water solubilising groups and polymerisable groups may therefore replace any hydrogen atom on the pyrene ring. In one embodiment, where $R^1$, $R^2$ and/or $R^3$ represent hydrogen, one or more of these hydrogen atoms is optionally replaced by an ionic water solubilising group or a polymerisable group. Preferred polymerisable groups and ionic water solubilising groups are described earlier.

In a preferred embodiment, in the fluorophore of formula (I) or the fluorophore moiety or formula (Ia):
$R^2$ and $R^3$ are the same or different and each represent a group —SO$_2$R$^6$ wherein $R^6$ represents a chlorine atom or a group of formula —NR$^7$R$^8$, —NA$^1$A$^2$ or —NR$^7$A$^1$;
$R^1$ represents hydrogen or a polymerisable group;
$R^7$ and $R^8$ are the same or different and represent a hydrogen atom or a $C_{1-4}$ alkyl group, wherein the alkyl group is unsubstituted or substituted with one or two substituents selected from hydroxyl, —OSiR'R"R''', —NR'R", (meth)acrylate, (meth)acrylamide, vinylbenzyl, N-vinylamide and ionic water-solubilising groups, where R', R" and R''' are the same or different and represent hydrogen or unsubstituted $C_{1-4}$ alkyl;
$A^1$ and $A^2$ are the same or different and represent a phenyl or 5- to 6-membered heteroaryl group, wherein $A^1$ and $A^2$ are unsubstituted or substituted with one or more substituents selected from hydroxyl, $C_{1-4}$hydroxyalkyl, —NR'R", polymerisable groups and ionic water-solubilising groups, where R' and R" are the same or different and represent hydrogen or unsubstituted $C_{1-2}$ alkyl;
$R^5$ represents hydrogen or methyl; and
$R^4$, where present, represents hydrogen;
wherein the pyrene ring may optionally bear one or more polymerisable groups and/or one or more ionic water solubilising substituents;
wherein an ionic water-solubilising group is selected from sulfonic acid, phosphonic acid, phosphonium, ammonium and carboxylate salts, phenyl groups substituted with a sulfonic acid, phosphonic acid, phosphonium, ammonium or carboxylate salt, and pyridinium and imidazolium salts; and a polymerisable group is a group of formula —R$^P$ or -spacer-R$^P$, wherein spacer is a $C_{1-6}$ methylene group or a polyethylene oxide or polyethylene thiol group and R$^P$ is a (meth)acrylate, (meth)acrylamide, vinylbenzyl or N-vinylamide group.

In a more preferred embodiment, the fluorophore of formula (I) is selected from:
6-amino-N1,N1,N3,N3-tetraisobutylpyrene-1,3-disulfonamide;
6-amino-N1,N1,N3,N3-tetrakis(2-hydroxyethyl)pyrene-1,3-disulfonamide;
6-amino-N1,N1,N3,N3-tetrakis(2-(tert-butyldimethylsilyloxy)ethyl)pyrene-1,3-disulfonamide;
6-aminopyrene-1,3-disulfonyl dichloride;
6-(methylamino)pyrene-1,3-disulfonyl dichloride;
N1,N1,N3,N3-tetraisobutyl-6-(methylamino)pyrene-1,3-disulfonamide;
N1,N1,N3,N3-tetrakis(2-hydroxyethyl)-6-(methylamino) pyrene-1,3-disulfonamide; and
N1,N1,N3,N3-tetrakis(2-(tert-butyldimethylsilyloxy)ethyl)-6-(methylamino)pyrene-1,3-disulfonamide.

More preferably the fluorophore of formula (I) is:
6-amino-N1,N1,N3,N3-tetraisobutylpyrene-1,3-disulfonamide;
6-amino-N1,N1,N3,N3-tetrakis(2-hydroxyethyl)pyrene-1,3-disulfonamide;
6-(methylamino)pyrene-1,3-disulfonyl dichloride; or
N1,N1,N3,N3-tetrakis(2-hydroxyethyl)-6-(methylamino) pyrene-1,3-disulfonamide.

Fluorophores of Formula (II) and Fluorophore Moieties of Formula (IIa)

Effectively the fluorophore moiety of formula (IIa) is equivalent to the fluorophore of formula (II) excluding the $R^1$ group. The fluorophore moiety can thus bond to the rest of the fluorescent sensor compound via the carbon atom shown bearing the "—$R^{1'}$—" group. The group denoted "—$R^{1'}$—" simply represents the point of attachment of the fluorophore moiety to the rest of the fluorescent sensor compound. The —$R^{1'}$— group can attach to the anthracenyl moiety of the central anthraimide core at any vacant position. However, it is preferably attached to the C10 ring position of the anthraimide core.

For fluorophores of formula (II) and fluorophore moieties of formula (IIa), R is preferably selected from $C_{6-10}$ aryl, 5- to 6-membered heteroaryl, $C_{3-7}$ carbocyclyl, 5- to 6-membered heterocyclyl, $C_{1-6}$ alkyl, $C_{1-6}$ alkoxy, —$C_{1-10}$ alkyl-$SR^7$ (where $R^7$ represents hydrogen or $C_{1-6}$ alkyl), $C_{1-6}$ haloalkyl, $C_{1-6}$ haloalkoxy, $C_{1-10}$ hydroxyalkyl, and —$NR^8R^9$ where $R^8$ and $R^9$ are the same or different and represent hydrogen or $C_{1-4}$ alkyl. More preferably $R^8$ and $R^9$ are the same or different and represent hydrogen or $C_{1-2}$ alkyl, most preferably hydrogen.

More preferably R represents a $C_{1-6}$ alkyl group which is unsubstituted or substituted with 1, 2 or 3 unsubstituted substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, $C_{1-4}$ hydroxyalkyl, —OSiR'R"R''', —SR' and —NR'R" groups where R', R" and R''' are the same or different and represent hydrogen or unsubstituted $C_{1-4}$ alkyl. More preferably R represents a $C_{1-6}$ alkyl group which is substituted with a $C_{1-4}$ alkoxy group. Most preferably R represents a $C_{1-4}$ alkyl group, for example an ethyl group, which is substituted with a $C_{1-2}$ alkoxy group such as a methoxy group.

As discussed earlier, R may optionally bear one or more polymerisable groups and/or one or more ionic water-solubilising groups or the aryl and heteroaryl groups and moieties of R can themselves be a cyclic ionic water-solubilising substituent. Further, the phenyl groups in the anthracenyl moiety of formulae (II) and (IIa) may optionally bear one or more polymerisable groups and/or one or more ionic water-solubilising groups. Preferred polymerisable groups and ionic water-solubilising groups are described earlier.

For the fluorophores of formula (II), two of a, b and c are zero and the other one of a, b and c is one. If a is 1 and $R^1$ is therefore on the left-hand ring as represented in formula (II), then preferably $R^1$ is present at the 5 position, with the backbone of the molecule being numbered as follows:

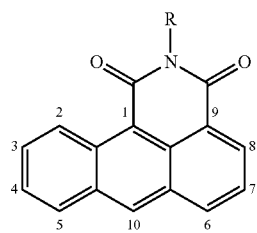

If c is 1 and $R^1$ is therefore on the right-hand ring, then preferably $R^1$ is present at the 6 position, with the molecule being numbered as above.

Most preferably b is 1 and a and c are zero (i.e. the $R^1$ group is present at the 10 position).

Similarly, for the fluorophore moieties of formula (IIa), two of a, b and c are zero and the other one of a, b and c is one. If a is 1 and —$R^{1'}$— is therefore on the left-hand ring as represented in formula (IIa), then preferably —$R^{1'}$— is present at the 5 position, with the backbone of the molecule being numbered as above. If c is 1 and —$R^{1'}$— is therefore on the right-hand ring, then preferably —$R^{1'}$— is present at the 6 position, with the molecule being numbered as above. Most preferably for fluorophore moieties of formula (IIa) b is 1 and a and c are zero (i.e. the fluorophore moiety bonds to the rest of the fluorescent sensor compound via the 10 position).

As mentioned above, $R^1$ is a group which is capable of reacting with another compound comprising a receptor moiety for an analyte in order to prepare a fluorescent sensor compound. In effect, $R^1$ is a "functionalisable" moiety that can be used to tether the fluorophore to the rest of the fluorescent sensor compound. The person skilled in the art will appreciate that there is a vast array of suitable groups which can fulfil this criterion. For example, any suitable reactive functionality which can be used to form a new carbon-carbon, carbon-nitrogen, carbon-oxygen or carbon-sulfur bond by any suitable reaction, for example substitution or addition, would be appropriate.

The following examples of suitable $R^1$ groups are intended to be exemplary only, giving the skilled person some suitable examples which can be used, and are not intended to be an exhaustive list of all possibilities. Exemplary $R^1$ groups include groups of formula -$Alk^1$-$X^1$, -$Alk^2$-$X^2$, —CH=$CR^{12}R^{13}$ or boronic acid groups. In accordance with this embodiment:

$Alk^1$ represents a $C_{1-10}$ alkylene group;

$X^1$ represents a group of formula —$OSO_2Me$ (i.e. mesylate), —$OSO_2PhMe$ (i.e. tosylate) or —$P^+Ph_3$ (phosphorus ylide precursor);

$Alk^2$ represents a bond or a $C_{1-10}$ alkylene group;

$X^2$ represents a halogen atom, a 3-membered heterocyclyl group, or a group of formula:

—$SR^{14}$ where $R^{14}$ represents hydrogen or $C_{1-4}$ alkyl,

—$NR^{15}R^{16}$ where $R^{15}$ and $R^{16}$ are the same or different and represent hydrogen, $C_{1-6}$ alkyl, $C_{6-10}$ aryl, 5- to 10-membered heteroaryl or 5- to 10-membered heterocyclyl, —$COR^{17}$ where $R^{17}$ represents a hydrogen or halogen atom or a $C_{1-6}$ alkyl, $C_{6-10}$ aryl, 5- to 10-membered heteroaryl, 5- to 10-membered heterocyclyl, hydroxy, $C_{1-6}$ alkoxy, $C_{6-10}$ aryloxy, (5- to 10-membered heteroaryl)oxy or (5- to 10-membered heterocyclyl)oxy group;

—CO—$CR^{18}$=$CR^{19}R^{20}$ where $R^{18}$, $R^{19}$ and $R^{20}$ are the same or different and represent a hydrogen atom or a $C_{1-6}$ alkyl group;

—N=C=$X^3$ where $X^3$ represents oxygen or sulphur;

—X—CO—C(=$CH_2$)$R^{22}$ where $R^{22}$ represents a hydrogen atom or a $C_{1-6}$ alkyl, $C_{6-10}$ aryl, 5- to 10-membered heteroaryl or 5- to 10-membered heterocyclyl group; and $R^{12}$ and $R^{13}$ are the same or different and represent a hydrogen or halogen atom, a $C_{1-6}$ alkyl, $C_{6-10}$ aryl, 5- to 10-membered heteroaryl, 5- to 10-membered heterocyclyl or —NR'R" group where R' and R" are the same or different and represent hydrogen or unsubstituted $C_{1-4}$ alkyl.

Suitable boronic acid moieties include groups having the following formulae:

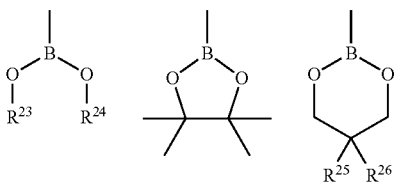

$R^{23}$ and $R^{24}$ are the same or different and preferably represent a hydrogen atom or a $C_{1-6}$ alkyl group. $R^{25}$ and $R^{26}$ are the same or different and preferably represent a hydrogen atom or a $C_{1-6}$ alkyl group.

Suitable 3-membered heterocyclyl groups include oxirane and thiirane.

Preferred $R^1$ groups include groups of formula -$Alk^1$-$X^1$, -$Alk^2$-$X^2$ and —CH=$CR^{12}R^{13}$ wherein:
$Alk^1$ represents a $C_{1-6}$ alkylene group;
$X^1$ represents a group of formula —$OSO_2$Me or —$OSO_2$PhMe;
$Alk^2$ represents a bond or a $C_{1-6}$ alkylene group;
$X^2$ represents a halogen atom or a group of formula:
—$NR^{15}R^{16}$ where $R^{15}$ and $R^{16}$ are the same or different and represent hydrogen, $C_{1-4}$ alkyl, phenyl or 5- to 6-membered heteroaryl;
—$COR^{17}$ where $R^{17}$ represents a hydrogen or halogen atom or a $C_{1-6}$ alkyl, $C_{6-10}$ aryl, 5- to 10-membered heteroaryl, 5- to 10-membered heterocyclyl, hydroxy, $C_{1-6}$ alkoxy, $C_{6-10}$ aryloxy, (5- to 10-membered heteroaryl)oxy or (5- to 10-membered heterocyclyl)oxy group; and
$R^{12}$ and $R^{13}$ are the same or different and represent a hydrogen or halogen atom, or a $C_{1-6}$ alkyl, phenyl, 5- to 6-membered heteroaryl group or a —NR'R" group where R' and R" are the same or different and represent hydrogen or $C_{1-4}$ alkyl.

Preferably $Alk^1$ is a $C_{1-6}$ alkylene group, more preferably a $C_{1-2}$ alkylene group, most preferably $Alk^1$ is a methylene group. Preferably $Alk^1$ is unsubstituted. Preferably $Alk^2$ is a bond or a $C_{1-6}$ alkylene group, more preferably a bond or a $C_{1-2}$ alkylene group, more preferably a bond or a methylene group. Most preferably $Alk^2$ is a methylene group. Preferably $Alk^2$ is unsubstituted.

In one embodiment it is preferred that the $R^1$ group contains a methylene group as the point of attachment to the anthraimide core. Thus, preferred $R^1$ groups include those of formula -$Alk^1$-$X^1$ and -$Alk^2$-$X^2$ where $Alk^1$, $X^1$, $Alk^2$ and $X^2$ are as defined earlier but with the proviso that $Alk^2$ is not zero.

In an alternative embodiment particularly preferred $R^1$ groups include groups of formula —$COR^{17}$ where $R^{17}$ represents a hydrogen or halogen atom or a $C_{1-6}$ alkyl, $C_{6-10}$ aryl, 5- to 10-membered heteroaryl, 5- to 10-membered heterocyclyl, hydroxy, $C_{1-6}$ alkoxy, $C_{6-10}$ aryloxy, (5- to 10-membered heteroaryl)oxy or (5- to 10-membered heterocyclyl)oxy group. More preferably $R^{17}$ represents a hydrogen or halogen atom or a $C_{1-6}$ alkyl, phenyl, hydroxy, $C_{1-6}$ alkoxy or phenyloxy group. Still more preferably $R^{17}$ represents a hydrogen atom or a hydroxy, $C_{1-6}$ alkoxy or phenyloxy group. Most preferably $R^{17}$ represents a hydrogen atom.

It is possible for the phenyl groups in the anthracenyl moiety of formulae (II) and (IIa) to be optionally further substituted by one or more additional substituents (i.e. additional to the $R^1$ and $R^{1'}$ groups). Suitable substituents include those discussed earlier as suitable aryl substituents, for example halogen atoms, and $C_{6-10}$ aryl, $C_{1-6}$ alkyl, $C_{1-6}$ alkoxy, $C_{1-6}$ haloalkyl, $C_{1-6}$ haloalkoxy, hydroxyl, $C_{1-6}$ hydroxyalkyl, —$SR^4$—$SiR^4R^5R^6$, —$NR^4R^5$ and —$N^+R^4R^5R^6$ groups wherein each $R^4$, $R^5$ and $R^6$ is the same or different and represents hydrogen or unsubstituted $C_{1-2}$ alkyl, and substituents of formula —COOH, —$COOR^A$, —COH, —$COR^A$, —$SOR^A$, —$SO_2R^A$, —$SO_3^-$, —$CONH_2$, —$SO_2NH_2$, —$CONHR^A$, —$SO_2NHR^A$, —$CONR^AR^B$ and —$SO_2NR^AR^B$, wherein $R^A$ and $R^B$ are the same or different and represent unsubstituted $C_{1-6}$ alkyl, $C_{3-7}$ carbocyclyl, phenyl or a 5- to 6-membered heteroaryl, or $R^A$ and $R^B$ when attached to the same nitrogen atom form a 5- or 6-membered heterocyclyl group. Other suitable substituents on the phenyl groups of the anthracenyl moiety of formulae (II) and (IIa) include phosphines, phosphine oxide, phosphinate, phosphinamide, phosphonate and phosphonamide, as well as polymerisable groups and ionic water-solubilising groups as described earlier.

In one embodiment of the invention, the fluorophore of formula (II) is represented by formula (II'):

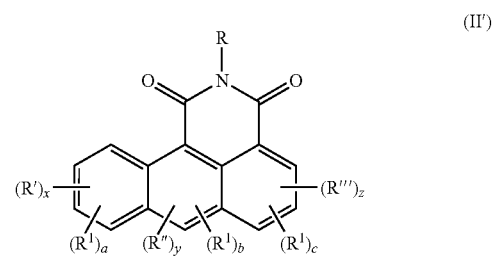

(II')

In this embodiment the variables are as defined above and additionally:
x is zero or an integer of from 1 to 4;
y is zero or 1, with the proviso that when b is 1, y is zero;
z is zero or an integer of from 1 to 3;
R', R" and R''', when present, are the same or different and are selected from:
halogen atoms, and cyano, nitro, thiocyanate, $C_{6-10}$ aryl, $C_{1-6}$ alkyl, $C_{1-6}$ alkoxy, $C_{2-6}$ alkenyl, $C_{2-6}$ alkenyloxy, $C_{1-6}$ haloalkyl, $C_{2-6}$ haloalkenyl, $C_{1-6}$ haloalkoxy, $C_{2-6}$ haloalkenyloxy, hydroxyl, $C_{1-6}$ hydroxyalkyl, phosphonium salts, phosphines, phosphine oxide, phosphinate, phosphinamide, phosphonite, phosphonate and phosphonamide, —COH, —COCl, —$CH_2OR$, —$CH_2NHR$, —OR, —NHR, —$SR^4$, —$SiR^4R^5R^6$, —$NR^4R^5$ and —$N^+R^4R^5R^6$ groups wherein R is (meth)acryl, —CO—C($CH_2$)—$CH_3$ or —$CH_2$-Ph-$CH_2$=$CH_2$ and each $R^4$, $R^5$ and $R^6$ is the same or different and represents hydrogen or unsubstituted $C_{1-2}$ alkyl;
a group —$SO_2R^E$ where $R^E$ is selected from —$NR^FR^G$, —$NA^3A^4$, —$NR^FA^3$, —$OR^F$ and —$OA^3$, where $R^F$ and $R^G$ are the same or different and represent a hydrogen atom or a group selected from $C_{1-10}$ alkyl, $C_{2-10}$ alkenyl, $C_{1-10}$ haloalkyl, $C_{2-10}$ haloalkyl or $C_{1-10}$ hydroxyalkyl, and where $A^3$ and $A^4$ are the same or different and represent a phenyl or 5- to 6-membered heteroaryl group;
substituents of formula —$COR^A$, —$COR^A$, —$SO_3^{2-}$, —$CONH_2$, —$CONHR^A$, —$CONR^AR^B$, —$OCONH_2$, —$OCONHR^A$, —$OCONR^AR^B$, —$NHCOR^A$, —$NR^BCOR^A$, —$NHCOOR^A$, —$NR^BCOOR^A$, —$NHSO_2R^A$, —$NR^BSO_2R^A$, —$NHCONHR^B$, —$NR^ACONHR^B$, —$NHCONR^AR^B$ or —$NR^ACONR^AR^B$ wherein $R^A$ and $R^B$ are the same or different and represent unsubstituted $C_{1-6}$ alkyl, $C_{3-7}$ carbocyclyl, phenyl or a 5- to 6-membered heteroaryl, or $R^A$ and $R^B$ when attached to the same nitrogen atom form a 5- or 6-membered heterocyclyl group;

a group —COO⁻ or —COOR where R represents hydrogen, $C_{1-6}$ alkyl, $C_{3-7}$ carbocyclyl, $C_{6-10}$ aryl, 5- to 10-membered heteroaryl or 5- to 10-membered heterocyclyl;

a group of formula (A):

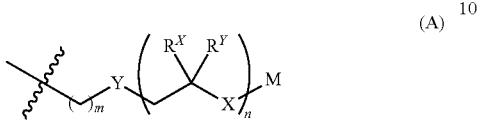

(A)

where m is 0 or 1, X and Y are the same or different and represent —O—, —S— or —NR— where R is hydrogen or $C_{1-4}$ alkyl, n is an integer of from 1 to 20, $R^X$ and $R^Y$ are the same or different and represent hydrogen, $C_{1-6}$ alkyl, $C_{6-10}$ aryl, 5- to 10-membered heteroaryl or 5- to 10-membered heterocyclyl, and M represents hydrogen, (meth)acryl or 4-vinylbenzyl, and wherein the alkyl, carbocyclyl, heterocyclyl, phenyl and heteroaryl groups or moieties in the R', R'' and R''' groups discussed above, for example in the $R^A$ and $R^B$ groups etc., optionally or alternatively bear one or more (for example one) polymerisable group and/or one or more (for example one) ionic water-solubilising group as defined earlier, or the phenyl and heteroaryl groups and moieties are themselves a cyclic ionic water-solubilising substituent as defined earlier. Preferred polymerisable groups and ionic water-solubilising groups are defined earlier.

In one embodiment of the invention, the fluorophore moiety of formula (IIa) is represented by formula (IIa'):

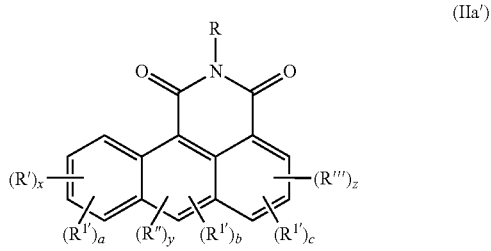

(IIa')

In this embodiment the variables are as defined above and additionally:

x is zero or an integer of from 1 to 4;
y is zero or 1, with the proviso that when b is 1, y is zero;
z is zero or an integer of from 1 to 3;
R', R'' and R''', when present, are the same or different and are selected from:
halogen atoms, and cyano, nitro, thiocyanate, $C_{6-10}$ aryl, $C_{1-6}$ alkyl, $C_{1-6}$ alkoxy, $C_{2-6}$ alkenyl, $C_{2-6}$ alkenyloxy, $C_{1-6}$ haloalkyl, $C_{2-6}$ haloalkenyl, $C_{1-6}$ haloalkoxy, $C_{2-6}$ haloalkenyloxy, hydroxyl, $C_{1-6}$ hydroxyalkyl, phosphonium salts, phosphines, phosphine oxide, phosphinate, phosphinamide, phosphonite, phosphonate and phosphonamide, —COH, —COCl, —CH$_2$OR, —CH$_2$NHR, —OR, —NHR, —SR$^4$, —SiR$^4$R$^5$R$^6$, —NR$^4$R$^5$ and —N$^+$R$^4$R$^5$R$^6$ groups wherein R is (meth)acryl, —CO—C(CH$_2$)—CH$_3$ or —CH$_2$-Ph-CH$_2$═CH$_2$ and each $R^4$, $R^5$ and $R^6$ is the same or different and represents hydrogen or unsubstituted $C_{1-2}$ alkyl;

a group —SO$_2$R$^E$ where $R^E$ is selected from —NR$^F$R$^G$, —NA$^3$A$^4$, —NR$^F$A$^3$, —OR$^F$ and —OA$^3$, where $R^F$ and $R^G$ are the same or different and represent a hydrogen atom or a group selected from $C_{1-10}$ alkyl, $C_{2-10}$ alkenyl, $C_{1-10}$ haloalkyl, $C_{2-10}$ haloalkyl or $C_{1-10}$ hydroxyalkyl, and where $A^3$ and $A^4$ are the same or different and represent a phenyl or 5- to 6-membered heteroaryl group;

substituents of formula —COR$^A$, —COR$^A$, —SO$_3^{2-}$, —CONH$_2$, —CONHR$^A$, —CONR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NHSO$_2$R$^A$, —NR$^B$SO$_2$R$^A$, —NHCONHR$^B$, —NR$^A$CONHR$^B$, —NHCONR$^A$R$^B$ or —NR$^A$CONR$^A$R$^B$ wherein $R^A$ and $R^B$ are the same or different and represent unsubstituted $C_{1-6}$ alkyl, $C_{3-7}$ carbocyclyl, phenyl or a 5- to 6-membered heteroaryl, or $R^A$ and $R^B$ when attached to the same nitrogen atom form a 5- or 6-membered heterocyclyl group;

a group —COO⁻ or —COOR where R represents hydrogen, $C_{1-6}$ alkyl, $C_{3-7}$ carbocyclyl, $C_{6-10}$ aryl, 5- to 10-membered heteroaryl or 5- to 10-membered heterocyclyl;

a group of formula (A):

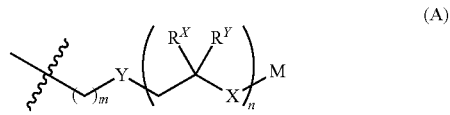

(A)

where m is 0 or 1, X and Y are the same or different and represent —O—, —S— or —NR— where R is hydrogen or $C_{1-4}$ alkyl, n is an integer of from 1 to 20, $R^X$ and $R^Y$ are the same or different and represent hydrogen, $C_{1-6}$ alkyl, $C_{6-10}$ aryl, 5- to 10-membered heteroaryl or 5- to 10-membered heterocyclyl, and M represents hydrogen, (meth)acryl or 4-vinylbenzene, and wherein the alkyl, carbocyclyl, heterocyclyl, phenyl and heteroaryl groups or moieties in the R', R'' and R''' groups discussed above, for example in the $R^A$ and $R^B$ groups etc., optionally or alternatively bear one or more (for example one) polymerisable group and/or one or more (for example one) ionic water-solubilising group as defined earlier, or the phenyl and heteroaryl groups and moieties are themselves a cyclic ionic water-solubilising substituent as defined earlier. Preferred polymerisable groups and ionic water-solubilising groups are defined earlier.

In a preferred embodiment of formulae (II') and (IIa'),
x is zero, 1 or 2;
y is zero or 1, with the proviso that when b is 1, y is zero;
z is zero or 1;
R', R'' and R''', when present, are the same or different and are selected from:
halogen atoms, and cyano, nitro, thiocyanate, $C_{6-10}$ aryl, $C_{1-6}$ alkyl, $C_{1-6}$ alkoxy, $C_{2-6}$ alkenyl, $C_{2-6}$ alkenyloxy, $C_{1-6}$ haloalkyl, $C_{2-6}$ haloalkenyl, $C_{1-6}$ haloalkoxy, $C_{2-6}$ haloalkenyloxy, hydroxyl, $C_{1-6}$ hydroxyalkyl, phosphonium salts, phosphines, phosphine oxide, phosphinate, phosphinamide, phosphonite, phosphonate and phosphonamide, —COH, —COCl, —CH$_2$OR, —CH$_2$NHR, —OR, —NHR, —SR$^4$, —SiR$^4$R$^5$R$^6$, —NR$^4$R$^5$ and —N$^+$R$^4$R$^5$R$^6$ groups wherein R is (meth)acryl, —CO—C(CH$_2$)—CH$_3$ or —CH$_2$-Ph-CH$_2$=CH$_2$ and each R$^4$, R$^5$ and R$^6$ is the same or different and represents hydrogen or unsubstituted C$_{1-2}$ alkyl;

a group —SO$_2$R$^E$ where R$^E$ is selected from —NR$^F$R$^G$, —NA$^3$A$^4$, —NR$^F$A$^3$, —OR$^F$ and —OA$^3$, where R$^F$ and R$^G$ are the same or different and represent a hydrogen atom or a group selected from C$_{1-10}$ alkyl, C$_{2-10}$ alkenyl, C$_{1-10}$ haloalkyl, C$_{2-10}$ haloalkyl or C$_{1-10}$ hydroxyalkyl, and where A$^3$ and A$^4$ are the same or different and represent a phenyl or 5- to 6-membered heteroaryl group;

substituents of formula —COR$^A$, —COR$^A$, —SO$_3^{2-}$, —CONH$_2$, —CONHR$^A$, —CONR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NHSO$_2$R$^A$, —NR$^B$SO$_2$R$^A$, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent unsubstituted C$_{1-6}$ alkyl, C$_{3-7}$ carbocyclyl, phenyl or a 5- to 6-membered heteroaryl, or R$^A$ and R$^B$ when attached to the same nitrogen atom form a 5- or 6-membered heterocyclyl group;

and wherein the alkyl, carbocyclyl, heterocyclyl, phenyl and heteroaryl groups or moieties in the R', R" and R"' groups discussed above, for example in the R$^A$ and R$^B$ groups etc., optionally or alternatively bear one or more (for example one) polymerisable group and/or one or more (for example one) ionic water-solubilising group as defined earlier, or the phenyl and heteroaryl groups and moieties are themselves a cyclic ionic water-solubilising substituent as defined earlier. Preferred polymerisable groups and ionic water-solubilising groups are defined earlier.

In a more preferred embodiment of formula (II') and (IIa'):
x is zero or 1;
y is zero;
z is zero or 1;
R', R" and R"', when present, are the same or different and are selected from halogen atoms, and cyano, nitro, thiocyanate, C$_{6-10}$ aryl, C$_{1-6}$ alkyl, C$_{1-6}$ alkoxy, C$_{2-6}$ alkenyl, C$_{2-6}$ alkenyloxy, C$_{1-6}$ haloalkyl, C$_{2-6}$ haloalkenyl, C$_{1-6}$ haloalkoxy, C$_{2-6}$ haloalkenyloxy, hydroxyl, C$_{1-6}$ hydroxyalkyl, phosphonium salts, phosphines, phosphine oxide, phosphinate, phosphinamide, phosphonite, phosphonate and phosphonamide, —COH, —COCl, —CH$_2$OR, —CH$_2$NHR, —OR, —NHR, —SR$^4$, —SiR$^4$R$^5$R$^6$, —NR$^4$R$^5$ and —N$^+$R$^4$R$^5$R$^6$ groups wherein R is (meth)acryl, —CO—C(CH$_2$)—CH$_3$ or —CH$_2$-Ph-CH$_2$=CH$_2$ and each R$^4$, R$^5$ and R$^6$ is the same or different and represents hydrogen or unsubstituted C$_{1-2}$ alkyl;

and wherein the alkyl, carbocyclyl, heterocyclyl, phenyl and heteroaryl groups or moieties in the R', R" and R"' groups discussed above, for example in the R$^A$ and R$^B$ groups etc., optionally or alternatively bear one or more (for example one) polymerisable group and/or one or more (for example one) ionic water-solubilising group as defined earlier, or the phenyl and heteroaryl groups and moieties are themselves a cyclic ionic water-solubilising substituent as defined earlier. Preferred polymerisable groups and ionic water-solubilising groups are defined earlier.

In a more preferred embodiment of formula (II') and (IIa'):
R represents C$_{1-6}$ alkyl which is unsubstituted or substituted with one or two substituents selected from C$_{1-4}$ alkoxy, hydroxyl, —OSiR'R"R'", —NR'R", (meth)acrylate, (meth)acrylamide, vinylbenzyl, N-vinylamide and ionic water-solubilising groups, where R', R" and R"' are the same or different and represent hydrogen or unsubstituted C$_{1-4}$ alkyl;
x is zero or 1;
y is zero;
z is zero or 1;
R', R" and R"', when present, are the same or different and represent halogen atoms, or cyano, nitro, thiocyanate, C$_{6-10}$ aryl, C$_{1-6}$ alkyl, C$_{1-6}$ alkoxy, C$_{2-6}$ alkenyl, C$_{2-6}$ alkenyloxy, haloalkyl, C$_{2-6}$ haloalkenyl, C$_{1-6}$ haloalkoxy, C$_{2-6}$ haloalkenyloxy, hydroxyl, C$_{1-6}$ hydroxyalkyl, —COH, —COCl, —SR$^4$ and —NR$^4$R$^5$ groups wherein each R$^4$ and R$^5$ is the same or different and represents hydrogen or unsubstituted C$_{1-2}$ alkyl;

and wherein the alkyl, carbocyclyl, heterocyclyl, phenyl and heteroaryl groups or moieties in the R', R" and R"' groups discussed above, for example in the R$^A$ and R$^B$ groups etc., optionally or alternatively bear one or more (for example one) polymerisable group and/or one or more (for example one) ionic water-solubilising group as defined earlier, or the phenyl and heteroaryl groups and moieties are themselves a cyclic ionic water-solubilising substituent as defined earlier. Preferred polymerisable groups and ionic water-solubilising groups are defined earlier with regard to formulae (I) and (Ia).

In one preferred embodiment the phenyl groups in the anthracenyl moiety of formulae (II') and (IIa') are not further substituted, and only bear the —R$^1$ or —R$^{1'}$— group. In an alternative preferred embodiment, the phenyl groups in the anthracenyl moiety of formulae (II') and (IIa') bear one or more (for example one) polymerisable group and/or one or more (for example one) ionic water-solubilising group, as defined earlier.

In a most preferred embodiment, the fluorophore of formula (II) is 10-formyl-N-[2-(methoxy)ethyl]-anthracene-1,9-dicarboxylic imide.

Fluorescent Sensor Compounds

The phrase "fluorescent sensor compound" as used herein is a compound whose optical (fluorescent) properties are altered on binding with an analyte. As described earlier, a fluorescent sensor compound includes a receptor moiety for the analyte and a fluorophore moiety. Typically a single receptor moiety and a single fluorophore moiety are present. The emission wavelength, intensity and/or lifetime of the fluorophore moiety is altered when the analyte is bound to the receptor.

Examples of preferred analytes whose presence can be determined by the fluorescent sensor compounds of the invention include saccharides, amino saccharides and carbonyl saccharides. The fluorescent sensor compounds of the invention can also be used to detect the pH of a substance, or as a potassium or enzyme indicator. A preferred analyte is glucose.

The fluorescent sensor compounds of the invention are based on the fluorophores of formulae (I) and (II). As will be appreciated by a person skilled in the art, in order to form the fluorescent moiety of the fluorescent sensor compound, the fluorophore must form a covalent bond with the rest of the fluorescent sensor compound. Typically, the fluorophore moiety is directly bonded to the receptor moiety or the two moieties are linked via a non-polymeric spacer group, e.g. a C$_{1-6}$ alkylene group.

In the case of a fluorophore of formula (I), the resulting fluorescent sensor compound thus comprises a fluorophore moiety of formula (Ia). Effectively the fluorophore moiety of formula (Ia) is equivalent to the fluorophore of formula (I)

excluding the $R^4$ group. The fluorophore moiety is thus bonded to the rest of the fluorescent sensor compound via the $-NR^5-$ group.

In the case of a fluorophore of formula (II), the resulting fluorescent sensor compound thus comprises a fluorophore moiety of formula (IIa). In this embodiment the fluorophore moiety is linked to a nitrogen atom of the receptor moiety, optionally via a spacer group which is retained following reaction of the $R^1$ group with another compound which comprises the receptor moiety. Suitable spacer groups include, for example, $C_{1-6}$ alkylene groups (for example methylene or ethylene groups, more preferably methylene groups) which may be retained, for example, from the $Alk^1$ or $Alk^2$ groups of the $R^1$ group in the fluorophore of formula (II).

The receptor moiety of the fluorescent sensor compounds of the invention will generally comprise one or more binding groups which are capable of binding to the analyte whose presence is to be determined (the "target analyte"). The binding groups can be any suitable functional group capable of achieving this effect. Exemplary binding groups include boronic acids, crown ethers and aza-crown ethers. In one embodiment, the receptor moiety may act as a quencher of the fluorescence emitted by the fluorophore moiety, the extent of quenching being dependent on whether analyte is bound to the receptor. In a preferred embodiment, the receptor does not act as a quencher but modifies the fluorescent signal when bound to an analyte, for example by altering the fluorescence wavelength, intensity and/or lifetime.

Where more than one binding group is present in the receptor moiety, the groups may be separated by a spacer group. The spacer group is chosen to ensure an appropriate spacing of the binding groups, which in turn ensures acceptable binding of the groups to the relevant analyte of interest. In one embodiment the fluorophore moiety acts as a spacer group between the binding groups of the receptor moiety. In this embodiment the exact nature of the fluorophore moiety will need to be strictly controlled in order to ensure that the binding groups are appropriately spaced in order to interact with the analyte to be sensed.

In an alternative, preferred embodiment, the structure of the receptor moiety itself ensures appropriate spacing of the binding groups of the receptor moiety. In this embodiment the fluorophore moiety does not act as a spacer group between the binding groups. This allows more flexibility in the precise nature of the fluorophore moiety, as its size and shape is no longer critical in ensuring interaction between the binding groups and the target analyte. In this embodiment the binding groups of the receptor moiety are preferably separated by a spacer moiety. Suitable spacer moieties include $C_{1-10}$ alkyl, $C_{6-10}$ aryl, 5- to 10-membered heteroaryl and $C_{3-10}$ carbocyclic groups and combinations thereof. The alkyl portion may be straight or branched, preferably straight. The cyclic groups (in particular the aryl and heteroaryl groups) can be optionally substituted as discussed earlier. For example, one or more ionic water-solubilising groups can be present on these groups. Exemplary spacer groups containing cyclic groups include, but are not limited to:

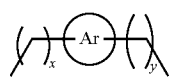

where Ar is an aryl or heteroaryl group, preferably a phenyl or 5- to 6-membered heteroaryl group, more preferably a phenyl group. x and y represent zero or an integer of from 1 to 7. Preferably when x is zero then y is an integer of from 1 to 7. Alternatively, when x is greater than zero, preferably it is an integer of from 1 to 5 and y is also an integer of from 1 to 5. The groups $-(CH_2)_x-$ and $-(CH_2)_y-$ can be attached to any position of the Ar ring. For example, when Ar is phenyl, the groups $-(CH_2)_x-$ and $-(CH_2)_y-$ can be ortho, meta or para to one another.

When the analyte is glucose, preferably the spacer moiety comprises from 4 to 6 carbon atoms, for example a straight chain $C_{4-6}$ alkyl group. More preferably the spacer moiety comprises 6 carbon atoms, for example an n-hexyl group.

In a preferred embodiment the receptor moiety comprises a group of formula (A):

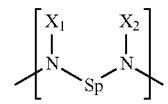

(A)

wherein $X_1$ and $X_2$ are binding groups capable of binding to the analyte whose presence is to be determined, and Sp is a spacer moiety, for example a spacer moiety as defined above. Preferably $X_1$ and $X_2$ are the same or different and represent a group $-(Alk^1)_n-Y_1$ or $-(Alk^1)_n-Y_2$ respectively where $Alk^1$ is a $C_{1-2}$ alkyl group, n is zero or 1, and $Y_1$ and $Y_2$ are the same or different and represent a binding group. Preferably $X_1$ and $X_2$ are the same, n is 1 and $Alk^1$ is a methylene group. Preferably $Y_1$ and $Y_2$ represent groups or formula $-Alk^2-B(OH)_2$ wherein each $Alk^2$ is the same or different and represents a $C_{1-4}$ alkyl, $C_{1-4}$ alkoxy or $C_{6-10}$ aryl group. When $Alk^2$ is an alkyl group, preferably it is a methyl, ethyl, propyl or butyl group. When $Alk^2$ is an alkoxy group, preferably it is a methoxy, ethoxy or butoxy group. When $Alk^2$ is an aryl group, preferably it is a phenyl group. More preferably each $Alk^2$ represents a phenyl group. Accordingly, preferably $Y^1$ and $Y^2$ both represent $-Ph-B(OH)_2$.

In this preferred embodiment the fluorescent sensor compound may comprise a fluorophore moiety which is a radical of a fluorophore of formula (I). In this embodiment the fluorophore moiety is linked to a nitrogen atom of the receptor moiety via the amino group-$NR^5-$ present on the pyrene moiety of the fluorophore. In a preferred embodiment a spacer group is present between the fluorophore moiety and the receptor moiety of formula (A) described above. Preferably this spacer group is a $C_{1-6}$ alkyl group, more preferably a $C_{1-3}$ alkyl group, more preferably a $C_{2-3}$ alkyl group, most preferably an ethylene group. Preferably this spacer group is bonded to the nitrogen atom bearing one of the binding groups $X_1$ and $X_2$ and also to the nitrogen atom of the amine group $-NR^5-$ on the pyrene ring of the fluorophore moiety.

Alternatively, the fluorescent sensor compound may comprise a fluorophore moiety which is a radical of a fluorophore of formula (II). In this embodiment the fluorophore moiety is linked to a nitrogen atom of the receptor moiety, optionally via a spacer group which is retained following reaction of the $R^1$ group with another compound which comprises the receptor moiety. Suitable spacer groups include, for example, $C_{1-6}$ alkyl groups.

In a preferred embodiment the fluorescent sensor compounds of the invention comprise one or more (e.g. one) polymerisable group as described above. The polymerisable group is capable of reacting with or interacting with a support substrate (or precursor thereto) to immobilise the fluorescent sensor compound on or in the support substrate (e.g. a hydrogel). The polymerisable group typically reacts with the support substrate via a free-radical polymerisation reaction. A free-radical polymerisation reaction may be thermally or photochemically induced, preferably it is photochemically induced.

A polymerisable group may be present on the fluorophore moiety and/or on the receptor moiety. In a preferred embodiment, a polymerisable group is present on the receptor moiety. Where the receptor moiety is of formula (A), preferably a polymerisable group is connected to a nitrogen atom of the receptor moiety. More preferably the fluorophore moiety is then connected to the other nitrogen atom of the receptor moiety as described above. In this embodiment, the polymerisable group is preferably of formula -spacer-$R^P$, wherein -spacer- and $R^P$ are as defined above. Spacer is preferably a methylene group.

In an alternative embodiment the fluorescent sensor compound is linked to a support substrate (e.g. a hydrogel).

Preferred fluorescent sensor compounds comprising a fluorophore moiety of formula (Ia) include:
6-[2-([2-(boronic acid)benzyl]-{6-[[2-(boronic acid)benzyl]-(4-vinylbenzyl)amino]hexyl}amino)ethylamino] pyrene-1,3-disulfonic acid bis-diisobutylamide; and
6-{[2-((2-(boronic acid)benzyl)-{6-[(2-(boronic acid)benzyl)-(4-vinyl-benzyl)amino]hexyl}-amino)-ethyl]methylamino}-pyrene-1,3-disulfonic acid bis[bis(2-hydroxyethyl)amide].

Preferred fluorescent sensor compounds comprising a fluorophore moiety of formula (IIa) include:
10-({6-[4-(2-Acryloyloxyethyl)benzyl-(2-{boronic acid}benzyl)-amino]hexyl-(2-{boronic acid}benzyl) amino}methyl)-N-[2-(methoxy)ethyl]-anthracene-1,9-dicarboxylic imide.

Sensors Comprising the Fluorophores and Fluorescent Sensor Compounds

The fluorophores and fluorescent sensor compounds of the present invention are envisaged for use with any fibre optic sensor. Invasive sensors for in vivo use are particularly envisaged, but the present invention is not limited to such sensors. Examples of analytes that can be detected by use of a sensor of the invention include potassium, glucose and other biological or non-biological substances which are currently detected by use of fibre optic devices. In one embodiment of the invention, the fluorescent sensor compound is sensitive to the presence of glucose.

A sensor into which the fluorescent sensor compounds of the invention is incorporated typically comprises an optical fibre having a sensing region in its distal end. The distal end may, for example, be adapted for insertion into a patient, for example insertion into a blood vessel through a cannular. The fluorescent sensor compound is positioned on or in the sensing region of the optical fibre, such that a signal emitted by the compound is transmitted through the optical fibre. For example, the distal end of the fibre may comprise a cell in which the fluorescent sensor compound is contained. The optical fibre typically extends through a cable and terminates in a connector, which is adapted to mate with an appropriate monitor. The monitor typically includes further optical cable that mates with the connector at one end and at the other bifurcates to connect to (a) an appropriate light source for the optical sensor and (b) a detector for the emitted signal.

A sensor of the invention can be manufactured by providing a suitable optical fibre comprising a cell, typically at or near the tip of the fibre. Typically, the cell can be produced by forming one or more holes in or near the tip of the fibre, for example by laser ablation. The fluorescent sensor compound, which may be attached to a support substrate, is inserted into the cell. In the case of a fluorescent sensor compound attached to a support substrate, the support substrate may be dissolved in a suitable solvent to facilitate insertion into the cell. To maintain the fluorescent sensor compound within the cell, any openings in the cell may be covered. One or more openings may be covered with an impermeable material if desired. One or more openings, however, are typically covered with a semi-permeable material to ensure that analyte present in the test substance will be able to enter the cell during use.

The following section describes suitable synthetic schemes which can be used to prepare compounds across the scope of the current claims. They are intended to be indicative of suitable reactants and reactions which can be employed in order to produce a wide range of variants based on the compounds which are later exemplified.

Aminopyrene Synthesis

In the synthesis of the aminopyrenes of formulae (I) and (Ia), sulfonyl chloride groups can be introduced onto the aminopyrene fused-ring system at $R^2$ and $R^3$ by direct electrophilic chlorosulfonation through treatment with neat chlorosulfonic acid at room temperature. The sulfonyl chloride thus formed is a powerful intermediate which can be converted to a sulfonic acid through aqueous hydrolysis, to a sulfonate ester through alcoholysis with R'OH, to sulfonamide derivatives by direct reaction with an appropriately functionalised primary or secondary amine or aniline in the presence of Hunig's base. The sulfonyl chloride can also be treated with alkyl/aryl Grignard reagents to form alkyl/aryls sulfones in an anhydrous, aprotic solvent such as tetrahydrofuran. The $R^1$ ring position can be similarly functionalised by chlorosulfonation to form the sulfonyl chloride which can then be further derivatised using the methods outlined above.

Further functionalisation of the $R^6$ sulfonyl substituent can be achieved by employing an appropriately functionalised precursor. For example through the treatment of the sulfonyl chloride intermediate with a primary or secondary haloalkylamine hydrochloride in the presence of Hunig's base and subsequent substitution of the alkyl halide with hydroxyl via basic hydrolysis; via reaction with sodium hydrosulfide in refluxing ethanol to provide a hydrosulfide; or formation of the primary amine through the Gabriel synthesis (nucleophilic substitution with potassium phthalimide in refluxing tetrahydrofuran to form an alkyl phthalic imide which is then subjected to hydrazinolysis via the Ing-Manske procedure using hydrazine in refluxing ethanol to yield the primary amine). In the case of the $R^6$ alkyl, aryl hydroxyl, thiol, amine groups these can be further functionalised, for example by nucleophilic substitution with 4-vinylbenzyl chloride in the presence of an appropriate base (Hunig's base for amine, thiol and caesium carbonate for alcohol) or by reaction with (meth) acryloyl chloride (for hydroxyl and amine) in the presence of Hunig's base in an aprotic solvent at 0° C. By such methods it is possible to incorporate polymerisable groups such as vinylbenzyl, (meth)acrylate or (meth)acrylamide onto the $R^6$ substituent(s).

The hydroxyl, thiol or amine functionalities on $R^6$ alkyl or aryl groups can be used to introduce a "spacer" poly(alkylene)glycol or poly(alkylene)thioglycol through a nucleophilic ring-opening reaction with an appropriately functionalised oxirane or thiirane in the presence of a base (Hunig's base for amine, thiol and sodium hydride for alcohol) at room temperature. The terminal alcohol or thiol group of the resultant "spacer-chain" can be further functionalised if required, for example by reaction with 4-vinylbenzyl chloride in the presence of Hunig's base for thiol functionalities or by reaction with (meth)acryloyl chloride in the presence of Hunig's base in an aprotic solvent such as tetrahydrofuran at 0° C. for alcohol groups. The terminal alcohol group of a polyethyleneglycol "spacer" chain can be converted to a primary or secondary amine through oxidation of the alcohol to an aldehyde under Swern oxidation conditions (oxalyl chloride, dimethylsulfoxide, triethylamine at −30° C.) and then reductive amination of the aldehyde with ammonia (or primary amine) and sodium borohydride reducing agent. The resultant amine can then be reacted with (meth)acryloyl chloride in the presence of Hunig's base in an aprotic solvent at 0° C. or 4-formylstyrene and sodium borohydride in ethyl alcohol. By such methods it is possible to functionalise $R^1$, $R^2$, $R^3$ sulfonyl chloride functionalities with a "$R^6$-spacer-[polymerisable group]" motif.

Alternative R' substituents are accessible via introduction of a nitro group. This can be directly introduced to the $R^1$ ring position by electrophilic nitration through treatment of the pyrene fluorophore with a mixture of concentrated nitric acid and concentrated sulphuric acid. The resultant nitro group is a powerful synthetic intermediate which can be reduced to a primary amine group by reduction with iron(0) in refluxing acetic acid. The resultant primary amine group can then be further alkylated with appropriately functionalised alkyl tosylates, mesylates or halides to form secondary or tertiary amines or quaternary ammonium salts. Alternatively the primary amine can be converted to a diazonium salt through reaction with nitrous acid (sodium nitrite/hydrochloride acid) which can then be substituted for halide (Cl, Br, I), thioether (SR'), cyano, hydroxyl or ether (OR') using Sandmeyer reaction conditions (ArN≡N$^+$, Cu$^I$X, 60-100° C., where X=Cl, Br, I, SR', CN, OH, OR'). The diazonium salt can also be treated with acetic acid, sulfur dioxide and copper(II) chloride to displace the —N≡N$^+$ group with a sulfonyl chloride (—SO$_2$Cl) group. This sulfonyl chloride functionality can either be hydrolysed with water to the yield a sulfonic acid, subjected to alcoholysis to form a sulfonate ester or reacted with ammonia or alkyl/aryl/heterocyclic primary and secondary amines to form sulfonamide moieties where the alkyl/aryl/heterocyclic substituents can optionally be further functionalised, eg. with polymerisable groups such as (meth)acrylate, (meth)acrylamide or vinylbenzyl or with water solubilising groups such as phosphonate, carboxylate, quaternary ammonium, phosphonium, etc. Alternatively the diazonium salt of the $R^1$ primary amine can be formed under Balz-Schiemann reaction conditions (sodium nitrite, fluoroboric acid) to form the tetrafluoroborate salt of the diazonium cation which on thermal decomposition introduces a fluorine substituent at the $R^1$ position. Sandmeyer conditions can also be used to introduce a thiol —SH group at $R^1$ through reaction of the diazonium salt with potassium thiocyanate in the presence of copper(I) thiocyanate and then reducing the resultant arylthiocyanate with lithium aluminium hydride in tetrahydrofuran at room temperature.

An $R^1$ primary amine group can be reacted with (meth)acryloyl chloride in the presence of Hunig's base in an aprotic solvent such as dichloromethane at 0° C. to introduce a (meth)acrylamide polymerisable group at the $R^1$ ring position. Alternatively the hydroxy group introduced via the Sandmeyer reaction can be similarly treated with (meth)acryloyl chloride in the presence of Hunig's base in an aprotic solvent at 0° C. to place a (meth)acrylate polymerisable group at the $R^1$ ring position. A different approach to introduce a (meth)acrylamide could involve reducing the $R^1$ cyano group, produced under Sandmeyer conditions, with lithium aluminium hydride in either diethyl ether or tetrahydrofuran and reacting the resultant primary "benzylamine" type functionality with (meth)acryloyl chloride in the presence of Hunig's base in an aprotic solvent at 0° C. The "benzylamine" group can also be reductively aminated with 4-formylstyrene and sodium borohydride in ethanol thus introducing a polymerisable vinylbenzene entity at $R^1$.

The $R^1$ halide functionalities introduced by the Sandmeyer reaction are themselves powerful synthetic intermediates. For example, treatment of the $R^1$ arylhalide with magnesium in tetrahydrofuran forms a Grignard reagent which can be employed to formylate the pyrene ring through its reaction with N,N'-dimethylformamide at room temperature. This formyl group can then be reduced to form a benzylalcohol functionality which can be alkylated, for example with 4-vinylbenzyl chloride, or the formyl group can be reductively aminated, for example with 4-vinylbenzylamine and sodium borohydride, which are two methods of introducing a vinylbenzene polymerisable functionality at the $R^1$ position. The benzylalcohol group can also be esterified, for example with (meth)acryloyl chloride in the presence of Hunig's base in an aprotic solvent at 0° C. yielding a (meth)acrylate polymerisable group at the $R^1$ position. The $R^1$ aryl Grignard reagent can also be used to carboxylate the $R^1$ position through its reaction with carbon dioxide. The carboxylate can then be chlorinated through reaction with thionyl chloride to form an arylacid chloride which is a powerful synthetic intermediate which can be reacted with alcohol or amine containing species to form ester and amide linkages respectively.

The $R^1$ halide functionalities can additionally be employed to introduce organophosphorus groups to the $R^1$ position. For example, a phosphine group can be introduced through the cross-coupling of an $R^1$ arylbromide with a secondary phosphine in the presence of palladium(II) acetate and 1,1'-bis (diisopropylphosphino)ferrocene co-catalysts, caesium carbonate base and N,N'-dimethylformamide solvent at 120° C. The resultant tertiary phosphine group can then be further alkylated with an alkyl mesylate in refluxing 1,2-ethylene dichloride to form a phosphonium salt. Alternatively phosphinate [OP(OR)R$_2$], phosphonate [OP(OR)$_2$R] or phosphine oxide [OPR$_3$] groups can be introduced via a proline-promoted copper-catalyzed P-arylation reaction using a $R^1$ aryliodide and an O=PH(R")(R''') reagent (where R", R'''=alkyl, aryl, heterocycle, O-alkyl, O-aryl, O-heterocycle) in the presence of proline, caesium carbonate and a catalytic amount of copper(I) iodide in toluene at 110° C. Phosphonite (P(OR)$_2$R) groups can be introduced through reaction of the $R^1$ halide with magnesium, in tetrahydrofuran, to form a Grigard reagent which can then undergo nucleophilic substitution with an appropriately functionalised dialkyl chlorophosphite or diaryl chlorophosphite.

The primary or secondary pyreneamine can be acylated at $R^4$ or $R^5$ through its reaction with an appropriately functionalised acyl chloride in the presence of Hunig's base in an aprotic solvent at 0° C. This acylamide can then be reduced to an alkyl group through treatment with lithium aluminium hydride in tetrahydrofuran at room temperature. Alternatively the primary or secondary pyreneamine can be mono-alkylated via reductive amination through its treatment with an appropriately functionalised carbonyl compound and sodium triacetoxyborohydride in 1,2-ethylenedichloride. The primary pyreneamine can also be mono-alkylated via the Fukuyama amine synthesis methodology through firstly its reaction with nosyl chloride in the presence of triethylamine in dichloromethane then N-alkylation of the resultant sulfonamide with an appropriately functionalised alcohol using Mitsonubu conditions (R—OH, diethyl azodicarboxylate [DEAD], triphenylphosphine, dichloromethane) and finally deprotection of the nosylate protecting group with thiophenol, potassium carbonate in N,N'-dimethylformamide.

Anthraimide Synthesis

The anthraimide fluorophore can be synthesised in three steps from anthracene as shown in the following reaction scheme:

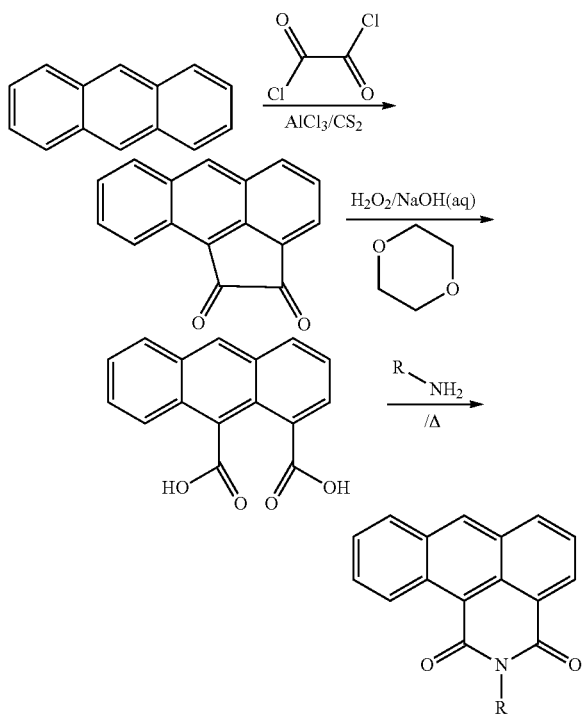

The first step involves the Friedel-Craft acylation of anthracene with oxalyl chloride in the presence of aluminium chloride and carbon disulfide solvent to form aceanthrylene-1,2-dione. The second stage involves oxidising aceanthrylene-1,2-dione with hydrogen peroxide under basic conditions (aqueous sodium hydroxide/1,4-dioxane) at room temperature to yield anthracene-1,9-dicarboxylic acid. The third and final stage involves reacting anthracene-1,9-dicarboxylic acid with an appropriately functionalised primary amine (alkyl, aryl, heterocyclic, etc) to form the 1,9-anthraimide.

Many of the possible reactive $R^1$ functional groups can be introduced onto the anthraimide fluorophore by employing an appropriate methylated anthracene precursor, for example; 9-methylanthracene. This methylanthracene precursor can then be converted to the appropriately N-functionalised anthraimide using the three-step protocol described above, i.e. Friedel-Craft acylation using oxalyl chloride, hydrogen peroxide mediated dione-oxidation, imidisation by reaction with an appropriate primary aryl, alkyl or heterocyclic amine. The resultant methyl-anthraimide can then be brominated at the methyl-carbon via free-radical halogenation using a stoichiometric amount of N-bromosuccinimide in refluxing carbon tetrachloride in the presence of a catalytic amount of a free-radical initiator such as benzoyl peroxide or 2,2'-azobisisobutyronitrile. This bromide can be substituted for other halides by employing Finkelstein reaction conditions, for example; the bromide can be converted to the iodide through reflux of the anthraimide-methylenebromide with excess potassium iodide in acetone solvent. The anthraimide-methylenebromide can be hydrolysed easily to a methylene-alcohol group through reflux with sodium hydroxide in N,N'-dimethylformamide. The anthraimide-methylenebromide can also be thiolised to a thiol group through reaction with a large excess of sodium hydrosulfide in refluxing ethanol. The methylene-alcohol can then be converted to its corresponding mesylate or tosylate through its reaction with mesyl chloride or tosyl chloride respectively in dichloromethane in the presence of pyridine base at 0° C.

The methylene bromide group can be oxidised to a formyl group through reaction with anhydrous trimethylamine-N-oxide in dry dichloromethane at room temperature. The resultant formyl group can then be reductively aminated with methanolic ammonia or primary or secondary amines in the presence of excess sodium borohydride to form primary, secondary or tertiary amines respectively. The primary anthraimide-methyleneamine can be converted to an isocyanate through reaction with phosgene in the presence of pyridine in dichloromethane at 0° C. The primary anthraimide-methyleneamine can also be converted to an isothiocyanate through its reaction with carbon disulfide in the presence of excess triethylamine in tetrahydrofuran at room temperature and subsequent degradation of the resultant dithiocarbamate salt with tosyl chloride at 0-22° C. In another approach the formyl group can be reacted, using Wittig conditions, with a phosphorus-ylide ($Ph_3P^+$—$CHR^{FG}$; FG=hydrogen, alkyl, aryl, heterocycle) in the presence of potassium hydride in tetrahydrofuran at 0° C. to form an alkene. This alkene can participate in a Prilezhaev reaction through reaction with m-chloroperoxybenzoic acid in dichloromethane at 0-20° C. to form an oxirane. This oxirane can be converted into its analogous thiirane through reaction of the oxirane with ammonium thiocyanate in refluxing acetonitrile in the presence of a catalytic amount of bismuth triflate.

The anthraimide-methylene alcohol and primary/secondary methylene amine groups formed as described above can easily be converted to (meth)acrylate and (meth)acrylamide Michael addition acceptor functionalities by reaction of the parent alcohol or amine with a (meth)acryloyl chloride in the presence of Hunig's base in dry dichloromethane at 0° C. The 1,9-anthraimide aryl-halide can also participate in Suzuki cross-coupling type reactions to introduce alkyl, alkenyl and aryl substituents. For example, reaction of a 1,9-anthraimide aryl-bromide with alkyl-9-BBN or alkenyl-9-BBN type precursors (9-BBN=9-boro-bicyclo[3.3.1]nonane) in the presence of palladium(II) acetate, potassium phosphate and tricyclohexylphosphine yields the cross-coupled product. To introduce aryl-functionalities a classic Suzuki-Miyaura coupling can be employed using the 1,9-anthraimide aryl-bromide, an arylboronic acid pinacol ester, $PdCl_2(dppf)_2$ catalyst [dppf=1,1'-bis(diphenyl-phosphino)ferrocene], a base ($K_2CO_3$) in 1,2-dimethoxyethane solvent at 80° C. for 2 hours. Nucleophilic substitution of the bromide functionality of an anthraimide-methylenebromide with potassium cyanide yields a methylenenitrile functionality which can be hydrolysed to a carboxylic acid through its treatment with aqueous sulphuric acid. The resultant anthraimide-methylenecarboxylic acid group can be converted to a reactive acid chloride through its reaction with refluxing thionyl chloride.

Other reactive $R^1$ functionalities can be synthesised via bromine-ring substituents. This requires synthesis of the intermediate anthracene-1,9-dicarboxylic acid, as described above, which can then be converted to anthracene-1,9-dicarboxylic anhydride through heating a solution of the parent diacid at 130° C. in N,N'-dimethylformamide for a period of 1-5 hours. The anthracene-1,9-dicarboxylic anhydride can be brominated using bromine in solvents such as chloroform, 1,2-ethylene dichloride, dioxane or acetic acid at 0-100° C. If more forcing conditions are required a Lewis acid catalyst such as anhydrous aluminium bromide can be added and the reaction run in hot 1,2-ethylene dichloride. The brominated anthracene-1,9-dicarboxylic anhydride can then be converted to the 1,9-anthraimide by refluxing it in the presence of an excess of the desired primary aryl/alkyl/heterocyclic amine in toluene/ethanol (9:1) for a period of 6-24 hours. The resultant brominated 1,9-anthraimide can then be borylated at the bromine substituent position(s) using the Miyaura borylation reaction involving its cross-coupling with bis(pinacolato)diboron in the presence of a catalytic amount of $PdCl_2(dppf)$ [dppf=1,1'-bis(diphenylphosphino)ferrocene] and potassium acetate in dioxane at 80° C. to yield the 1,9-anthraimide-boronic acid pinacol ester. The boronic acid pinacol ester can be cleaved to its parent boronic acid by transesterification with phenylboronic acid functionalised polystyrene in acetonitrile in the presence of a catalytic amount of trifluoroacetic acid. This boronic acid can then undergo a cross-coupling reactions with α,β-unsaturated acyl chlorides in the presence of a dichloropalladium(II) bis(triphenylphosphine) catalyst and potassium phosphate hydrate in toluene at 80° C. to form an 1,9-anthraimide-enones, the enone component of which is an excellent Michael acceptor. The anthracene 1,9-dicarboxylic anhydride intermediate can be directly nitrated using a combination of concentrated nitric acid and concentrated sulfuric acid, the temperature of the reaction (0-120° C.) can mediate the degree of nitration (mono-, di-, etc). The resultant nitroanthracene 1,9-dicarboxylic anhydride can then be converted to the 1,9-anthraimide through reaction with an appropriate alkyl/aryl/heterocyclic primary amine in a refluxing mixture of toluene/ethanol (9:1) for a period of 5-24 hours. The nitro group(s) can then be reduced to primary arylamine group by reaction with iron(0) in refluxing acetic acid. Reaction of the resultant primary arylamine with sodium nitrite, hydrochloric acid at 0° C. forms the diazonium salt (Ar—N≡N$^+$) which can be substituted for a cyanide group using Sandmeyer conditions (ArN≡N$^+$, Cu$^I$CN, 60-100° C.). The anthraimide-nitrile group can then be hydrolysed to a carboxylic acid through treatment with refluxing aqueous sodium hydroxide for 90 minutes followed by acidification of the reaction mixture cooled to 0° C. with aqueous hydrochloric acid. The carboxylic acid group can then be converted to a reactive acid chloride group by its reaction with refluxing thionyl chloride for a period of 3 hours. The acid chloride can then be treated with lithium organocuprate ($R_2$CuLi or $Ar_2$CuLi) in anhydrous tetrahydrofuran at −78° C. to room temperature to form a ketone functionality.

Where they are present, the R', R", R'" ring substituents are incorporated onto the basic 1,9-anthraimide framework in order to influence its physiochemical properties such as excitation/emission wavelengths, solubility, etc. The anthracene 1,9-dicarboxylic anhydride intermediate can be nitrated using a combination of concentrated nitric acid and concentrated sulfuric acid, the temperature of the reaction (0-120° C.) can mediated the degree of nitration (mono-, di-, etc). The resultant nitroanthracene 1,9-dicarboxylic anhydride can then be converted to the 1,9-anthraimide through reaction with an appropriate alkyl/aryl/heterocyclic primary amine in a refluxing mixture of toluene/ethanol (9:1) for a period of 5-24 hours. The nitro group(s) can then be reduced to primary arylamine group by reaction with iron(0) in refluxing acetic acid. The resultant primary arylamines can then be alkylated to secondary, tertiary amines by reductive amination with an appropriately functionalised carbonyl (aldehyde, ketone) precursor, for example one comprising the sensor architecture, in the presence of pinacol-borane in ethanol at 20-80° C. Alternatively the primary arylamine group can be directly alkylated to a quaternary ammonium salt by reacting it with an appropriate alkylbromide or arylmethylene bromide, etc, in N,N'-dimethylformamide at 70-120° C. Reaction of the primary arylamine with sodium nitrite, hydrochloric acid at 0° C. forms the diazonium salt (Ar—N≡N$^+$) which can be substituted using Sandmeyer conditions (ArN≡N$^+$, Cu$^I$X, 60-100° C., where X=Cl, Br, I, SR', CN, OH, OR', SCN). The diazonium salt can also be treated with acetic acid, sulfur dioxide and copper(II) chloride to displace the —N≡N$^+$ group with a sulfonyl chloride (—$SO_2$Cl) group and this functionality can either be hydrolysed with water to the yield a sulfonic acid, subjected to alcoholysis to form a sulfonate ester or reacted with ammonia or alkyl/aryl/heterocyclic primary and secondary amines to form sulfonamide moieties. Alternatively the diazonium salt of the 1,9-anthraimide primary arylamine can be formed under Balz-Schiemann reaction conditions (sodium nitrite, fluoroboric acid, 0° C.) to form the tetrafluoroborate salt of the diazonium cation which on thermal decomposition introduces a fluorine substituent at the ipso-carbon. The primary arylamine group can be reacted with (meth)acryloyl chloride in the presence of Hunig's base in an aprotic solvent such as dichloromethane at 0° C. to introduce a (meth)acrylamide polymerisable group at the $R^1$ ring position. Alternatively the hydroxy group introduced via the Sandmeyer reaction can be similarly treated with (meth)acryloyl chloride in the presence of Hunig's base in an aprotic solvent at 0° C. to place a (meth)acrylate polymerisable group directly on the 1,9-anthraimide. The arylhydroxy group can also be derivatised, in the presence of Hunig's base at 0° C. in an aprotic solvent, with alkoxycarbonyl chlorides, aryloxycarbonyl chlorides to form carbonates; or alkylaminecarbonyl chlorides, arylaminecarbonyl chlorides to form carbamates; or alkylsulfonyl chlorides or arylsulfonyl chlorides to form sulfonic acid esters. The primary arylamine group can also be reductively aminated with 4-formylstyrene and sodium borohydride in ethanol thus introducing a polymerisable vinylbenzene entity into the 1,9-anthraimide system. The primary arylamine group can also be derivatised, in the presence of Hunig's base at 0° C. in an aprotic solvent, with acid chlorides to form amides; or alkoxycarbonyl chlorides, aryloxycarbonyl chlorides to form carbamates; or alkylaminecarbonyl chlorides, arylaminecarbonyl chlorides to form ureas; or alkylsulfonyl chlorides or arylsulfonyl chlorides to form sulfonamides.

Alternatively the primary arylamine can be converted to a secondary amine through reaction with an alkyl or aryl aldehyde in ethanol in the presence of sodium borohydride reducing agent. The resultant secondary arylamine can then be further derivatised, in the presence of Hunig's base at 0° C. in an aprotic solvent, with acid chlorides to form amides; or alkoxycarbonyl chlorides, aryloxycarbonyl chlorides to form carbamates; or alkylaminecarbonyl chlorides, arylaminecarbonyl chlorides to form ureas; or alkylsulfonyl chlorides or arylsulfonyl chlorides to form sulfonamides. A formyl group can be introduced onto the 1,9-anthraimide using the method described for the anthraimide $R^1$-group, above, and this formyl group can then be reduced to form a benzylalcohol functionality which can be alkylated, for example with 4-vinylbenzyl chloride, or the formyl group can be reductively aminated, for example with 4-vinylbenzylamine and sodium borohydride, which are two methods of introducing a vinylbenzyl polymerisable functionality at the position. The benzylalcohol group can also be esterified, for example with (meth)acryloyl chloride in the presence of Hunig's base in an aprotic solvent at 0° C. yielding a (meth)acrylate polymerisable group. An anthraimide-nitrile group introduced under Sandmeyer conditions can be hydrolysed to a carboxylic acid functionality through treatment with hot aqueous sulphuric acid. This carboxylic acid can then be treated with refluxing thionyl chloride to form an acid chloride group which can be treated with an alcohol or amine in the presence of Hunig's base in an aprotic solvent at 0° C. to form an ester or an amide respectively. Alternatively the acid chloride group can be reacted with a lithium organocuprate ($R_2CuLi$ or $Ar_2CuLi$) in anhydrous tetrahydrofuran at −78° C. to room temperature to form a ketone functionality which can in turn be reduced under Wolff-Kishner conditions (hydrazine, base) to convert its >C=O carbonyl group to a >$CH_2$ methylene group forming an alkyl substituent.

Halide ring substituents can be introduced either through Sandmeyer protocols or by direct halogenation of the anthracene-1,9-dicarboxylic anhydride intermediate. For example, chlorination of the anthracene-1,9-dicarboxylic anhydride can be accomplished using sulfuryl chloride ($SO_2Cl_2$) at 0-100° C., either using neat $SO_2Cl_2$ or in 1,2-ethylene dichloride. Bromination can be accomplished using bromine in solvents such as chloroform, 1,2-ethylene dichloride, dioxane or acetic acid at 0 to 100° C. and if more forcing conditions are required a Lewis acid catalyst such as anhydrous aluminium bromide can be added and the reaction run in refluxing 1,2-ethylene dichloride. The halogenated anthracene-1,9-dicarboxylic anhydride can then be converted to the 1,9-anthraimide by refluxing it in the presence of an excess of the desired primary aryl/alkyl/heterocyclic amine in toluene/ethanol (9:1) for a period of 6-24 hours.

Halide ring substituents can additionally be employed to introduce organophosphorus groups to the 1,9-anthraimide. For example, a phosphine group can be introduced through the cross-coupling of an arylbromide with a secondary phosphine in the presence of palladium(II) acetate and 1,1'-bis(diisopropylphosphino)ferrocene co-catalysts, caesium carbonate base and N,N'-dimethylformamide solvent at 120° C. The resultant tertiary phosphine group can then be further alkylated with an alkyl mesylate in refluxing 1,2-ethylene dichloride to form a phosphonium salt.

Alternatively phosphinate [$OP(OR)R_2$], phosphonate [$OP(OR)_2R$] or phosphine oxide [$OPR_3$] groups can be introduced via a proline-promoted copper-catalyzed P-arylation reaction using a $R^1$ aryliodide and an $O=PH(R^L)(R^M)$ reagent (where $R^L$, $R^M$=alkyl, aryl, heterocycle, O-alkyl, O-aryl, O-heterocycle) in the presence of proline, caesium carbonate and a catalytic amount of copper(I) iodide in toluene at 110° C. The arylhalide substituents can also be used to incorporate alkyl, alkenyl and aryl ring substituents via Suzuki cross-coupling type reactions. The Suzuki cross-coupled alkyl, alkenyl, aryl substituents can be further functionalised, for example with hydroxyl, thiol, ether, thioether, amine, ammonium, etc, employing easily cleavable protecting groups where these functionalities might interfere with the initial cross-coupling reaction (e.g. tetrapyranyl-ether and thioether for hydroxyl, thiol respectively, tert-butoxycarbonyl for amines, etc). These additional functionalities can then be further derivatised, for example; an alkylhydroxyl can be converted to a mesylate and this reacted with a tertiary amine or phosphine to form a quaternary ammonium or phosphonium salt thereby conferring enhanced aqueous solubility onto the fluorophore. In another embodiment an alky/aryl hydroxyl could be converted to a methacrylate-ester group in order to introduce a polymerisable entity onto the 1,9-anthraimide.

The 1,9-anthraimide arylhydroxyl, arylamine and benzylalcohol, benzylamine functionalities can be used to introduce a "spacer" poly(alkylene)glycol or poly(alkylene)thioglycol by reaction with an appropriately functionalised oxirane or thiirane in the presence of a base (Hunig's base for amine, thiol and sodium hydride for alcohol) at room temperature. The terminal alcohol or thiol group of the resultant "spacer-chain" can be further functionalised if required, for example by reaction with 4-vinylbenzyl chloride in the presence of Hunig's base for the thiol functionality or by reaction with (meth)acryloyl chloride in the presence of Hunig's base in an aprotic solvent at 0° C. for the alcohol. Furthermore the terminal alcohol groups can be converted to a primary or secondary amine through oxidation of the alcohol to an aldehyde under Swern oxidation conditions (oxalyl chloride, dimethylsulfoxide, triethylamine at −30° C.) and then reductive amination of the aldehyde with ammonia (or primary amine) and sodium borohydride reducing agent. The resultant amine can then be reacted with (meth)acryloyl chloride in the presence of Hunig's base in an aprotic solvent at 0° C. or 4-formylstyrene and sodium borohydride in ethyl alcohol. Through methods such as these it is possible to incorporate a polymerisable group (vinylbenzene, (meth)acrylate, (meth)acrylamide, etc) directly onto the 1,9-anthraimide fluorophore separated by a poly(alkylene)glycol or poly(alkylene) thioglycol spacer group.

Sulfonyl chloride substituents can be directly introduced onto the anthraimide fused ring system via a chlorosulfonation reaction. This requires synthesis of the intermediate anthracene-1,9-dicarboxylic acid (i.e. Friedel-Craft acylation of anthracene-based precursor using oxalyl chloride followed by hydrogen peroxide mediated dione-oxidation) which can then be converted to anthracene-1,9-dicarboxylic anhydride through heating a solution of the parent acid at 130° C. in N,N'-dimethylformamide for a period of 1-5 hours. The anthracene-1,9-dicarboxylic anhydride can be chlorosulfonated using in neat chlorosulfonic acid at 20-100° C. for 2-12 hours. The resultant sulfonyl chloride substituted anthraimide can then be further derivatised by treatment with water (hydrolysis) to form sulfonic acid groups, alcohols (alcoholysis) to form $—SO_2OR^{BB}$ sulfonate esters, or by ammonia, primary or secondary amines to form $—SO_2NH_{2-n}R^{BB}{}_n$ sulfonamides (where n=0-2). The $R^{BB}$ group of R', R'', R''' anthraimide ring sulfonyl substituents can be an alkyloxy, aryloxy, alkylamine or arylamine as described above which can be further functionalised, for example with hydroxyl, thiol, amine, quaternary ammonium, quaternary phosphonium, sulfonic acid, phosphonic acid groups, by employing an appropriately functionalised precursor. For example through the treatment of a R', R'', R''' sulfonyl chloride intermediate with a primary or secondary haloalkylamine hydrochloride in the presence of Hunig's base and subsequent substitution of the alkyl halide with hydroxyl via basic hydrolysis, hydrosulfide (thiol) via reaction with sodium hydrosulfide in refluxing ethanol, or formation of the primary amine through the Gabriel synthesis (nucleophilic substitution with potassium phthalimide in refluxing tetrahydrofuran to form an alkyl phthalic imide which is then subjected to hydrazinolysis via the Ing-Manske procedure using hydrazine in refluxing ethanol to yield the primary amine). In the case of the $R^{BB}$ alkyl, aryl hydroxyl, thiol, amine groups these can be further functionalised, for example by nucleophilic substitution with 4-vinylbenzyl chloride in the presence of an appropriate base (Hunig's base for amine, thiol and caesium carbonate for alcohol) or by reaction with (meth) acryloyl chloride (for hydroxyl and amine) in the presence of Hunig's base in an aprotic solvent at 0° C. By such methods it is possible to incorporate polymerisable groups such as vinylbenzene, (meth)acrylate or (meth)acrylamide onto the $R^{BB}$ substituent(s). The $R^{BB}$ aryl/alkyl hydroxyl, thiol, amine functionalities can be used to introduce a "spacer" poly(alkylene)glycol or poly(alkylene)thioglycol through a nucleophilic ring-opening reaction with an appropriately functionalised oxirane or thiirane in the presence of a base (Hunig's base for amine, thiol and sodium hydride for alcohol) at room temperature. The terminal alcohol or thiol group of the resultant "spacer-chain" can be further functionalised if required, for example by reaction with 4-vinylbenzyl chloride in the presence of Hunig's base for thiol functionalities or by reaction with (meth)acryloyl chloride in the presence of Hunig's base in an aprotic solvent such as tetrahydrofuran at 0° C. for alcohol groups. The terminal alcohol group of a polyethyleneglycol "spacer" chain can be converted to a primary or secondary amine through oxidation of the alcohol to an aldehyde under Swern oxidation conditions (oxalyl chloride, dimethylsulfoxide, triethylamine at −30° C.) and then reductive amination of the aldehyde with ammonia, primary amine and sodium borohydride reducing agent. The resultant amine can then be reacted with (meth)acryloyl chloride in the presence of Hunig's base in an aprotic solvent at 0° C. or 4-formylstyrene and sodium borohydride in ethyl alcohol. By such methods it is possible to functionalise R', R", R''' sulfonyl chloride functionalities with a $R^{BB}$-spacer-$R^P$ motif.

As described earlier, the anthraimide fluorophore is synthesised from anthracene in three steps:
(i) The Friedel-Craft acylation of anthracene with oxalyl chloride in the presence of aluminium chloride and carbon disulfide solvent to form aceanthrylene-1,2-dione.
(ii) The oxidation of the aceanthrylene-1,2-dione with hydrogen peroxide under basic conditions (aqueous sodium hydroxide/1,4-dioxane) at room temperature to yield anthracene-1,9-dicarboxylic acid.
(iii) The reaction of the anthracene-1,9-dicarboxylic acid with an appropriately functionalised primary amine (alkyl, aryl, heterocyclic, etc) to form the 1,9-anthraimide requiring reflux of these two components in a toluene/ethanol (9:1) solvent mixture for a period of 5-24 hours.

The R-group attached to the imide nitrogen can be alkyl, aryl, heterocyclic and be further functionalised to confer additional properties onto the fluorophore, for example; aqueous solubility, polymerisability, etc. The additional functionality can be incorporated onto the R-imide ring substituent by reacting the anthracene-1,9-dicarboxylic acid intermediate with a primary amine functionalised with the desired supplementary group(s). The supplementary functionalities can include but are not limited to: alkylsulfonic acid salts, alkylphosphonic acid salts, alkylphosphonium salts, alkylammonium salts, alkylcarboxylate salts, alkylpyridinium salts, alkylimidazolium salts, alkyl phenylsulfonic acid salts, alkylphenylcarboxylate salts, alkylphenylammonium salts, arylphosphonium salts, imidazolium salts, pyridinium salts, arylsulfonic acid salts, arylcarboxylate salts, arylammonium salts, alkyl (meth)acrylates, aryl (meth)acrylates, alkylamine, alkylalcohol, alkylhalide, alkylamide, alkylester, arylalcohol (phenol), arylamine (aniline), arylamide, aryl ester. The alkyl/aryl alcohol, alkyl/aryl amine R-substituents can be further derivatised, for example by reaction with (meth)acryloyl chloride in the presence of Hunig's base in an aprotic solvent at 0° C. to form a (meth)acrylate or (meth)acrylamide respectively. The alkylamine or arylamine R-group can alternatively be reacted with 4-formylstyrene in ethyl alcohol and then reduced with sodium borohydride in order to form a vinylbenzylaminealkyl- or vinylbenzylaminearyl-polymerisable R-substituent. Equally the alkylalcohol or arylalcohol group can be deprotonated with sodium hydride base in anhydrous tetrahydrofuran yielding an alkoxide, phenoxide nucleophile which can be reacted with 4-vinylbenzyl chloride at 60° C. for 7 hours to form a vinylbenzyloxyalkyl- or vinylbenzyloxyaryl-polymerisable R-substituent.

Protecting Groups

In the planning and implementation of syntheses involving appropriately functionalised aminopyrene and 1,9-anthraimide based fluorophore designs it will be apparently to those skilled in the art that functional group selectivity may become a factor when assembling the fluorophore and sensor molecular architecture. For example, in a substrate containing multiple amine functionalities one may want to direct the reaction to just one of the amine functionalities whilst leaving the others untouched. Alternatively in a substrate containing multiple functional groups one might want to direct reaction towards one functionality and not another one of higher reactivity, for example; directing an acyl chloride to react with an alcohol and not a primary amine within the same molecule. Objectives such as these can be achieved by the implementation of standard protecting group protocols. The protecting group must react selectively with the functionality that requires deactivation to yield a protected intermediate that is stable to the reaction conditions required to effect the desired chemical transformation(s) at another site in the molecule. Once the potentially contentious chemical transformation(s) have been implemented the protecting group must then be capable of being selectively and efficiently removed using a reagent that does not affect the deprotected functional group or other functionalities present within the molecule. For primary and secondary amine groups, the protecting groups typically employed are tert-butoxycarbonyl (Boc) which is impervious to basic reaction conditions or 9-fluorenylmethoxycarbonyl (Fmoc) which is impervious to acidic environments. The Boc group can be coupled to a primary or secondary amine by refluxing the amine with tert-butyl phenyl carbonate in ethanol for a period of 8-24 hours. The Boc-N carbamate group can be cleaved by treatment with trifluoroacetic acid/dichloromethane (50:50) at room temperature. The Fmoc group can attached to a primary or secondary amine group by reaction of the amine with N-(9-fluorenylmethoxycarbonyloxy)succinimide in anhydrous tetrahydrofuran in the presence of an excess of potassium carbonate. The Fmoc-N carbamate can easily be cleaved to the parent amine and dibenzofulvene by reaction with an amine base such as 1,8-diazabicyclo[5.4.0]undec-7-ene (DBU), which is often employed in combination with an alkylmercaptan, such as 1-octanethiol, that acts as a dibenzofulvene scavenger. For alcohol groups protection methodologies can include the use of tetrahydropyranyl ethers (THP—OR), silyl ethers (trimethylsilyl, tert-butyl dimethylsilyl) or acyl-ester (acetate, benzoate). A THP-ether group can be introduced by reacting the alcohol with dihydropyran in the presence of a catalytic amount of tosic acid in dichloromethane at room temperature for a period of 90 minutes. The THP-ether group can be cleaved to the parent alcohol by treatment trifluoroacetic acid in dichloromethane (50:50) at room temperature. The silyl (trimethylsilyl, tert-butyl dimethylsilyl) protecting groups are tethered to alcohol groups via their chlorides in the presence of Hunig's base in anhydrous dichloromethane at 0° C. The silyl-ether groups be cleaved by treatment fluoride displacement via reaction with tetra-n-butylammonium fluoride (TBAF) in anhydrous tetrahydrofuran at room temperature, or by acidic hydrolysis through reaction with acetic acid, water, tetrahydrofuran (3:1: 1). Acyl-ester protecting groups can be introduced by reacting the alcohol with an acyl chloride (acetyl chloride, benzoyl chloride) in the presence of Hunig's base in anhydrous dichloromethane at 0° C. The acyl-ester protecting groups can be cleaved by basic hydrolysis, through reaction with aqueous sodium hydroxide with ethanol added as necessary to effect reagent solubility. Mercaptan groups can be protected as their S-9-fluoroenylmethyl thioethers (Fm-SR) which can be synthesised by reacting the mercaptan with 9-fluorenylmethyl tosylate in N,N-dimethylformamide at 0° C.-25° C. This protecting group is stable in acidic environments but is labile in basic media and can be efficiently cleaved through treatment with 50% piperidine in N,N-dimethylformamide. Protection of mercaptan groups with an acid labile protecting group can be achieved by forming a trityl thioether group (Tr-SR) which can be formed by reaction of the mercaptan with triphenylmethyl chloride. The trityl thioether can be cleaved with neat trifluoroacetic acid containing at least one equivalent of triethylsilane (carbocation scavenger). Carboxyl groups can be protected as 9-fluorenylmethyl esters (FmOOCR), which can be formed by reaction of the acid functionality with 9-fluorenylmethanol in combination with N,N'-dicyclohexylcarbodiimide (DCC) and 4-dimethylaminopyrdine (DMAP) in diethyl ether at room temperature for a period of 1-24 hours. The 9-fluorenylmethyl ester group is labile under basic conditions and can be cleaved through treatment with piperidine in dichloromethane at room temperature for a period of 2 hours. Phenacyl esters can be employed as acid stable carboxyl protecting groups formed by the reaction of a carboxylic acid with phenacyl bromide in the presence of triethylamine in ethyl acetate at room temperature for a period of 12-24 hours. The phenacyl ester protecting group can be reductively cleaved using zinc(0) in acetic acid at room temperature. Those skilled in the art will be aware when formulating a synthetic strategy when it is appropriate to employ protecting group methodologies of the types summarised above to achieve functional group monoselectivity (e.g. preferential reaction of one amine over another within a single substrate) or to circumvent "clashing" of different functional group reactivities (e.g. preferential reaction of an alcohol over that of an amine within the same substrate with an acyl chloride).

EXAMPLES

Example 1

6-Aminopyrene-1,3-disulfonic acid bis-diisobutylamide, 1a

An aminopyrene fluorophore of the invention was prepared according to the following method:

Powdered 1-aminopyrene (25 g, 115 mmol) was stirred under an atmosphere of nitrogen. The flask was placed in an ice bath and then a solution of chlorosulfonic acid (200 ml) was added drop-wise over a 50 minute period, after which a dark green solution had formed. The solution was allowed to warm to room temperature and stirring maintained overnight. The green reaction mixture was then cautiously added drop-wise to a stirring slurry of ice/water whereupon a dense red/purple precipitate containing crude 6-aminopyrene-1,3-disulfonyl dichloride deposited (a considerable amount hydrochloric acid fumes were generated during the addition and these were "scrubbed" by bubbling through 1M NaOH). The red/purple was collected by filtration and washed several times with cold water and then sucked 'dry' on the filter pad. This was added to a stirred solution of diisobutylamine (170 ml, 973 mmol) in $CH_3CN$ (350 ml) at room temperature under an atmosphere of nitrogen. The resultant mixture was allowed to stir overnight and then water (500 ml) and $CH_2Cl_2$ (500 ml) were added. The dark mixture was stirred for 1 hour and then the lower organic phase was partitioned and separated, then dried (anhydrous $MgSO_4$) and concentrated in vacuo to give a dark red oil/tar (~200 g). This was then passed down a large silica-gel plug using $CH_2Cl_2$ to remove the baseline impurities. The product containing fractions were combined and concentrated to give 26 g of orange solid. This was then subjected to several silica columns (Petroleum ether/$CH_2Cl_2$/EtOAc in a 2:1:1 ratio) to give the product as a mixture of regio-isomers (2.8 g, 20% yield) as an orange/brown solid. HPLC analysis of this column purified product indicated a purity of 94.5% for the combined regio-isomers with a residual 3.6% of impurity components. $^1$H NMR (CDCl$_3$) δ 0.85 (dd, 24H, isobutyl —CH$_3$), 1.95 (m, 4H, isobutyl >CH—), 3.21 (d, 81-1, isobutyl NCH$_2$<), 4.90 (bs, 2H, Ar—NH$_2$), 7.49 (d, 1H, pyrene ArH), 8.23 (t, 2H pyrene ArH), 8.32 (d, 1H, pyrene ArH), 8.73 (d, 1H, pyrene ArH), 8.93 (d, 1H, pyrene ArH), 9.14 (s, 1H, pyrene ArH).

The thus produced 6-Aminopyrene-1,3-disulfonic acid bis-diisobutylamide was recrystallised from ethyl acetate/n-hexane forming a mass of yellow-orange crystals which were deemed as being of sufficient size and quality for crystallographic characterisation. A yellow-orange prism of 0.20× 0.15×0.10 mm was mounted onto a Nonius Kappa CCD diffractometer with a Mo Kα X-ray source which yielded the following crystallographic parameters; crystal system: triclinic, space group: P1 bar, cell dimensions: a=8.75300(10) Å; b=11.7530(2) Å; c=32.8390(7) Å; α=89.4710(10)°; β=88.2050(10)°; γ=71.5030(10)°, V=3202.19(9)Å$^2$, Z=4. 13762 unique reflections were collected at a temperature of 150K of which 8976 exceeded the 2σ(I) threshold. The structure was solved by direct methods, using the SIR97 software package (A. Altomare, M. C. Burla, M. Camalli, G. L. Cascarano, C. Giacovazzo, A. Guagliardi, A. G. G. Moliterni, G. Polidori and R. Spagna, *J. Appl. Cryst.* (1999). 32, 115-119), and then refined by full-matrix least-squares, using the SHELXL97 software package (G. M. Sheldrick, *Acta Cryst.* (2008), A64, 112-122), using all of the reflection data yielding the following residuals: R$_1$[I>2σ(I)]=0.1467; wR$_2$[I>2σ(I)]=0.3156. The resulting crystal structure is depicted in FIG. 1.

Example 2

10-Formyl-N-[2-(methoxy)ethyl]-anthracene-1,9-dicarboxylic imide, 5b

An anthraimide fluorophore of the invention was prepared according to the following method:

6-Methylaceanthrylene-1,2-dione, 1b

To a cold (−10° C., brine/ice cooling bath) stirred mixture of 5.43 g (28.2 mmol) of 9-methylanthracene and oxalyl chloride (13.50 mL, 159.5 mmol) in CS$_2$ (60 mL) was added aluminium chloride (6.0 g, 45 mmol). The solution changed from a red-orange colour to a very intense dark crimson colour and vigorous effervescence was observed (hydrogen chloride) and an exotherm occurred raising the reaction temperature from −10° C. to −4° C. After a few minutes stirring the exotherm eased off and an intense dark red tar deposited from the solution which lightened to a yellow colour, the reaction mixture was then stirred cold for a period of 2 hours. After 2 hours, additional CS$_2$ (60 mL) and aluminium chloride (4.5 g, 33.7 mmol) were added, and stirring was continued for 2 hours at 0° C. and then overnight at room temperature. HCl (2M, aq, 150 mL) was then added to the reaction mixture [NOTE: Extreme caution, very exothermic reaction ensues that causes vigorous reflux of reaction solvent], the reaction mixture was then stirred vigorously for 2 hours (large egg-shaped magnetic stirrer follower stirred at 1250 rpm) to decompose the dark red tar to an orange precipitate which was then collected by filtration, washed with water (2×150 mL), and then digested well with 300 mL of 5% NaOH(aq) for a period of 1 hour. The insoluble solids were collected by filtration, washed with water (2×50 mL), and dried in vacuo in a vacuum oven (oil immersion pump) to constant mass (22 hours). Yield: 2.411 g (34.7%, pale orange powder).

10-Methylanthracene-1,9-dicarboxylic acid, 2b 1b (2.411 g, 9.79 mmol) was suspended in 34 mL of 2M NaOH(aq) and dioxane (169.5 mL) at 15° C. This suspension was then treated with 28.85 mL of 30% aqueous hydrogen peroxide solution at 15° C. (dropwise addition over 15 minutes) causing the orange suspension to immediately lighten to an off-white colour and some material dissolved to form a pale orange-yellow solution. This mixture was then stirred at room temperature for a period of 60 minutes at room temperature during which time most of the off-white solid dissolved to form a turbid orange-yellow solution. The reaction mixture was then diluted with 319 mL of de-ionised water and acidified with 10% aqueous sulfuric acid (to pH 1). This caused the solution to deepen to a red-orange colour and after about 5-10 minutes a red-orange precipitate started to very slowly deposit from the solution. The mixture was then stirred vigorously at room temperature overnight during which time additional precipitate deposited from solution. The solid in the suspension was then collected by filtration (porosity 3 sinter) and washed with 2×150 mL portions of de-ionised water and air-dried on the sinter for 30 minutes. The deep red-orange solid was then further dried in vacuo in a vacuum oven at a vacuum pressure of 0.1 torr for a period of 24 hours at 40 deg C. Yield: 2.202 g (80.25%, red-orange powder).

10-Methyl-N-[2-(methoxy)ethyl]-anthracene-1,9-dicarboxylic imide, 3b 2-(Methoxy)ethylamine (0.71 g, 9.453 mmol) was weighed into a 500 mL RB flask. EtOH (87 mL)/toluene (230 mL) were added to the flask followed by 2b (2.202 g, 7.857 mmol) forming a red-orange suspension. The flask was attached to a double-layer coil condenser and this in turn was connected to a nitrogen-vacuum manifold and the apparatus flushed with nitrogen. The reaction flask was immersed in a silicone heating oil bath and the reaction mixture heated to a temperature of 130° C. under nitrogen causing the reaction mixture to reflux vigorously. The reaction mixture was refluxed for a period of 50 hours under nitrogen, during which time the orange suspension of 2b slowly dissolved to form a deep brownish red solution with a fluorescent green meniscus, before being allowed to cool slowly to room temperature. After cooling another aliquot of 2-(methoxy)ethylamine (1.65 mL; ca. 2.4 equivalents) was added to the reaction mixture via a 2.5 mL Hamilton gastight syringe. The reaction mixture was then brought up to reflux under nitrogen and reflux maintained for a period of 22 hours before the reaction mixture was allowed to cool to room temperature. The solvent was stripped off in vacuo (rotary evaporator) to yield a red-orange solid. A small portion of this material was analysed by TLC (eluant mixture: 8% EtOAc/92% chloroform) on a SIL-G/UV254 plate, the developed plate exhibited a single strongly green-yellow fluorescent spot in visible light at an $R_f$ value of ca. 0.5. Under $UV_{365}$ irradiation further spots were observed at the solvent front and two small ones on and just above the baseline. The crude product was dissolved in 60 mL of $CH_2Cl_2$ and then pre-loaded onto 4 g of Merck 60 (15-40 μm) silica gel by rotary evaporation and the resultant orange powder loaded onto a 65 diameter dry-flash column packed with Merck 60 (15-40 μm) to a depth of 55 mm. The column was then eluted thus: fraction volumes: 50 mL, fraction times: 3 minutes, elution gradient: (i) 1×100 mL fraction of n-hexane; (ii) 0-50% EtOAc in 2.0% increments/100-50% chloroform in 2.0% increments (26 fractions in total). Fractions' 9-25 were then analysed by TLC (elution mixture: 8% EtOAc/92% chloroform) which indicated the $R_f$ 0.5 spot was contained in fractions' 9-26 (highly tailed) though #9 contained a negligible amount of material and was discarded and #25-26 contained lower $R_f$ spots (i.e. cross-fractions) and were also discarded. Fractions' 10-24, the product fractions, were combined and stripped to dryness yielding an orange solid which was then further dried in vacuo for a period of 18 hours (0.45 torr) at room temperature. Yield: 2.208 g (88%, red-orange microcrystalline powder). $^1$H NMR (CDCl$_3$) δ 3.25 (s, 3H, [Ar—CH$_3$]$_{anthracene}$], 3.42 (s, 3H, —OCH$_3$), 3.80 (t, 2H, MeOCH$_2$—), 4.56 (t, 2H, >NCH$_2$—), 7.62-7.85 (m, 3H, ArH), 8.42 (d, 1H, ArH), 8.70 (d, 1H, ArH), 8.79 (d, 1H, ArH), 10.11 (d, 1H, ArH).

10-Bromomethyl-N-[2-(methoxy)ethyl]-anthracene-1,9-dicarboxylic imide, 4b 3b (2.20 g, 6.89 mmol), N-bromosuccinimide (1.25 g, 7.02 mmol) and anhydrous barium carbonate (2.10 g, 10.6 mmol) were weighed into a 150 mL RB flask which was connected to a double-layer coil condenser which in turn was connected to a nitrogen-vacuum manifold. CCl$_4$ (88 mL) was then added to the reaction flask. Separately 0.060 g of AIBN was weighed into a 10 mL volumetric flask and dissolved in 10 mL of CCl$_4$ and 2.00 mL of this solution was added to the reaction mixture via a digital pipette. The reaction mixture was then brought up to reflux under nitrogen for a period of 4 hours under nitrogen. As the reaction mixture warmed to reflux the orange solid, 3b, dissolved but after about 50 minutes reflux a dense orange microcrystalline started to precipitate from the reaction mixture (product). The reaction mixture was then allowed to cool slowly to room temperature.

The reaction mixture was then filtered through a porosity 3 sinter and the collected solid washed with 2×5 mL portions of CCl$_4$. The filtrate and washings were discarded. The collected solid on the sinter from the filtration of the reaction mixture was returned to the reaction flask. 100 mL of CH$_2$Cl$_2$ was added to the reaction flask which was then connected to a double-layer coil condenser which was in turn connected to a nitrogen supply and warmed very gently with a heat-gun whilst being magnetically stirred for a period of 10-15 minutes, this helped dissolve most of the orange solid. The mixture was then allowed to settle and the deep orange solution was decanted from the remaining solid into a porosity 3 sinter and filtered through it. Additional CH$_2$Cl$_2$ (50 mL) was added to the reaction flask which was again connected to the condenser/nitrogen supply and gently warmed until all the orange solid had dissolved leaving behind a small amount of white barium carbonate. This solution was filtered through the porosity 3 sinter. The two CH$_2$Cl$_2$ solutions were combined in a 500 mL-separating funnel and extracted with 2×250 mL portions of brine. The organic layer was then partitioned and separated and dried over anhydrous MgSO$_4$ for a period of 1 hour. The drying mixture was then filtered and the collected solid washed with 3×20 mL portions of ethyl acetate (the orange material seemed to 'stick' to the MgSO$_4$ and therefore required washing with a more polar solvent). The filtrate and washings were combined and concentrated in vacuo using a rotary evaporator causing a microcrystalline pale orange solid to deposit from the solution as it was concentrated. The pale orange solid that coated the walls of the evaporation flask on stripping off the solvent was then further dried in vacuo (oil immersion pump) at room temperature for a period of 20 hours. Yield: 2.475 g (90.2%, pale orange microcrystalline solid). $^1$H NMR (CDCl$_3$) δ 3.41 (s, 3H, —OCH$_3$), 3.80 (t, 2H, MeOCH$_2$—), 4.55 (t, 2H, >NCH$_2$—), 5.50 (s, 2H, ArCH$_2$Br), 7.72-7.90 (m, 3H, ArH), 8.42 (d, 1H, ArH), 8.66 (d, 1H, ArH), 8.80 (d, 1H, ArH), 10.11 (d, 1H, ArH).

10-Formyl-N-[2-(methoxy)ethyl]-anthracene-1,9-dicarboxylic imide, 5b

Anhydrous trimethylamine N-oxide (2.467 g, 33.3 mmol) was weighed into a 150 mL RB flask containing 4b (2.467 g, 6.195 mmol) in a glove bag filled with nitrogen. This flask was connected to a Claisen head within the bag before being removed and then very quickly connected to a double-layer coil condenser and then purge-filled with nitrogen three times. Anhydrous CH$_2$Cl$_2$ (75.0 mL) was then added to the flask via a gastight syringe forming a dense pale orange suspension. The reaction mixture was then stirred at room temperature under nitrogen and it was noticed that after a few minutes that the dense orange suspension was starting to dissolve forming a deep orange solution. After about 5 minutes all of the orange solid had dissolved when suddenly the reaction mixture became turbid and a precipitate of small, fine needle-like crystals deposited from the reaction mixture (presumably trimethylammonium bromide?). The reaction mixture was then stirred at room temperature under for a period of 75 minutes. After 75 minutes the reaction was quenched by addition of 75 mL of saturated brine forming a pale orange emulsion. This mixture was then transferred to a 250 mL-separating funnel and the aqueous layer separated from the organic layer. The aqueous layer was then washed with a further 3×25 mL portion of CH$_2$Cl$_2$ (for the 1st extraction an emulsion formed which was broken up by adding additional NaCl to the mixture, shaking vigorously for 5 minutes then filtering the mixture and allowing it to partition). The organic layers were then combined and then dried over anhydrous MgSO$_4$ for a period of 45 minutes. The drying mixture was then filtered and the collected solid washed with 3×20 mL portions of EtOAc. The filtrate and washings were then combined and stripped to dryness, as the solution concentrated a deep red-orange precipitate deposited from the solution. On completion of the evaporation to dryness the deep red-orange solid on the walls of the flask was scraped off with a spatula. A small sample of this solid was analysed by TLC (eluant mixture: 10% EtOAc/90% CHCl$_3$) against a sample of the 4b starting material which indicated a prominent low fluorescence (under UV$_{365}$) yellow spot at R$_f$ 0.5 with an R$_f$ slightly lower than that of the strongly fluorescent (under UV$_{365}$) 4b starting material, there were also several minor spots (all strongly fluorescent under UV$_{365}$) on or near the baseline up to an R$_f$ of ca. 0.30. This deep red-orange solid was pre-loaded onto 3.0 g of Merck 60 (15-40 um) silica-gel and then purified by dry-column flash chromatography using the following parameters: Column size: 65 mm diameter/55 mm depth. Silica Gel: Merck 60 (15-40 um). Time per fraction: 3.0 minutes. Fraction volumes: 50 mL. Elution gradient: 100-72% CHCl$_3$ in 1% increments/0-28% EtOAc in 1% increments (a total of 29 fractions). On elution of the column fractions' 8-29 exhibited a degree of colouration. TLC analysis of fractions' 12-28 (elution mixture: 10% EtOAc/90% CHCl$_3$) indicated that fractions 13-25 contained almost all of the desired R$_f$ 0.50 yellow spot (UV$_{365}$/visible illumination) with fractions' 26-27 also containing a significant proportion of the R$_f$ 0.50 product together with a small amount of the R$_f$ 0.30 side-product, subsequent fractions were cross-fractions (with the R$_f$ 0.3 spot) with rapidly diminishing amounts of the desired R$_f$ 0.5 product and were thus discarded. Fractions' 13-27 were combined and stripped to dryness in vacuo (rotary evaporator) to yield an orange solid which was then further dried in vacuo (oil immersion pump) overnight at room temperature. Yield: 1.085 g (52.55%, orange solid). $^1$H NMR (CDCl$_3$) δ 3.41 (s, 3H, OCH$_3$), 3.82 (t, 2H, MeOCH$_2$—), 4.57 (t, 2H, >NCH$_2$—), 7.75-7.90 (m, 3H, ArH), 8.62 (d, 1H, ArH), 8.80 (d, 1H, ArH), 8.98 (d, 1H, ArH), 10.12 (d, 1H, ArH), 11.52 (s, 1H, ArCHO).

Example 3

6-[2-([2-(boronic acid)benzyl]-{6-[[2-(boronic acid)benzyl]-(4-vinylbenzyl)amino]hexyl}amino)-ethylamino]pyrene-1,3-disulfonic acid bis-diisobutylamide, 8c A fluorescent sensor compound comprising the fluorophore of Example 1 was prepared according to the following method:

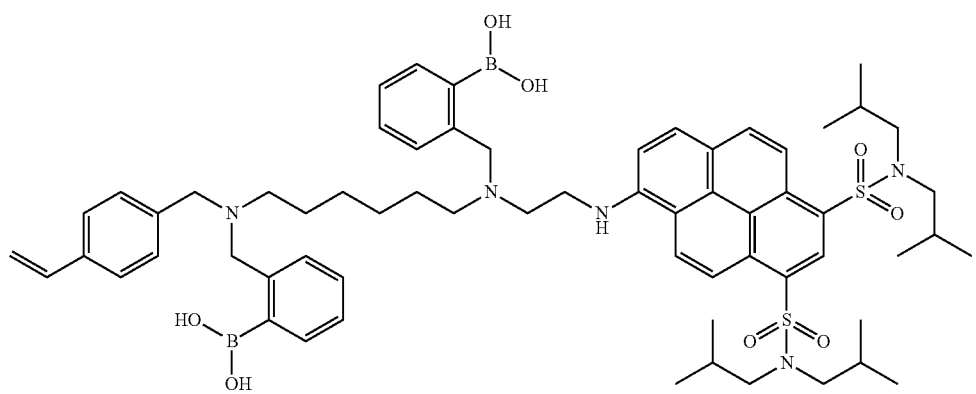

8c

4-Formylstyrene, 1c

4-Chlorostyrene (35 g) was distilled over sodium hydroxide pellets (1.0 g) in vacuo. The initially pale brown 4-chlorostyrene turned very dark blue on stirring with the NaOH pellets (due to deprotonation of the 0.10 wt % 4-tert-butyl-catechol inhibitor). The inhibitor free 4-chlorostyrene distilled over at a temperature of 41-43.5° C. at a pressure of 4.10 torr.

Magnesium turnings (99.8% pure, 5.50 g, 0.226 moles) were placed into a dry (heat-gun dried under vacuum) 3-neck 500 mL RB flask attached to a double-layer coil condenser, a 125 mL pressure-equalising funnel with a needle valve, a B19 suba-seal and a vacuum-nitrogen manifold and purge-filled with nitrogen. 27.6 g (0.199 moles) of freshly distilled inhibitor free 4-chlorostyrene was weighed into a dry 100 mL graduated Schlenk tube. This flask was purge-filled with nitrogen and 100 mL of anhydrous THF was cannula transferred into the flask forming a colourless solution. The 4-chlorostyrene solution was then cannula transferred into the addition funnel. A solution of 1.5 mL of ethylbromide in 4 mL of anhydrous THF was then added via syringe to the magnesium turning to initiate the reaction. The flask became warm to the touch and the solution coating the magnesium turning started to reflux. The 4-chlorostyrene solution was then added at such a rate as to maintain a gentle reflux over a period of 45 minutes. The grey reaction mixture was then stirred at room temperature for 20 minutes before being brought to reflux for 15 minutes using a heat gun. The reaction mixture was then allowed to cool slowly to room temperature over a period of 1 hour by which time most of the magnesium had reacted to form p-vinylphenylmagnesium chloride bar a few small shavings.

A solution of 17.06 mL (0.220 moles) of anhydrous N,N'-dimethylformamide in 100 mL of anhydrous tetrahydrofuran was cannula transferred into the 125 mL addition funnel and then added dropwise over a period of 1 hour to the previously prepared solution of p-vinylphenylmagnesium chloride (0.199 moles). The temperature was maintained at 20° C. during the addition (higher temperatures resulted in polymer formation and lower yields). The reaction mixture was stirred for 2 hours and then allowed to remain overnight under a nitrogen atmosphere. The reaction mixture was quenched with 200 mL saturated aqueous ammonium chloride solution causing an initial exotherm (up to 45° C.) and then the precipitation of a voluminous "gelatinous" white solid (magnesium hydroxides). The resultant emulsion was broken by centrifuging aliquots of the mixture at 4000 rpm for 3 minutes and the resultant clarified two phase mixture poured into a 500 mL separating funnel and the organic layer partitioned and collected. The remaining aqueous layer was extracted twice with 100 mL of $Et_2O$; the organic extracts were then combined and dried over anhydrous $MgSO_4$. The drying mixture was filtered and the collected solid washed with 2×50 mL portions of $Et_2O$. The filtrate and washings were combined and the solvent was stripped off in vacuo using a rotary evaporator and the residue was distilled in vacuo in the presence of a heaped spatula measure of phenothiazine with two fractions coming over: Fraction 1 (53° C. at 0.425 torr; v. pale yellow liquid), Fraction 2 (48-50° C. at 0.350 torr; v. pale yellow liquid). Fraction 1 was discarded and fraction 2 retained and a yield taken. Yield: 18.325 g (70%, very pale yellow liquid). $^1$H NMR ($CDCl_3$) δ 5.46 (d, 1H, =C—H), 5.93 (d, 1H, =C—H), 6.79 (dd, 1H, =C—H), 7.57 (d, 2H, ArH), 7.86 (d, 2H, ArH), 10.01 (s, 1H, —CH=O).

$N^1$-(2,2-diethoxyethyl)hexane-1,6-diamine, 2c

Into a 1 L 3-neck RB flask was weighed hexamethylenediamine (59.0 g, 508 mmol). To this flask was then added 400 mL of 2-ethyl-1-butanol. Bromoacetaldehyde diethyl acetal (100.1 g, 507.7 mmol) and potassium hydroxide (29.0 g, 517 mmol) were weighed out and added to the reaction flask. A large egg-shaped magnetic stirrer follower was then placed in the flask and its side-arms stoppered with B19 glass stoppers and its centre-socket connected to a B24 double-layer coil condenser which was in turn connected to a nitrogen line and the apparatus flushed with a flow of nitrogen gas. The reaction mixture heated to 165° C. over a period of 30 minutes. As the reaction mixture neared reflux temperature (146° C.) the mixture started boiling quite vigorously indicative of an exotherm taking place and a white precipitate of potassium bromide (KBr) deposited from the solution and the colour of the reaction mixture changed from a pale yellow to an orange colour. The reaction mixture was refluxed for a further period of 5 hours under nitrogen before the reaction mixture allowed to cool slowly to room temperature under nitrogen. The reaction mixture was then filtered through a porosity 3 sinter to remove the KBr that had deposited from the reaction mixture. The 2-ethyl-1-butanol was then stripped from the filtrate by in vacuo distillation at a vacuum pressure of 14 torr and a heating oil bath temperature of 80-100° C. The residue in the distillation flask deposited additional pale yellow precipitate, presumably more KBr, necessitating the re-filtration of the concentrated reaction mixture. The collected solid was washed with 2×30 mL of diethyl ether. The filtrate and washings were combined and the ether component stripped off in vacuo using a rotary evaporator. The residue in the flask was then fractionally distilled in vacuo through a 30 cm glass column packed with 0.5 cm Fenske rings: Fraction 1: 23-36° C. (0.45 torr); a colourless liquid, presumably residual 2-ethyl-1-butanol. Fraction 2: 36-102° C. (0.35 torr); predominantly a white solid, unreacted hexamethylenediamine, that solidified in condenser. The apparatus was disassembled at this point so that a clean condenser could be substituted for that containing the hexamethylenediamine. Fraction 3: 106-109° C. (0.44 torr); colourless liquid which contained some white solid (residual hexamethylenediamine). On completion of the collection of the third fraction collection the apparatus was allowed to cool slowly to room temperature overnight under a nitrogen atmosphere. Next day the condenser containing most of the entrained white solid was substituted for a clean condenser and the distillation was re-started. Fraction 4: 112-115° C. (0.60 torr); colourless liquid containing a small amount of an entrained white solid.

Fractions' 3 and 4 were then combined and filtered to remove the white solid and then fractionally re-distilled in vacuo through a 19 cm jacketed Vigreux column. Fraction 1: 96-101° C. (0.10 torr); white solid entrained in colourless liquid. Fraction 2: 101-108° C. (0.09 torr); colourless liquid containing a very small amount of white solid, which was removed by filtration. Fraction 3: 110-113° C. (0.078 torr); colourless liquid. The first and second fractions containing were discarded whereas the third fraction was retained and a yield taken. Yield: 40.0 g (34%; colourless liquid). $^1$H NMR ($CDCl_3$) δ 1.094 (3H, bs, NH), 1.184 (t, 6H, —$CH_3$), 1.13 (m, 4H, —$CH_2$—), 1.43 (m, 4H, —$CH_2$—), 2.58 (t, 2H, hexamethylene bridge >$NCH_2$—), 2.67 (t, 2H, hexamethylene bridge >$NCH_2$—), 2.69 (d, 2H, 2,2-diethoxyethyl $NCH_2$—), 3.53 (m, 2H, $H^A$ of OC($H^A$)($H^B$)—), 3.67 (m, 2H, $H^B$ of OC($H^A$)($H^B$)—), 4.565 (t, 1H, —CH(OR)$_2$).

$N^1$-(4-vinylbenzyl)-$N^6$-(2,2-diethoxyethyl)hexane-1,6-diamine, 3c

4-Formylstyrene, 1c (2.98 g, 22.5 mmol) and 2c (5.00 g, 21.5 mmol) were weighed into a 250 mL 3-neck RB flask and ethanol (90 mL) added forming a colourless solution. The flask was then attached to two B19 stoppers (side-arms) and a B24 double-layer coil condenser (centre-socket) and this in turn connected to a nitrogen-vacuum manifold. The apparatus was flushed with nitrogen and the reaction mixture stirred overnight at room temperature. Next day 3-(diethylenetri-amino)propyl-functionalised silica gel (1.85 g, 1.23 mmol/g loading) was added to the reaction mixture which was stirred at room temperature under nitrogen for a period of 6 hours in order to scavenge the excess 4-formylstyrene. Sodium borohydride (1.22 g, 32.2 mmol) was then added to the reaction mixture which was then stirred at room temperature for a period of 65 hours under nitrogen. Water (100 mL) was then added to the reaction mixture via syringe in order to quench the reaction. The reaction mixture was then stirred for 30 minutes at room temperature before the ethanol was stripped from the mixture in vacuo using a rotary evaporator to yield a white emulsion. $CH_2Cl_2$ (100 mL) was added to this residue and the resultant mixture transferred to a 250 mL-separating funnel. Water (10 mL) was added to the funnel which was then shaken and the layers partitioned and the lower organic layer decanted off. The aqueous layer was discarded and the organic layer then extracted with a further 2×100 mL portions of brine. The layers were partitioned and the lower organic layer collected and dried over anhydrous $MgSO_4$ for a period of 1 hour. The drying mixture was filtered and the collected solid washed with 3×20 mL portions of $CH_2Cl_2$. The filtrate and washings were combined and stripped to dryness in vacuo using a rotary evaporator for a period of 1 hour to yield a very pale yellow oil. This was then further dried in vacuo (0.25 torr) at room temperature for a period of 20 hours. Yield: 6.82 g (91%, pale yellow oil). NMR ($CDCl_3$) δ 1.21 (t, 6H, —$CH_3$), 1.32 (bm, 4H, —$CH_2$—), 1.48 (bm, 4H, —$CH_2$—), 2.61 (triplet of doublets, 4H, hexamethylene bridge >$NCH_2$—), 2.71 (d, 2H, 2,2-diethoxyethyl $NCH_2$—), 3.54 (m, 2H, $H^A$ of OC($H^A$)($H^B$)—), 3.69 (m, 2H, $H^B$ of OC($H^A$)($H^B$)—), 3.76 (s, 2H, >$NCH_2Ar$), 4.59 (t, 1H, —CH(OR)$_2$), 5.20 (d, 1H, =C—H), 5.72 (d, 1H, =C—H), 6.70 (dd, 1H, =C—H), 7.26 (d, 2H, ArH), 7.36 (d, 2H, ArH).

{6-[(2,2-Diethoxyethyl)-(9H-fluoren-9-ylmethoxy-carbonyl)amino]hexyl}-(4-vinylbenzyl)carbamic acid 9H-fluoren-9-ylmethyl ester, 4c 3c (4.50 g, 12.9 mmol) was weighed into a 250 mL 3-neck RB flask which was then stoppered (side-arms) and attached to a nitrogen/vacuum line. The flask was purge-filled with nitrogen three times and then THF (100 mL, anhydrous) was cannula-transferred into the flask forming a colourless solution. $Na_2CO_3$ (5.50 g, 51.9 mmol) was added to the flask in one portion followed by Fmoc-OSU (8.80 g, 26.1 mmol) which was weighed out and added in a single portion. A slight exotherm was observed (<5° C.) and the reaction mixture subsequently stirred for 40 hours at room temperature under a nitrogen atmosphere. Over this period a dense white precipitate deposited from the reaction mixture. The reaction mixture was then filtered and the collected solid washed with 2×25 mL portions of THF. The filtrate and washings were combined and stripped to dryness on a rotary evaporator yielding a slightly turbid colourless oil. This oil was then analysed by TLC (silica-gel plate; 30% EtOAc/70% n-hexane solvent mixture) which indicated a main product peak at Rf 0.5. This was then purified by dry-column flash chromatography using an 8 cm diameter/8 cm deep porosity 3 sinter. The crude product was pre-loaded onto 12 g of TLC grade Merck 60 (15-40 μm) silica gel and loaded onto the column packed with Merck 60 silica gel and the column eluted thus: fraction volumes: 100 mL; time per fraction: 4 min; EtOAc (0-60% in 4% increments)/n-hexane (100-40% in 4% increments).

Foaming was observed in fractions' 11 and 12 and subsequent TLC analysis (30% EtOAc/70% n-hexane) of fractions' 9-16 indicated the product was contained within fractions' 11-13 which were then combined. A tip of a microspatula measure of MEHQ was added to the combined solution that was then stripped to dryness in vacuo using a rotary evaporator yielding a colourless oil, which was then further dried in vacuo (oil immersion pump) for a period of 6 hrs forming a white "sticky" foam. Yield: 8.75 g (85%). $^1$H NMR ($CDCl_3$, spectrum was extremely complex due to conformational stereoisomerism of the 2,2-diethoxyethyl group caused steric interference from the proximal Fmoc protecting group on the 6-amine group of the hexamethylene diamine bridge of 4c) δ 0.82-1.56 (overlapping 2×bm and 2×t, 14H, from hexamethylene bridge —$CH_2$— and diethyl acetal —$CH_3$ groups respectively), 2.35-3.30 (four overlapping peaks [bs, d, t, m respectively], 7H, from 2× hexamethylene bridge >$NCH_2$— groups and 1× diethyl acetal $H^A$ of OC($H^A$)($H^B$)— group and $H^C$ from hindered 2,2-diethoxyethyl >NC($H^C$)($H^D$)— group), 3.49 (m, 2H, 1× diethylacetal $H^B$ of OC($H^A$)($H^B$)— group), 3.20 (m, 1H, $H^D$ from hindered 2,2-diethoxyethyl >NC($H^C$)($H^D$)— group, 4.05-4.65 (five overlapping peaks [t, bs, bd, bd, bt respectively], 9H, from 2,2-diethoxyethyl —CH(OR)$_2$ group, 2×Fmoc $OCH_2$— groups, 1×$Ar_{styryl}CH_2$N< group, 2× fluorenyl (Ar)$_2$CH— groups), 5.24 (bd, 1H, =C—H), 5.72 (bd, 1H, =C—H), 6.68 (bdd, 1H, =C—H), 6.95-7.15 (2×bd, 2H, ArH), 7.15-7.50 (m, 11H, ArH), 7.58 (t, 3H, ArH), 7.74 (bs, 4H, ArH).

{6-[(9H-Fluoren-9-ylmethoxycarbonyl)-(2-oxoethyl)amino]hexyl}-(4-vinylbenzyl)carbamic acid 9H-fluoren-9-ylmethyl ester, 5c 4c (9.00 g, 11.3 mmol) was dissolved in THF (50 mL), forming a colourless solution, in a 250 mL RB flask. A tip of a microspatula measure of MEHQ was then added to this solution. A 125 mL pressure-equalising addition funnel was connected to this flask and the funnel connected in turn to a nitrogen-vacuum manifold. Separately trifluoroacetic acid (50 mL) and water (17 mL) were mixed together and then placed in the addition funnel and the apparatus was then flushed with nitrogen. The reaction flask was then surrounded with an ice-water cooling bath and the 4c/THF solution cooled to ≤+5 deg C. The TFA/$H_2O$ solution was then added dropwise to the reaction mixture over a period of 1 hour at ≤+5 deg C. The reaction mixture was then allowed to warm slowly to room temperature under nitrogen. This reaction mixture was then stirred at room temperature under a nitrogen atmosphere for a period of 18 hours. The solution contained a small amount of floccular material (polymer) and was filtered in order to remove it. The filtrate and was then stripped to dryness in vacuo using a rotary evaporator yielding several grams of a viscous dark yellow oil which was further dried at higher vacuum (oil immersion pump) for a period of 1 hour at room temperature. This oil was taken up in $CH_2Cl_2$ (100 mL) and extracted with 2×150 mL portions of saturated aqueous $NaHCO_3$ solution and a single 150 mL portion of de-ionised water. The organic layer was then partitioned and separated before being dried over anhydrous $MgSO_4$ for a period of 45 minutes. The drying mixture was then filtered and the collected solid washed with 2×25 mL portions of $CH_2Cl_2$. The filtrate and washings were combined and then stripped to dryness in vacuo using a rotary evaporator to yield a pale yellow viscous oil which was further dried in vacuo (oil immersion pump) at room temperature forming a pale yellow "foam". After 7 hours of drying in vacuo at room temperature the "foam" was broken up with a spatula to yield a pale yellow light powder. Yield: 7.4 g (91%). $^1$H NMR (d$_6$-DMSO, spectrum acquired at 100° C. to reduce spectral complexity caused by conformation stereoisomerism) δ 1.00 (bs, 4H, hexamethylene bridge —CH$_2$—), 1.44 (bs, 4H, hexamethylene bridge —CH$_2$—), 2.99 (t, 2H, hexamethylene bridge >NCH$_2$—), 3.07 (t, 2H, hexamethylene bridge >NCH$_2$—), 3.88 (s, 2H, >NCH$_2$C(=O)), 4.27 (m, 4H, 2× fluorenyl (Ar)$_2$CH— and Ar$_{styryl}$CH$_2$N<), 4.48 (d, 2H, Fmoc OCH$_2$—), 4.55 (d, 2H, Fmoc OCH$_2$—), 5.23 (d, 1H, =C—H), 5.75 (d, 1H, =C—H), 6.72 (dd, 1H, =C—H), 7.06 (d, 2H, ArH), 7.35 (m, 10H, ArH), 7.60 (m, 4H, ArH), 7.83 (d, 4H, ArH), 9.37 (s, 1H, —CH(=O)).

[2-(6,8-Bis-diisobutylsulfamoylpyren-1-ylamino)ethyl]-{6-[(9H-fluoren-9-ylmethoxycarbonyl)-(4-vinyl-benzyl)amino]-hexyl}carbamic acid 9H-fluoren-9-ylmethyl ester, 6c Into a 100 mL 3-neck RB flask was weighed 5c (0.43 g, 0.598 mmol) and 6-aminopyrene-1,3-disulfonic acid bis-diisobutylamide, 1a from Example 1 (0.33 g, 0.550 mmol). One side-arm of the flask was stoppered and the second was suba-sealed and the centre socket attached to a double-layer coil condenser which in turn was connected to a nitrogen-vacuum manifold. The apparatus was purge-filled with nitrogen and then 1,2-dichloroethane (20 mL, anhydrous) was added to the flask via a Hamilton gastight syringe. A single crystal of MEHQ was added to the mixture which was then magnetically stirred whilst being gently warmed with a heat-gun until all the solids had dissolved, to form a bright orange solution, bar a small amount of white floccular material. The reaction mixture was then stirred at room temperature under a nitrogen atmosphere for a period of 3 hours to allow formation of the imine intermediate to proceed. After 3 hours sodium triacetoxyborohydride (0.22 g, 1.04 mmol) was added to the reaction mixture followed by acetic acid (0.030 mL, 0.5240 mmol). The reaction mixture was then stirred at room temperature for a period of 65 hours at room temperature. CH$_2$Cl$_2$ (50 mL) was then added to the mixture, which was then quenched with saturated aqueous NaHCO$_3$ solution (100 mL). This mixture was then transferred to a 250 mL-separating funnel and the layers partitioned and separated and the organic layer was extracted with a further 100 mL of saturated aqueous NaHCO$_3$ and then 100 mL of brine. The organic layer was then partitioned and separated and then dried over anhydrous Na$_2$SO$_4$ for a period of 1 hour. An aliquot of the reaction mixture was then removed and analysed by TLC (eluant mixture: 1% TEA/59% n-hexane/40% EtOAc) alongside the 1a starting material, unfortunately this seemed to indicate that none of the fluorophore had reacted with the aldehyde as the fluorescent species in the reaction mixture moved at exactly the same rate as 1a. The crude product solution was then stripped to dryness in vacuo using a rotary evaporator to yield a red-orange "glass". This material was then purified by flash chromatography using an eluant mixture of 1% TEA/59% n-hexane/40% EtOAc using a 40 mm diameter flash column. The crude product tailed excessively on the column so that even after 40×30 mL fractions had been collected the fractions were still brightly fluorescent. Consequently two more large 400 mL fractions were collected in order to try and "wash" all the material from the column. All the fractions were then analysed by TLC using a eluant mixture of 1% TEA/59% n-hexane/40% EtOAc. Fractions' 1-17 were discarded, and fractions' 18-21, 22-24, 24-28, 29-40 were combined to make four "master" fractions, all of which exhibited one peak on TLC with the same Rf as the 1a fluorophore starting material. TLC analysis of the first 400 mL column "wash" indicated that it contained a significant amount of material (consisting of three peaks) and was therefore retained whereas the second 400 mL column wash did not contain a significant amount of material and so was discarded. All of the five remaining "master" fractions were stripped down and it was noticed at this point that fractions' 18-21, 22-24, and 24-28 yielded a beautiful bright orange "foam" (which was broken up with a spatula to a powder), fractions' 29-40 yielded a dull orange 'hard' crystalline powder which looked remarkably similar to the starting 1a fluorophore, and the impure first 400 mL column wash fraction yielded an orange foam (again broken up to a powder). 20 mg of fraction 21-24 was dispatched for $^1$H NMR (CDCl$_3$) characterisation which remarkably seemed to indicate that it contained the desired product in good purity. It was therefore decided to combine all the similar looking 18-28 fractions to yield 175 mg of a bright orange powder, fraction 29-40 (170 mg) was retained as was the first 400 mL column wash (185 mg) and these three batches of material were dispatched for HPLC-MS. The HPLC-MS data indicated that fractions' 18-28 contained the desired product, 6c, in ca. 95% purity. Yield: 0.175 g (24.4%, red-orange microcrystalline solid). $^1$H NMR (CDCl$_3$) δ 0.79 (d, 24H, pyrene isobutyl —CH$_3$), 0.93-1.54 (bm, 8H, hexamethylene bridge —CH$_2$—), 1.90 (m, 4H, pyrene isobutyl —CH<), 2.99 (bs, 2H, hexamethylene bridge >NCH$_2$—), 3.08-3.31 (overlapping m and bs, 10H, pyrene isobutyl —N(CH$_2$—)$_2$ [m] and hexamethylene bridge >NCH$_2$— [bs]), 3.49 (bs, 2H, Ar$_{pyrene}$NHCH$_2$—), 3.69 (bs, 2H, —(O=C)NCH$_2$—), 4.21 (t, 2H, 2× fluorenyl (Ar)$_2$CH—), 4.38 (bd, 2H, Fmoc OCH$_2$—), 4.53 (bd, 2H, Fmoc OCH$_2$—), 4.67 (d, 2H, Ar$_{styryl}$CH$_2$N<), 5.23 (d, 1H, =C—H), 5.72 (d, 1H, =C—H), 6.69 (dd, 1H, =C—H), 6.96-7.47 (overlapping m, 14H, ArH), 7.48-7.62 (overlapping d and bs, 3H, ArH), 7.63-7.76 (m, 4H, ArH), 8.08-8.20 (m, 2H, pyrene ArH), 8.35 (bd, 1H, pyrene ArH), 8.58 (d, 1H, pyrene ArH), 8.82 (bd, 1H, pyrene ArH), 9.07 (s, 1H, pyrene-7H ArH).

6-{2-[6-(4-Vinylbenzylamino)hexylamino]ethylamino}pyrene-1,3-disulfonic acid bis-diisobutylamide, 7c 6c (0.155 g, 0.1190 mmol) was dissolved in 2.5 mL of THF in a 50 mL B24 RB flask forming a bright orange solution. The flask was attached to a nitrogen line and flushed with nitrogen for a period of 20 minutes before 1-octanethiol (0.41 mL, 2.358 mmol) was added followed by DBU (0.018 mL, 0.12 mmol) which caused an instant colour change from orange to dark green together with the development of a slight turbidity. This dark colouration and the turbidity then quickly faded and the solution regained its orange colouration (slightly darker than before). The reaction mixture was then stirred at room temperature under nitrogen for a period of 90 minutes. The reaction mixture was then stripped to dryness in vacuo using a rotary evaporator before n-hexane (15 mL) was added to the orange oil residue causing the formation of a turbid orange solution and the deposition of a dark red "glass". The supernatant was decanted off and the "glass" treated with another portion of n-hexane (15 mL) which was then decanted off. The n-hexane supernatant layers were combined and stripped to dryness in vacuo using a rotary evaporator to yield an orange oil. The dark red "glass" and the orange oil were analysed by TLC (eluant mixture: 1% TEA/10% MeOH/89% $CH_2Cl_2$), both batches contained a large amount of a slow moving tailing spot at Rf: 0.2 with some components at the solvent front, presumably trace 1a starting material and the octanethiol-adduct of dibenzofulvene (only visible under $UV_{254}$ illumination). The two batches of material were then combined and purified by dry-column flash chromatography using a 40 mm diameter, 50 mm depth 10-20 μm porosity sinter and eluting with 25 mL fractions comprising: (i) 0-100% $CH_2Cl_2$/100-0% n-hexane in 25% increments; (ii) 2% TEA/0-50% MeOH/98-48% $CH_2Cl_2$ in 5% increments with each fraction eluted for a period of 4 minutes. A tight well-defined strongly fluorescent band was observed to move down the column and eluted on fraction 10 yielding a brown solution. Foaming under the sinter and fluorescence was observed on elution of fractions' 9-11 from the column and fractions' 12-16 exhibited a pale green colouration. Subsequent TLC analysis of fractions' 9-16 indicated that the product was contained overwhelmingly within fraction 10. Fractions' 9 and 11-16 were combined and stripped to dryness which confirmed that they contained only a small amount of material. Fraction 10 was evaporated to dryness in vacuo using a rotary evaporator and found to contain a significant amount of a bright red-orange material that was then dried in vacuo (oil immersion pump) overnight at room temperature. The resultant red-orange glass was then scraped from the walls of the flask using a spatula to yield a bright red-orange powder. Yield: 0.076 g (74.4%). $^1$H NMR ($CDCl_3$) δ 0.73 (t, 24H, pyrene isobutyl —$CH_3$), 1.08 (bs, 4H, hexamethylene bridge —$CH_2$—), 1.46 (bs, 4H, hexamethylene bridge —$CH_2$—), 1.86 (m, 4H, pyrene isobutyl —CH<), 2.54 (bt, 2H, hexamethylene bridge >$NCH_2$—), 2.70 (bt, 2H, hexamethylene bridge >$NCH_2$—), 2.84 (m, 2H, diethylene bridge >$NCH_2$—), 3.12 (d, 8H, pyrene isobutyl —N($CH_2$—)$_2$), 3.25 (bs, 2H, diethylene bridge —$CH_2Ar_{pyrene}$), 3.73 (bs, 2H, hexamethylenediamine bridge —$NH_2$), 3.86 (s, 2H, $Ar_{styryl}CH_2N<$), 5.18 (d, 1H, =C—H), 5.65 (d, 1H, =C—H), 6.62 (dd, 1H, =C—H), 7.22-7.40 (overlapping m, 5H, 1× pyrene ArH and 4× styryl ArH), 8.07 (d, 2H, pyrene ArH), 8.53 (d, 1H, pyrene ArH), 8.75 (overlapping bs and m, 2H, 2× pyrene ArH), 9.00 (s, 1H, pyrene-7H ArH). MS (accurate mass): Parent molecular ion ($^1H^+$ adduct); $C_{49}H_{72}N_5O_4{}^{32}S_2{}^+$-theoretical m/z: 858.50203, observed m/z: 858.50297, Δ (ppm): 1.10.

6-[2-([2-(boronic acid)benzyl]-{6-[[2-(boronic acid)benzyl]-(4-vinylbenzyl)amino]hexyl}amino)-ethylamino]pyrene-1,3-disulfonic acid bis-diisobutylamide, 8c Into a 5 mL RB flask was placed a small egg shaped magnetic stirrer follower, 7c (0.070 g, 0.08156 mmol) and 2-(bromomethyl)phenyl boronic acid pinacol ester (0.073 g, 0.2458 mmol) and a single crystal of phenothiazine (polymerisation inhibitor). The flask was then attached to a Claisen head and its vertical joint connected to a screw-thread cap with PTFE-liner and its side-arm was connected to a microcoil condenser and this in turn connected to a cone-hose adapter attached to a vacuum-nitrogen manifold. The apparatus was then purge-filled with nitrogen three times before dichloromethane (anhydrous, 1.50 mL) was added to the reaction flask via a 2.5 mL Hamilton gastight syringe through the PTFE-liner quickly dissolving the solids to form an orange solution with a green fluorescent meniscus. Then DIPEA (0.058 mL, 0.3327 mmol) was quickly added to the reaction mixture using a 0.200 mL digital pipette. The reaction mixture was then stirred at room temperature under nitrogen for a period of 10 minutes. The reaction flask was then wrapped in aluminium foil and stirred at room temperature for a period of 24 hours under nitrogen. After 24 hours a 0.50 mL aliquot of the reaction mixture was removed and pipette-filtered through a glass microfibre plug. The clear yellow-orange filtrate was then sub-divided into four samples (3×0.05 mL and 1×0.35 mL) and each of these was spun down using a rotary evaporator and the yellow-orange oil residue then further dried in vacuo (0.20 torr) in a desiccator for a period of 45 minutes at room temperature. The flask containing the remaining 3 mL of the reaction mixture was then sealed up and placed in a freezer at −20° C. One of the 0.05 mL samples was then dispatched for HPLC analysis which indicated the desired product, 6-[2-([2-(4,4,5,5-tetramethyl-[1,3,2]dioxaborolan-2-yl)benzyl]-{6-[[2-(4,4,5,5-tetramethyl-[1,3,2]dioxaborolan-2-yl)benzyl]-(4-vinyl-ben-zyl)amino]hexyl}amino)ethylamino]pyrene-1,3-disulfonic acid bis-diisobutyl amide had formed. The remaining reaction mixture was therefore removed from cold storage and stripped to dryness in vacuo and subjected to a preparative HPLC purification step, which caused the pinacol boronate ester groups of the crude product to cleave to the free boronic acids, thus forming the desired final product, 8c. Yield: 6.5 mg (6.2%, red-orange microcrystalline solid). $^1$H NMR ($CDCl_3$, this $^1$H NMR was complicated by the presence of a small amount of other x,y-bis(diisobutylsulfonamido)pyrene isomers in addition to the major 1,3-bis(sulfonamido)-pyrene isomer. These minor isomeric contributions have been discounted from the following $^1$H NMR summary for the purpose of simplification) δ 0.78 (m, 24H, pyrene isobutyl —$CH_3$), 1.072 (bs, 4H, hexamethylene bridge —$CH_2$—), 1.41 (bs, 4H, hexamethylene bridge —$CH_2$—), 1.90 (m, 4H, pyrene isobutyl —CH<), 2.32 (bt, 2H, hexamethylene bridge >$NCH_2$—), 2.58 (bt, 2H, hexamethylene bridge >$NCH_2$—), 2.99 (bs, 2H, diethylene bridge >$NCH_2$—), 3.16 (d, 8H, pyrene isobutyl —N($CH_2$—)$_2$), 3.39 (s, 2H, $Ar_{styryl}CH_2N<$), 3.51 (s, 1H, $H^A$ of stereoisomeric boronic acid ArC($H^A$)($H^B$)N<), 3.61 (bs, 2H, diethylene bridge —$CH_2Ar_{pyrene}$), 3.66 (s, 2H, non-stereoisomeric boronic acid Ar$CH_2$N<), 3.82 (s, 1H, $H^B$ of stereoisomeric boronic acid ArC($H^A$)($H^B$)N<), 5.22 (d, 1H, =C—H), 5.70 (d, 1H, =C—H), 6.67 (dd, 1H, =C—H), 7.05-7.38 (overlapping m, 11H, ArH), 7.79 (bd, 2H, ArH), 8.17 (d, 2H, pyrene ArH), 8.58 (dd, 2H, pyrene ArH), 8.80 (d, 1H, pyrene ArH), 9.08 (s, 1H, pyrene-7H ArH). MS (accurate mass): Parent molecular ion ($^1H^+$ adduct); $C_{63}H_{86}{}^{11}B_2N_5O_8{}^{32}S_2{}^+$-theoretical m/z: 1126.61038, observed m/z: 1126.61044, Δ (ppm): +0.053.

Example 4

10-({6-[4-(2-Acryloyloxyethyl)benzyl-(2-{boronic acid}benzyl)-amino]hexyl-(2-{boronic acid}benzyl)amino}methyl)-N-[2-(methoxy)ethyl]-anthracene-1,9-dicarboxylic imide A fluorescent sensor compound comprising the fluorophore of Example 2 was prepared according to the following method:

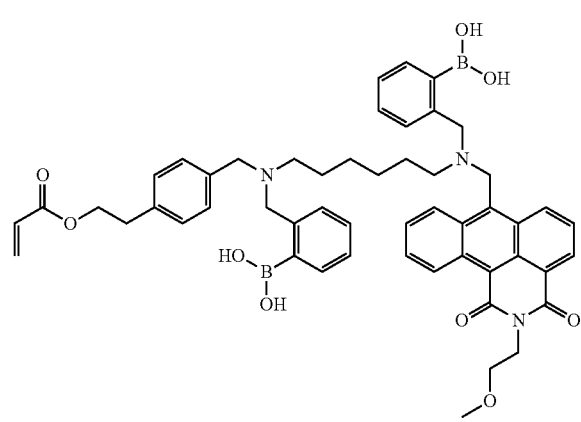

7d

6-(tert-Butoxycarbonylamino)hexylamine, 1d tert-Butyl phenyl carbonate (25.60 mL, 138.0 mmoles) was added to a stirred solution of 1,6-diaminohexane (15.30 g, 131.7 mmoles) in absolute EtOH (150 mL) in a 250 mL RB flask. The apparatus was fitted with a condenser and heated to 78° C. overnight under a blanket of nitrogen and then allowed to cool to room temperature. The solvent was stripped off the reaction mixture in vacuo (rotary evaporator) yielding a pale pink oily residue. $CH_2Cl_2$ (200 mL) was added to the residue and the resultant solution extracted with 3×200 mL portions of de-ionised water. For each extraction the pH of the aqueous phase was monitored and adjusted with HCl (aq, 2M) such that the pH of the aqueous layer was 3<pH<7 [only required for 1st extraction, needing ca. 60-70 mL HCl (aq, 2M)]. The aqueous phases were collected in a Erlenmeyer flask containing aqueous NaOH (aq, 100 mL, 3M). Ensuring that the pH of the collected aqueous extracts was ≥14 the resulting aqueous phase was extracted with $CH_2Cl_2$ (3×150 mL). These organic phases were recombined, evaporated to a volume of ca. 200 mL and subjected to the above pH modulated purification protocol for a second time by first extracting with water [3×200 mL, 3<pH<7 modulation with HCl (aq, 2M), again only required for 1st extract needing ca. 45-55 mL HCl (aq, 2M)], basifying these aqueous extracts with NaOH (100 mL, 3M) and extracting with $CH_2Cl_2$ (3×150 mL). The $CH_2Cl_2$ extracts were combined, reduced in volume to 200 mL and then dried over anhydrous $MgSO_4$, filtered, and stripped to dryness on a rotary evaporator for a period of 20 minutes to yield 6-(tert-butoxycarbonylamino)hexylamine as a peach oil. This peach oil was then subjected to a short path distillation using a Kugelrohr apparatus with an oven temperature of 180° C. and at a vacuum pressure of 0.160 torr, the receiver bulb was cooled by means of a dry-ice/acetone bath. Yield: 13.1 g (46%, colourless oil). $^1$H NMR ($CDCl_3$) δ 1.14 (s, 2H, —$NH_2$), 1.26-1.37 (m, 4H, —$CH_2$—), 1.37-1.52 (s+m, 9H+4H, t-Bu+—$CH_2$—), 2.67 (t, 2H, >$NCH_2$—), 3.09 (q, 2H, —C(=O)$NCH_2$—), 4.60 (bs, 1H, —C(=O)NH—).

2-(4-Bromophenethyloxy)tetrahydro-2H-pyran, 2d

Into 30 mL of $CH_2Cl_2$ in a 150 mL RB flask was dissolved 4-bromophenethyl alcohol (7.00 g, 34.80 mmol) and 3,4-dihydro-2H-pyran (3.80 mL, 41.61 mmol). To this solution was added a few crystals of p-toluenesulfonic acid monohydrate. The reaction mixture was then stirred at room temperature under a blanket of nitrogen overnight. Overnight the reaction mixture changed colour again to a deep brown colour. The reaction mixture was transferred to a 250 mL separating funnel and extracted with 150 mL of saturated $NaHCO_3$(aq) solution during which time the brown colouration in the organic layer faded to an orange colour. The layers were separated and the organic layer was extracted again with 150 mL of brine. The organic layer was then separated and dried over anhydrous $MgSO_4$ for 1 hour at room temperature. The mixture was then filtered and the collected solid washed with 3×30 mL portions of $CH_2Cl_2$. The filtrate and washings were combined and stripped to dryness on a rotary evaporator to yield an orange oil. Column chromatographic conditions for the remainder of the crude product were determined by TLC analysis (10% EtOAc/90% n-hexane eluant) which indicated a major spot at $R_f$ 0.5 with a few minor spots on and around the baseline. The crude product was then purified by dry column flash chromatography using a sinter of 80 mm diameter and 80 mm depth packed to a depth of 5.5 cm with Merck 60 (15-40 μm) silica gel, time per fraction: 4.00 minutes, crude product pre-loaded onto 12.5 g of Merck 60 (15-40 □m) and this loaded on top of the column. n-Hexane/EtOAc elution in 100 mL fractions with the EtOAc component increasing in 1% increments from 0% (fraction 1) to 15% (fraction 16). Fractions' 9 & 10 "foamed" on leaving the column and TLC (10% EtOAc/90% n-hexane) of fractions' 8-15 indicated pure product was contained in fractions' 9-12 and these were combined and stripped to dryness on a rotary evaporator before being further dried in vacuo (oil immersion pump) overnight at room temperature. Yield: 9.821 g (98.9%, colourless liquid). $^1$H NMR ($CDCl_3$) δ 1.40-1.88 (m, 6H, [3×—$CH_2$—]$_{pyran}$), 2.86 (t, 2H, $ArCH_2$—), 3.45 (m, 1H, [$OCH_aH_b$-]$_{pyran}$), 3.58 (q, 1H, —$O_{pyran}CH_aH_b$—), 3.73 (m, 1H, [$OCH_aH_b$-]$_{pyran}$), 3.92 (q, 1H, —$O_{pyran}CH_aH_b$—), 4.57 (m, 1H, [—OCHO-]$_{pyran}$), 7.10 (d, 2H, ArH), 7.40 (d, 2H, ArH).

4-(2-(tetrahydro-2H-pyran-2-yloxy)ethyl)benzaldehyde, 3d

Magnesium turnings (0.97 g, 39.9 mmol) were weighed into a 250 mL 3-neck RB flask which was then suba-sealed (side-arm), connected to a 100 mL pressure-equalising addition funnel (centre-socket), connected to a double-layer coil condenser (side-arm) which in turn was connected to a nitrogen-vacuum manifold and the apparatus purge-filled with nitrogen three times. Separately 2d (9.50 g, 33.3 mmol) was weighed into a 100 mL RB flask which was then attached to a nitrogen-vacuum manifold and purge-filled with nitrogen before THF (anhydrous, 60 mL) was cannula-transferred into the flask forming a colourless solution. This solution was then cannula transferred into the pressure-equalising addition funnel. Ethyl bromide (0.274 mL) was then "dripped" over the magnesium turnings in the reaction flask using a 1.0 mL Hamilton gastight syringe. The 2d/THF solution was then added dropwise to the reaction mixture and after about 5 mL had added the reaction flask was continually heated by means of a silicone heating oil bath (bath T: 85° C.) until reflux started. After the completion of the addition of 2d/THF (about 30-45 minutes) the reflux was maintained by means of the silicone heating oil bath for a period of 75 minutes before the reaction mixture was allowed to cool to room temperature. After this period the reaction mixture consisted of a deep orange solution containing some residual flakes of magnesium. The reaction flask was then surrounded with a water-ice/methanol-water cooling mixture and the reaction mixture chilled for a period of 5 minutes prior to DMF (anhydrous, 3.00 mL) being added to the reaction mixture in a single portion via a 5 mL Hamilton gastight syringe. The reaction mixture in the cooling bath was then stirred whilst being allowed to warm slowly to room temperature overnight. Next day the (melted) cooling bath was removed and the reaction mixture was allowed to stir at room temperature under nitrogen for a further 24 hours. After 24 hours the reaction mixture was quenched by dropwise addition of 60 mL of saturated aqueous NH$_4$Cl, which initially caused the deposition of a dense white precipitate (magnesium hydroxides) which then dissolved as the addition continued. Post quenching the reaction mixture consisted of a lower nearly colourless aqueous layer and an upper deep yellow organic layer together with a few shards of magnesium turning. This mixture was then filtered directly into a 250 mL-separating funnel and the layers partitioned and separated. The aqueous layer was then extracted with 100 mL of Et$_2$O and these extracts combined with the organic layer from the reaction mixture. The organic extracts were then dried over anhydrous MgSO$_4$ for a period of 90 minutes before the drying mixture was filtered and the collected solid washed with 3×25 mL portions of Et$_2$O. The filtrate and washings were then combined and stripped to dryness in vacuo (rotary evaporator) to yield a pale yellow oil. A small aliquot of the crude product was analysed by TLC (silica-gel TLC plates, 20% EtOAc/80% n-hexane elution mixture) against the 2d starting material which indicated that all of the starting material had reacted to form a new highly tailed major spot with an $R_f$ of 0.52 with additional minor spots at $R_f$ values of 0.09 and 0.0 (baseline). The crude product was then pre-loaded onto 11.0 g of Merck 60 (15-40 μm) silica gel purified by dry column flash chromatography: (i) Sinter size: 80 mm diameter/column packed to a depth of 55 mm with Merck and crude product/silica amalgam packed on top of this; (ii) time per fraction: 3.00 minutes; (iii) Fraction size: 100 mL; (iv) Elution gradient: % Volume n-hexane: 100-62% in 2% increments/% Volume EtOAc: 0-38% in 2% increments (20 fractions in total). After elution of the column fractions' 10-17 were analysed by TLC (20% EtOAc/80% n-hexane) which indicated that most of the product was contained within fractions' 11-14 but fractions' 10 and 15 also contained some material (product highly tailed on the column, common property of aldehyde containing compounds) therefore fractions' 10-15 were combined and stripped to dryness in vacuo (rotary evaporator) to yield a pale yellow liquid which was then further dried in vacuo (oil immersion pump) at room temperature for a period of 4 hours. Yield: 5.878 g (75.3%, yellow liquid). $^1$H NMR (CDCl$_3$) δ 1.40-1.87 (m, 6H, [3×—CH$_2$—]$_{pyran}$), 2.98 (t, 2H, ArCH$_2$), 3.45 (m, 1H, [OCH$_a$H$_b$—]$_{pyran}$), 3.70 (q+m, 2H, —O$_{pyran}$CH$_a$H$_b$— & [OCH$_a$H$_b$-]$_{pyran}$), 3.97 (q, 1H, —O$_{pyran}$CH$_a$H$_b$), 4.58 (m, 1H, [—OCHO-]$_{pyran}$), 7.41 (d, 2H, ArH), 7.82 (d, 2H, ArH), 9.98 (s, 1H, ArCHO).

tert-Butyl 6-(4-(2-(tetrahydro-2H-pyran-2-yloxy) ethyl)benzylamino)hexyl-carbamate, 4d Freshly distilled 1d (5.80 g, 24.8 mmol) was weighed into a 250 mL 3-neck RB flask. Separately 3d (5.878 g, 25.17 mmol) was dissolved in 50 mL of absolute EtOH and the resultant solution added to the 250 mL RB reaction flask and the flask that contained 3d was washed out with 2×15 mL portions of absolute EtOH into the reaction flask. The reaction flask was then stoppered (side-arms) and attached to a double-layer coil condenser (centre-socket) which in turn was connected to a nitrogen-vacuum manifold and the apparatus then flushed with nitrogen. The reaction mixture was then stirred at room temperature under nitrogen overnight (19 hours). Next day 3-(diethylene-triamino)propyl-functiona- lised silica gel (5.84 g, 1.23 mmol/g loading) was added to the reaction mixture which was stirred at room temperature under nitrogen for a period of 6 hours in order to scavenge the excess 3d. Sodium borohydride (1.87 g, 49.4 mmol) was then added to the reaction mixture in a single portion and the mixture then stirred at room temperature overnight under an inert nitrogen atmosphere. Next day the reaction mixture was transferred to two balanced centrifuge tubes and spun down at a rate of 9000 rpm for a period of 10 minutes, the supernatant liquid was then decanted from the centrifuged solid (silica-gel) into a 500 mL florentine flask. The solid in each tube was then re-suspended in fresh EtOH (ca. 40 mL) and again spun down at 9000 rpm for 10 minutes and the supernatant liquid decanted into the evaporation flask before this process was repeated once more. The combined reaction mixture/washes was then concentrated in vacuo (rotary evaporator). De-ionised water (100 mL) was added to the residue in the evaporation flask forming a white emulsion. CH$_2$Cl$_2$ (100 mL) was added to the evaporation flask dissolving the white emulsion and forming two layers, aqueous and organic. The mixture was transferred to a 250 mL-separating funnel and shaken vigorously, the layer allowed to partition and then separated. The aqueous layer was then extracted with a further 2×100 mL portions of CH$_2$Cl$_2$, the layers partitioned and separated. The extracts were then combined and dried over anhydrous Na$_2$SO$_4$ for a period of 45 minutes before being filtered and the collected drying agent washed with 3×30 mL portions of CH$_2$Cl$_2$. The filtrate and washings were combined and stripped to dryness in vacuo (rotary evaporator) to yield a pale yellow colourless oil. A small aliquot of this material was analysed by TLC (10% MeOH/90% CHCl$_3$) which indicated one dominant spot (rather faint and "crescent" shaped) at an $R_f$ of ca. 0.55 with no other visible spot. This crude product was pre-loaded onto 12 g of Merck 60 (15-40 μm) silica gel and loaded onto a 80 mm diameter sinter loaded with Merck 60 (15-40 μm) silica gel to a depth of 57 mm. The column was then eluted using the following parameters: (i) time per fraction: 3.00 minutes; (ii) fraction volumes: 100 mL; (iii) elution gradient: 100-87% CHCl$_3$ in 1% increments/0-13% MeOH in 1% increments (14 fractions). Fractions' 8-10 were a very pale "off-yellow" colour. Fractions' 8-11 were combined and stripped to dryness in vacuo (rotary evaporator) to yield a yellow oil which was then dried in vacuo (oil immersion pump) at 60° C. for a period of 6 hours. Yield: 9.438 g (87.7%, pale yellow oil). $^1$H NMR (CDCl$_3$) δ 1.26-1.88 (s+m, 23H, [—C(CH$_3$)$_3$]$_{Boc}$ & [3×—CH$_2$—]$_{pyran}$ & [4×—CH$_2$-]$_{hexamethylene}$], 2.60 (t, 2H, >NCH$_2$—), 2.90 (t, 2H, ArCH$_2$—), 3.09 (q, 2H, BocNHCH$_2$—), 3.45 (m, 1H, [OCH$_a$H$_b$-]$_{pyran}$), 3.60 (m, 1H, —O$_{pyran}$CH$_a$H$_b$—), 3.75 (s+m, 3H, ArCH$_2$N< & [OCH$_a$H$_b$-]$_{pyran}$), 3.93 (m, 1H, —O$_{pyran}$CH$_a$H$_b$), 4.50 (bs, 1H, BocNH—), 4.60 (m, 1H, [—OCHO-]$_{pyran}$), 7.17-7.27 (m, 4H, ArH).

2-(4-((6-Aminohexylamino)methyl)phenyl)ethanol hydrochloride, 5d

A 250 mL florentine flask containing 4d (9.438 g, 21.72 mmol) was attached to a 250 mL pressure-equalising addition funnel which was connected in turn to a nitrogen line and the apparatus then flushed with nitrogen. Hydrogen chloride in methanol (1.25M, 131 mL) was then poured into the addition funnel. The pear-shaped flask was then surrounded with an ice/water cooling bath and the HCl-MeOH solution was added dropwise to 4d over a period of ca. 1 hour.

The reaction mixture was then allowed to slowly warm to room temperature overnight whilst being vigorously stirred. Next day the solvent was stripped from the mixture in vacuo using a rotary evaporator yielding a white solid which was further dried in vacuo (oil immersion pump) at room temperature for a period of 60 minutes. Et$_2$O (120 mL) was added to the flask causing the deposition of more bright white solid. The solid on the walls of the flask was removed by ultrasound agitation. The solid was then collected by filtration and washed with 2×30 mL portions of Et$_2$O and then dried in vacuo (oil immersion pump) for a period of 6 hours at room temperature. Yield: 6.70 g (95.4%, bright white microcrystalline solid). $^1$H NMR (CDCl$_3$) δ 1.42 (m, 4H, [2×—CH$_2$-]$_{hexamethylene}$), 1.70 (m, 4H, [2×—CH$_2$-]$_{hexamethylene}$), 2.91 (m, 2H, ArCH$_2$—), 2.97-3.13 (t+t, 4H, $^+$NH$_2$CH$_2$— & H$_3$$^+$NCH$_2$—), 3.88 (t, 2H, —CH$_2$OH), 4.23 (s, 2H, ArCH$_2$N), 7.37-7.48 (m, 4H, ArH).

10-({6-[4-(2-Hydroxyethyl)benzylamino] hexylamino}methyl)-N-[2-(methoxy)ethyl]-anthracene-1,9-dicarboxylic imide, 6d 10-Formyl-N-[2-(methoxy)ethyl]-anthracene-1,9-dicarboxylic imide, 5b from Example 2, (1.017 g, 3.051 mmol) was weighed into a 100 mL 3-neck RB flask that was then stoppered (side-arm and centre-socket) and connected to a double-layer coil condenser (side-arm) that was in turn connected to a nitrogen-vacuum manifold and the apparatus flushed with nitrogen. Separately 5d (1.48 g, 4.58 mmol) was weighed into a 100 mL Erlenmeyer flask and 20 mL of MeOH was added forming a colourless solution. Sodium methoxide (0.500 g, 9.255 mmol) was then added to the colourless 5d/MeOH solution causing the instant deposition of a fine white microcrystalline precipitate (NaCl). This mixture was stirred at room temperature for a period of 5 minutes before being added to the reaction flask in a single portion and the Erlenmeyer flask washed out with 5 mL of MeOH. The reaction mixture was a deep orange suspension due to the limited solubility of 5b in MeOH therefore CH$_2$Cl$_2$ (25 mL) was added to the reaction mixture in a single portion causing most of the orange solid to dissolve forming an orange solution containing a fine white solid (NaCl). The reaction mixture was then brought to reflux under nitrogen overnight before being allowed to cool slowly to room temperature. Glacial acetic acid (2.60 mL) was then added to the reaction mixture via a graduated pipette followed by addition of picoline borane (0.34 g, 3.18 mmol). The reaction mixture was then stirred at room temperature overnight under an inert nitrogen atmosphere. Next day the reaction mixture was concentrated to about one third of its volume by rotary evaporation before saturated NaHCO$_3$(aq) was added to the solution to quench the acetic acid (evinced by vigorous effervescence). The mixture was then further concentrated on the rotary evaporator for a further 60 minutes to remove the last traces of the reaction solvents (CH$_2$Cl$_2$/MeOH) yielding a pale orange aqueous solution with a deep red oil impacted on the walls of the flask. The solution was then transferred to a 250 mL-separating funnel and the oil dissolved in about 75 mL of CH$_2$Cl$_2$ forming a red solution which was added to the separating funnel. The mixture was shaken for 90 seconds and then the layers were allowed to partition and the lower organic layer was decanted off. The aqueous layer was then extracted with 2×40 mL portions of CH$_2$Cl$_2$, each time the layers were allowed to partition and the organic layer decanted off. The organic washings were combined and then dried over anhydrous Na$_2$SO$_4$ for a period of 60 minutes. The drying mixture was then filtered and the collected solid washed with 4×20 mL portions of CH$_2$Cl$_2$. The filtrate and washings were combined before being stripped to dryness in vacuo on a rotary evaporator yielding a deep red oil. A small portion of this oil was analysed by TLC (elution mixture: 2% 7N NH$_3$ in MeOH/5% MeOH/93% CHCl$_3$) which indicated a complex mixture of products from the baseline to the solvent front but with a dominant spot, presumed to be the desired product, at an R$_f$ of 0.27. The crude product was then purified by conventional flash chromatography using a 45 mm diameter column packed with silica-gel (40-63 μm) to a depth of 6 inches. The crude product was dry-loaded onto the column by dissolving the crude product in 50 mL CH$_2$Cl$_2$ and adding 3.5 g of silica-gel (40-63 μm) and stripping the mixture down to dryness and further drying the resultant red powder in vacuo (oil immersion pump) before placing this material on the top of the column, washing down the sides of the column with the elution mixture (2% 7N NH$_3$ in MeOH/5% MeOH/93% CHCl$_3$) and then placing clean sand on top of the packed column to a depth of ⅝". The column was then eluted with 2% 7N NH$_3$ in MeOH/5% MeOH/93% CHCl$_3$ and a column pressure of 5 psi (to give a flow of 2"/min) with 30 mL fractions collected from the point the eluted liquid developed colouration. 30 fractions were collected and these were analysed by TLC (2% 7N NH$_3$ in MeOH/5% MeOH/93% CHCl$_3$) at 2 fraction intervals (i.e. fraction 2, 4, 6, 8, 10, etc). The TLC analysis indicated that fractions' 15-24 contained most of the desired product in reasonably good purity (only slight cross-contamination from higher and lower spots) though fractions' 12-14 and 25-onwards exhibited significant cross-contamination and so were discarded (they also appeared to contain relatively little of the desired product compared to the major product fractions). Fractions' 15-24 were therefore combined and stripped to dryness in vacuo (rotary evaporator) for a period of 1 hour before being further dried in vacuo (oil immersion pump) at a temperature of 60° C. for a period of 4 hours. Yield: 1.406 g (81.2%, deep red viscous oil). $^1$H NMR (CDCl$_3$) δ 1.38 (m, 4H, [2×—CH$_2$-]$_{hexamethylene}$) 1.55 (m, 4H, [2×—CH$_2$-]$_{hexamethylene}$), 2.62 (t, 2H, >NCH$_2$—), 2.85 (m, 4H, >NCH$_2$— & ArCH$_2$—), 3.42 (s, 3H, OCH$_3$), 3.73 (s, 2H, ArCH$_2$N<), 3.83 (m, 4H, —CH$_2$OH & MeOCH$_2$—), 4.55 (t, 2H, [>NCH$_2$—]$_{anthraimide}$), 4.78 (s, 2H, [ArCH$_2$N>]$_{anthraimide}$), 7.18 (d, 2H, ArH), 7.25 (d, 2H, ArH), 7.64-7.84 (m, 3H, [ArH]$_{anthraimide}$), 8.52 (d, 1H, [ArH]$_{anthraimide}$), 8.79 (2×d, 2H, [ArH]$_{anthraimide}$), 10.11 (d, 1H, [ArH]$_{anthraimide}$). ESI-MS (accurate mass): Parent molecular ion ($^1$H$^+$ adduct); C$_{35}$H$_{42}$O$_4$N$_3$$^+$-theoretical m/z: 568.31698, observed m/z: 568.31687, Δ (ppm): −0.20.

10-({6-[4-(2-Acryloyloxyethyl)benzyl-(2-{boronic acid}benzyl)-amino]hexyl-(2-{boronic acid}benzyl) amino}methyl)-N-[2-(methoxy)ethyl]-anthracene-1, 9-dicarboxylic imide, 7d 6d (0.184 g, 0.3241 mmol) was dissolved in 7 mL of anhydrous 1,2-ethylene dichloride (EDC) in 3×2 mL and 1×1 mL portions and these added in sequence to a 25 mL microscale RB flask which was then attached to a Claisen head, which was in turn attached to a water condenser, which in turn was connected to a nitrogen-vacuum manifold. The apparatus was flushed with nitrogen before the 6d in EDC solution was subjected to three cycles of freeze-thaw-degassing. DIPEA (0.34 mL, 1.952 mmol) was then added to the reaction flask via a 0.50 mL Hamilton gastight syringe and then (2-bromomethylphenyl)boronic acid, pinacol ester (0.212 g, 0.7138 mmol) was weighed out and added to the reaction mixture. The reaction flask was then surrounded with a silicone oil bath and heated to reflux under nitrogen (oil bath T: 115° C.) for a period of 6 hours before being allowed to cool to room temperature overnight. Next day the reaction flask was surrounded with an ice/water cooling bath and chilled for 10 minutes before acryloyl chloride (79 μL, 0.9724 mmol) was added to the reaction mixture in a single portion using a digital pipette. The cooling bath was then removed and the reaction mixture was allowed to warm slowly to room temperature under nitrogen. After 30 minutes at room temperature another 79 μL portion of acryloyl was added to the reaction mixture, which was then stirred for 2.5 hours. The reaction mixture was then transferred to a 50 mL-separating funnel and the reaction flask washed out with 2×5 mL portions of $CH_2Cl_2$. The reaction mixture was then extracted with 30 mL of de-ionised water and then 30 mL of saturated $NaHCO_3$(aq) solution. The organic layer was then partitioned and separated and dried over anhydrous $Na_2SO_4$ for a period of 1 hour. The drying mixture was then filtered and washed with 2×20 mL portions of $CH_2Cl_2$. The filtrate and washings were combined and stripped to dryness in vacuo (rotary evaporator) to yield a brown oil which was further dried in vacuo (oil immersion) pump overnight at room temperature. This crude product was then dissolved in MeOH and kept for a period of 4 days in the dark (to effect cleavage of the boronic acid pinacol ester protecting groups) prior to its purification by preparative HPLC using basic column conditions [$(NH_4)_2CO_3$(aq)/MeCN/MeOH-gradient elution] yielding 70 mg of pure, deprotected 7d. Yield: 70 mg (24.3%, red orange microcrystalline solid). $^1$H NMR ($CDCl_3$+2 drops $CD_3OD$) δ 0.95 (bm, 4H, [2×—$CH_2$-$]_{hexamethylene}$), 1.43 (m, 4H, [2×—$CH_2$-$]d_{hexamethylene}$), 2.32 (t, 2H, >$NCH_2$—), 2.44 (t, 2H, >$NCH_2$—), 2.95 (t, 2H, $ArCH_2$—), 3.42 (s, 3H, $OCH_3$), 3.55 (s, 2H, [$ArCH_2$N<$]_{boronic}$), 3.68 (s, 2H, [$ArCH_2$N<$]_{boronic}$), 3.77-3.90* (s+t, 4H, $ArCH_2$N< & $MeOCH_2$—), 4.36 (t, 2H, —$CH_2$OC(=O)—), 4.55 (t, 2H, [>$NCH_2$-$]_{anthraimide}$), 4.62 (s, 2H, [$ArCH_2$N<$]_{anthraimide}$), 5.82 (d, 1H, O(O=)$CCH_s$=$CH_sH_a$), 6.11 (q, 1H, —O(O=)$CCH_s$=$CH_sH_a$), 6.38 (d, 1H, —O(O=)$CCH_s$=$CH_s$=$CH_sH_a$), 7.17 (s, 5H, [ArH$]_{boronic}$), 7.28 (m, 2H, [ArH$]_{linker}$), 7.38 (m, 2H, [ArH$]_{linker}$), 7.64 ($m_{overlapping}$, 2H, [ArH$]_{anthraimide}$), 7.83 ($m_{overlapping}$, 3H, 1×[ArH$]_{anthraimide}$ & 2×[ArH$]_{boronic}$), 8.35 (d, 1H, [ArH$]_{anthraimide}$), 8.48 (d, 1H, [ArH$]_{anthraimide}$), 8.77 (d, 1H, [ArH$]_{anthraimide}$), 10.03 (d, 1H, [ArH$]_{anthraimide}$). [*: partially obscured by $CD_3OD$ solvent peak]. ESI-MS (accurate mass): Parent molecular ion ($^1H^+$ adduct); $C_{52}H_{58}B_2N_3O_9{}^+$-theoretical m/z: 890.43537, observed m/z: 890.43629, Δ (ppm): +1.04.

The present invention has been described with reference to particular embodiments and examples, but it is to be understood that the invention is not limited to these embodiments and examples.

The invention claimed is:
1. A fluorescent sensor compound of formula (Iaa) which is a fluorophore moiety which is bound at position [Rec] to a receptor moiety, either directly or via a $C_1$-$C_6$ alkylene group, wherein the receptor moiety is capable of selectively interacting with an analyte selected from saccharides, amino saccharides, carbonyl saccharides and potassium and wherein the fluorescence of the fluorophore moiety is perturbed upon interaction of the receptor moiety with said analyte:

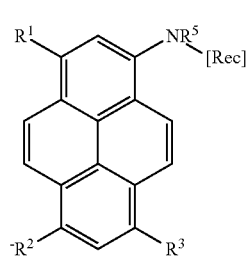

(Iaa)

wherein:
$R^2$ and $R^3$ are the same or different and each represent a hydrogen atom or a group —$SO_2R^6$ wherein $R^6$ represents a chlorine atom or a group of formula —$NR^7R^8$, —$NA^1A^2$, —$NR^7A^1$, $C_{1-6}$ alkyl, $C_{1-6}$ hydroxyalkyl, $C_{2-6}$ alkenyl, $C_{6-10}$ aryl, $C_{6-10}$ aryl($C_{1-6}$)alkyl, halo($C_{1-6}$)alkyl or —OR' where R' is hydrogen or $C_{1-6}$ alkyl;
$R^1$ represents:
a hydrogen or halogen atom;
a group —$SO_2R^6$ where $R^6$ is as defined for $R^2$ and $R^3$;
a group $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, thiocyanate, $C_{1-4}$ hydroxyalkyl, —COH, —COCl, —$CH_2$OR, —$CH_2$NHR, —OR, —NHR, —SR', —NR'R'' or —$N^+$R'R''R''' where R is (meth)acryl, —CO—C($CH_2$)—$CH_3$ or —$CH_2$-Ph-$CH_2$=$CH_2$ and R', R'' and R''' are the same or different and represent hydrogen or unsubstituted $C_{1-2}$ alkyl;
a phosphine, phosphinate, phosphonate, phosphine oxide or phosphonite group;
a group —$COO^-$ or —COOR where R represents hydrogen, $C_{1-6}$ alkyl, $C_{6-10}$ aryl, 5- to 10-membered heteroaryl or 5- to 10-membered heterocyclyl;
a group of formula (A):

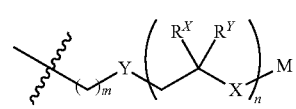

(A)

where m is 0 or 1, X and Y are the same or different and represent —O—, —S— or —NR— where R is hydrogen or $C_{1-4}$ alkyl, n is an integer of from 1 to 20, $R^X$ and $R^Y$ are the same or different and represent hydrogen, $C_{1-6}$ alkyl, $C_{6-10}$ aryl, 5- to 10-membered heteroaryl or 5- to 10-membered heterocyclyl, and M represents hydrogen, (meth)acryl or 4-vinylbenzyl; or
a polymerisable group;
$R^7$ and $R^8$ are the same or different and represent a hydrogen atom or a group selected from $C_{1-10}$ alkyl and $C_{2-10}$ alkenyl;
$A^1$ and $A^2$ are the same or different and represent a phenyl or 5- to 6-membered heteroaryl group;
$R^5$ represents hydrogen, acyl, $C_{1-6}$ alkyl, benzyl, $C_{6-10}$ aryl, 5- to 10-membered heteroaryl or 5- to 10-membered heterocyclyl;
wherein at least one of $R^1$, $R^2$ and $R^3$ is other than hydrogen; and wherein the alkyl, alkenyl, aryl and heteroaryl groups or moieties of $R^6, R^7, R^8, A^1$ and $A^2$ may optionally bear one or more polymerisable groups and/or one or more ionic water-solubilising groups, or the aryl and heteroaryl groups may themselves represent a cyclic ionic water-solubilising substituent;

wherein the pyrene ring may further optionally bear one or more ionic water-solubilising groups and/or one or more polymerisable groups;

wherein a polymerisable group is a group —$R^P$ or -spacer-$R^P$, wherein $R^P$ is a (meth)acrylate, vinylbenzyl, vinylene, (meth)acrylamide, N-vinylamide or allyl group and spacer is a $C_{6-10}$ aryl or $C_{1-10}$ alkylene group or a combination of such aryl and alkylene groups, wherein the alkylene component is optionally interrupted by one or more heteroatoms selected from O, NH and S; and wherein an ionic water-solubilising group is a non-cyclic or cyclic group, the non-cyclic group being selected from sulfonic acid salts, phosphonic acid salts, phosphonium salts, ammonium salts and carboxylate salts, and the cyclic group being selected from (a) $C_{6-10}$ aryl, $C_{3-7}$ carbocyclic, 5- to 10-membered heteroaryl, and 5- to 10-membered heterocyclyl groups each of which is substituted with one or more non-cyclic groups selected from sulfonic acid salts, phosphonic acid salts, phosphonium salts, ammonium salts and carboxylate salts; and (b) pyridinium and imidazolium salts.

2. A fluorescent sensor compound as claimed in claim 1 wherein $R^1$ represents a hydrogen or halogen atom, a group —$SO_2R^6$ or a polymerisable group.

3. A fluorescent sensor compound as claimed in claim 1 wherein:

$R^2$ and $R^3$ are the same or different and each represent a group —$SO_2R^6$ wherein $R^6$ represents a chlorine atom or a group of formula —$NR^7R^8$, —$NA^1A^2$ or —$NR^7A^1$;

$R^7$ and $R^8$ are the same or different and represent a hydrogen atom or a $C_{1-4}$ alkyl group, wherein the alkyl group is unsubstituted or substituted with one or two substituents selected from hydroxyl, —OSiR'R"R''', —NR'R", (meth)acrylate, (meth)acrylamide, vinylbenzyl, N-vinylamide and ionic water-solubilising groups, where R', R" and R''' are the same or different and represent hydrogen or unsubstituted $C_{1-4}$ alkyl;

$A^1$ and $A^2$ are the same or different and represent a phenyl or 5- to 6-membered heteroaryl group, wherein $A^1$ and $A^2$ are unsubstituted or substituted with one or more substituents selected from hydroxyl, $C_{1-4}$hydroxyalkyl, —NR'R", polymerisable groups and ionic water-solubilising groups, where R' and R" are the same or different and represent hydrogen or unsubstituted $C_{1-2}$ alkyl;

wherein the pyrene ring may optionally bear one or more polymerisable groups and/or one or more ionic water solubilising substituents;

wherein an ionic water-solubilising group is selected from sulfonic acid, phosphonic acid, phosphonium, ammonium and carboxylate salts, phenyl groups substituted with a sulfonic acid, phosphonic acid, phosphonium, ammonium or carboxylate salt, and pyridinium and imidazolium salts; and a polymerisable group is a group of formula —$R^P$ or -spacer-$R^P$, wherein spacer is a $C_{1-6}$ alkylene group or a group —($C_{1-6}$ alkylene)-($C_{6-10}$ aryl)-($C_{1-6}$ alkylene)- and $R^P$ is a (meth)acrylate, (meth)acrylamide, vinylbenzyl or N-vinylamide group.

4. A fluorescent sensor compound as claimed in claim 1 wherein $R^1$ is hydrogen, and $R^2$ and $R^3$ are the same or different and represent a group —$SO_2R^6$.

5. A fluorescent sensor compound as claimed in claim 1 wherein $R^5$ represents hydrogen or $C_{1-4}$ alkyl.

6. A fluorescent sensor compound as claimed in claim 1 wherein the receptor moiety of the fluorescent sensor compound comprises one or more binding groups which are capable of binding to the target analyte, said binding group or groups being boronic acid groups.

7. A fluorescent sensor compound as claimed in claim 6 wherein the binding groups of the receptor moiety are separated by an aliphatic spacer moiety, and wherein said spacer moiety is selected from a $C_{1-10}$ alkylene or $C_{3-10}$ carbocyclyl group.

8. A fluorescent sensor compound as claimed in claim 7 wherein the receptor moiety comprises a group of formula (A):

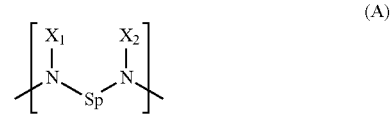

wherein $X_1$ and $X_2$ are the same or different and represent a group -(Alk$^1$)$_n$-$Y_1$ or -(Alk$^1$)$_n$-$Y_2$ respectively where Alk$^1$ is a $C_{1-2}$ alkylene group, n is zero or 1, $Y_1$ and $Y_2$ are the same or different and each represents a boronic acid group, and Sp is the spacer moiety which is selected from $C_{1-10}$ alkylene and $C_{3-10}$ carbocyclyl groups.

9. A fluorescent sensor compound as claimed in claim 8 wherein a spacer group is present between the fluorophore moiety and the receptor moiety of formula (A), and wherein this spacer group is a $C_{1-6}$ alkylene group.

10. A fluorescent sensor compound as claimed in claim 1 wherein at least one group selected from $R^6, R^7, R^8, A^1$ and $A^2$ which is present on $R^1, R^2$ or $R^3$, bears a polymerisable group selected from (meth)acrylate, (meth)acrylamide vinylbenzyl and N-vinylamide groups.

11. A fluorescent sensor compound as claimed in claim 1 wherein the fluorophore moiety is selected from:
6-amino-N1,N1,N3,N3-tetraisobutylpyrene-1,3-disulfonamide;
6-amino-N1,N1,N3,N3-tetrakis(2-hydroxyethyl)pyrene-1,3-disulfonamide;
6-amino-N1,N1,N3,N3-tetrakis(2-(tert-butyldimethylsilyloxy)ethyl)pyrene-1,3-disulfonamide;
6-aminopyrene-1,3-disulfonyl dichloride;
6-(methylamino)pyrene-1,3-disulfonyl dichloride;
N1,N1,N3,N3-tetraisobutyl-6-(methylamino)pyrene-1,3-disulfonamide;
N1,N1,N3,N3-tetrakis(2-hydroxyethyl)-6-(methylamino)pyrene-1,3-disulfonamide; and
N1,N1,N3,N3-tetrakis(2-(tert-butyldimethylsilyloxy)ethyl)-6-(methylamino)pyrene-1,3-disulfonamide;
wherein the fluorophore moiety is bound to [Rec] via the 6-amino group; and from
8-(methylamino)pyrene-1,3,6-trisulfonyl trichloride; and
8-aminopyrene-1,3,6-trisulfonyl trichloride,
wherein the fluorophore moiety is bound to [Rec] via the 8-amino group.

12. A fluorescent sensor compound of formula (Iaa) which is a fluorophore moiety which is bound at position [Rec] to a receptor moiety, either directly or via a $C_1$-$C_6$ alkylene group, wherein the receptor moiety is capable of selectively interacting with an analyte selected from saccharides, amino saccharides, carbonyl saccharides and potassium and wherein the fluorescence of the fluorophore moiety is perturbed upon interaction of the receptor moiety with said analyte:

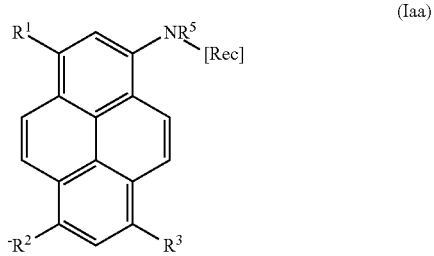

(Iaa)

wherein:
R² and R³ are the same or different and each represent a hydrogen atom or a group —SO₂R⁶ wherein R⁶ represents a chlorine atom or a group of formula —NR⁷R⁸, —NA¹A², —NR⁷A¹, $C_{1-6}$ alkyl, $C_{1-6}$ hydroxyalkyl, $C_{2-6}$ alkenyl, $C_{6-10}$ aryl, $C_{6-10}$ aryl($C_{1-6}$)alkyl, halo($C_{1-6}$)alkyl or —OR' where R' is hydrogen or $C_{1-6}$ alkyl;
R¹ represents:
a hydrogen or halogen atom;
a group —SO₂R⁶ where R⁶ is as defined for R² and R³;
a group $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, cyano, nitro, thiocyanate, $C_{1-4}$ hydroxyalkyl, —COH, —COCl, —CH₂OR, —CH₂NHR, —OR, —NHR, —SR', —NR'R'' or —N⁺R'R'' R''' where R is (meth)acryl, —CO—C(CH₂)—CH₃ or —CH₂-Ph-CH₂=CH₂ and R', R'' and R''' are the same or different and represent hydrogen or unsubstituted $C_{1-2}$ alkyl;
a phosphine, phosphinate, phosphonate, phosphine oxide or phosphonite group;
a group —COO⁻ or —COOR where R represents hydrogen, $C_{1-6}$ alkyl, $C_{6-10}$ aryl, 5- to 10-membered heteroaryl or 5- to 10-membered heterocyclyl;
a group of formula (A):

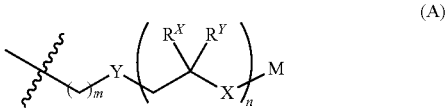

(A)

where m is 0 or 1, X and Y are the same or different and represent —O—, —S— or —NR— where R is hydrogen or $C_{1-4}$ alkyl, n is an integer of from 1 to 20, $R^X$ and $R^Y$ are the same or different and represent hydrogen, $C_{1-6}$ alkyl, $C_{6-10}$ aryl, 5- to 10-membered heteroaryl or 5- to 10-membered heterocyclyl, and M represents hydrogen, (meth)acryl or 4-vinylbenzyl; or
a polymerisable group;

R⁷ and R⁸ are the same or different and represent a hydrogen atom or a group selected from $C_{1-10}$ alkyl and $C_{2-10}$ alkenyl;
A¹ and A² are the same or different and represent a phenyl or 5- to 6-membered heteroaryl group;
R⁵ represents hydrogen, acyl, $C_{1-6}$ alkyl, benzyl, $C_{6-10}$ aryl, 5- to 10-membered heteroaryl or 5- to 10-membered heterocyclyl;
wherein at least one of R¹, R² and R³ is other than hydrogen; and
wherein the alkyl, alkenyl, aryl and heteroaryl groups or moieties of R⁶, R⁷, R⁸, A¹ and A² may optionally bear one or more polymerisable groups and/or one or more ionic water-solubilising groups, or the aryl and heteroaryl groups may themselves represent a cyclic ionic water-solubilising substituent;
wherein the pyrene ring may further optionally bear one or more ionic water-solubilising groups and/or one or more polymerisable groups;
wherein a polymerisable group is a group —$R^P$ or -spacer-$R^P$, wherein $R^P$ is a (meth)acrylate, vinylbenzyl, vinylene, (meth)acrylamide, N-vinylamide or allyl group and spacer is a $C_{6-10}$ aryl or $C_{1-10}$ alkylene group or a combination of such aryl and alkylene groups, wherein the alkylene component is optionally interrupted by one or more heteroatoms selected from O, NH and S; and
wherein an ionic water-solubilising group is a non-cyclic or cyclic group, the non-cyclic groups being selected from sulfonic acid salts, phosphonic acid salts, phosphonium salts, ammonium salts and carboxylate salts, and the cyclic groups being selected from (a) $C_{6-10}$ aryl, $C_{3-7}$ carbocyclic, 5- to 10-membered heteroaryl and 5- to 10-membered heterocyclyl groups which are substituted with one or more non-cyclic groups selected from sulfonic acid salts, phosphonic acid salts, phosphonium salts, ammonium salts and carboxylate salts; and (b) pyridinium and imidazolium salts;
wherein the fluorescent sensor compound is linked to a support structure.

13. A fluorescent sensor compound linked to a support structure according to claim 12, wherein the support structure is a hydrogel.

14. A fibre optic sensor comprising a fluorescent sensor compound according to claim 1.

15. A fibre optic sensor comprising a fluorescent sensor compound linked to a support structure according to claim 12.

16. A method of detecting the presence of a target analyte selected from saccharides, amino saccharides, carbonyl saccharides and potassium in a test substance, which method comprises:
(i) exposing a fluorescent sensor compound as claimed in claim 1 to a test substance and measuring the fluorescence of the compound;
(ii) comparing the fluorescence measurement obtained in step (i) against a previously-determined fluorescence measurement of the fluorescent sensor compound in the absence of the target analyte; and
(iii) determining that the target analyte is present if the fluorescence measurement obtained in step (ii) is different from the previously-determined fluorescence measurement.

* * * * *

UNITED STATES PATENT AND TRADEMARK OFFICE
CERTIFICATE OF CORRECTION

PATENT NO.        : 9,115,063 B2
APPLICATION NO.   : 13/263307
DATED             : August 25, 2015
INVENTOR(S)       : Timothy Charles Higgs It is certified that error appears in the above-identified patent and that said Letters Patent is hereby corrected as shown below:

On The Title Page

First Page, Column 1 ((56) Other Publications), please delete "strnctnre" and insert -- structure --, therefor;

First Page, Column 2 ((56) Other Publications), please delete "fluroscence" and insert -- fluorescence --, therefor;

First Page, Column 2 ((56) Other Publications), please delete "Isollleric Forlllylstyrenes" and insert -- Isomeric Formylstyrenes --, therefor;

In The Claims

Column 61, line 35 (Claim 12), please delete "R'R" R''"' and insert -- R'R"R'" --, therefor.

Signed and Sealed this
Ninth Day of February, 2016

Michelle K. Lee
*Director of the United States Patent and Trademark Office*